US009067961B2

(12) United States Patent
Dellinger et al.

(10) Patent No.: US 9,067,961 B2
(45) Date of Patent: Jun. 30, 2015

(54) THIOCARBON-PROTECTING GROUPS FOR RNA SYNTHESIS

(75) Inventors: Douglas J. Dellinger, Boulder, CA (US); Agnieszka B. Sierzchala, Boulder, CO (US); John Turner, Berlin (DE); Joel Myerson, Berkeley, CA (US); Zoltan Kupihar, Szeged (HU); Fernando Ferreira, Loveland, CO (US); Marvin H. Caruthers, Boulder, CO (US); Geraldine F. Dellinger, Boulder, CO (US)

(73) Assignees: Agilent Technologies, Inc., Santa Clara, CA (US); The Regents of the University of Colorado Denver, Denver, CO (US)

( * ) Notice: Subject to any disclaimer, the term of this patent is extended or adjusted under 35 U.S.C. 154(b) by 344 days.

(21) Appl. No.: 13/485,592

(22) Filed: May 31, 2012

(65) Prior Publication Data

US 2012/0238737 A1   Sep. 20, 2012

Related U.S. Application Data

(62) Division of application No. 12/118,655, filed on May 9, 2008, now Pat. No. 8,202,983.

(60) Provisional application No. 60/928,722, filed on May 10, 2007.

(51) Int. Cl.
*C07H 13/12* (2006.01)
*C07H 21/02* (2006.01)
*C07H 19/073* (2006.01)
*C07H 19/16* (2006.01)

(52) U.S. Cl.
CPC .............. *C07H 19/073* (2013.01); *C07H 13/12* (2013.01); *C07H 19/16* (2013.01); *C07H 21/02* (2013.01)

(58) Field of Classification Search
CPC .... C07H 19/24; C07H 19/167; C07H 19/067; C07H 19/04
See application file for complete search history.

(56) References Cited

U.S. PATENT DOCUMENTS

| | | | |
|---|---|---|---|
| 4,415,732 A | 11/1983 | Caruthers et al. |
| 4,668,777 A | 5/1987 | Caruthers et al. |
| 5,859,233 A | 1/1999 | Hirschbein et al. |
| 6,027,890 A | 2/2000 | Van Ness |
| 6,127,535 A | 10/2000 | Beigelman et al. |
| 6,222,030 B1 | 4/2001 | Dellinger et al. |
| 6,258,793 B1 | 7/2001 | Palle et al. |
| 6,630,581 B2 | 10/2003 | Dellinger et al. |
| 6,673,918 B2 | 1/2004 | Bellon |
| 7,067,641 B2 | 6/2006 | Dellinger |
| 7,101,986 B2 | 9/2006 | Dellinger et al. |
| 7,135,565 B2 | 11/2006 | Dellinger et al. |
| 7,193,077 B2 | 3/2007 | Dellinger et al. |
| 7,271,258 B2 | 9/2007 | Dollinger et al. |
| 7,368,550 B2 | 5/2008 | Dellinger et al. |
| 7,411,061 B2 | 8/2008 | Myerson et al. |
| 7,417,139 B2 | 8/2008 | Dellinger et al. |
| 7,427,679 B2 | 9/2008 | Dellinger et al. |
| 7,435,810 B2 | 10/2008 | Myerson et al. |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,759,471 B2 | 7/2010 | Dellinger et al. |
| 7,790,387 B2 | 9/2010 | Dellinger et al. |
| 7,999,087 B2 | 8/2011 | Dellinger et al. |
| 2002/0025539 A1 | 2/2002 | Dellinger |
| 2002/0045221 A1 | 4/2002 | Dellinger et al. |
| 2002/0058802 A1 | 5/2002 | Dellinger et al. |
| 2004/0116687 A1 | 6/2004 | Dellinger et al. |
| 2004/0230052 A1 | 11/2004 | Dellinger et al. |
| 2005/0048496 A1 | 3/2005 | Dellinger et al. |
| 2005/0048497 A1 | 3/2005 | Dellinger et al. |
| 2005/0048601 A1 | 3/2005 | Dellinger et al. |
| 2005/0049407 A1 | 3/2005 | Dellinger et al. |
| 2005/0049411 A1 | 3/2005 | Dellinger et al. |
| 2005/0136477 A1 | 6/2005 | Akhavan-Tafti |
| 2005/0266422 A1 | 12/2005 | Vagle et al. |
| 2006/0247430 A1 | 11/2006 | Dellinger et al. |
| 2006/0252924 A1 | 11/2006 | Dellinger et al. |
| 2006/0293511 A1 | 12/2006 | Dellinger et al. |
| 2007/0099859 A1 | 5/2007 | Dellinger et al. |
| 2007/0100136 A1 | 5/2007 | Dellinger et al. |
| 2007/0100137 A1 | 5/2007 | Dellinger |
| 2007/0100138 A1 | 5/2007 | Dellinger et al. |

(Continued)

FOREIGN PATENT DOCUMENTS

WO        03087053 A2    10/2003

OTHER PUBLICATIONS

Oba et al., "Radical-based transformation of vicinal diols to olefins via thioxocarbamate derivatives: a simple approach to 2',3'-didehydro-2',3'-dideoxynucleosides" Tetrahedron Letters (2003) vol. 44 pp. 4027-4029.*
Chinese Patent Appl. No. 200880024107.2, Fifth Examination Report, Dec. 18, 2013.
Indian Patent Appl. No. 7969/DELNP/2009, First Examination Report, Jan. 10, 2014.
EP12163999.1-1452, Communication Pursuant to Article 94(3) EPC, Mar. 20, 2014.
EP08755268.3-1452, Communication Pursuant to Article 94(3) EPC, Mar. 18, 2014.
JP2010-507715, Notice of Allowance, Mar. 28, 2014.

(Continued)

*Primary Examiner* — Eric Olson

(57) ABSTRACT

Aspects of the invention include 2' protected nucleoside monomers that are protected at the 2' site with thiocarbon protecting groups. Thiocarbon protecting groups of interest include thiocarbonate, thionocarbonate, dithiocarbonate groups, as well as thionocarbamate protecting groups. Aspects of the invention further include nucleic acids that include the protecting groups of the invention, as well as methods of synthesizing nucleic acids using the protecting groups of the invention.

20 Claims, No Drawings

(56) References Cited

U.S. PATENT DOCUMENTS

| | | |
|---|---|---|
| 2007/0224602 A1 | 9/2007 | Dellinger et al. |
| 2007/0224603 A1 | 9/2007 | Dellinger et al. |
| 2008/0076913 A1 | 3/2008 | Dellinger et al. |
| 2008/0146787 A1 | 6/2008 | Timar et al. |
| 2008/0194502 A1 | 8/2008 | Dellinger et al. |
| 2008/0206850 A1 | 8/2008 | Dellinger et al. |
| 2008/0206851 A1 | 8/2008 | Dellinger |
| 2008/0227964 A1 | 9/2008 | Dellinger et al. |
| 2009/0209479 A1 | 8/2009 | Dellinger et al. |
| 2010/0076183 A1 | 3/2010 | Dellinger et al. |

OTHER PUBLICATIONS

Vachet, Richard W., et al., "Novel Peptide Dissociation: Gas-Phase Intramolecula Rearrangement of Internal Amino Acid Residues"; Journal of The American Chemical Society, vol. 119, Issue 24; Jun. 18, 1997; DOI: 10.1021/ja9640758; pp. 5481-5488. (Abstract only).

Albert, Thomas J., "Light-directed 5'®3' synthesis of complex oligonucleotide microarrays"; Nucleic Acids Research, vol. 31, No. 7, (2003); DOI: 10.1093/nar/gng035; pp. 1-9.

Bell, R. P., "The catalyzed dehydration of acetaldehyde hydrate, and the effect of structure on the velocity of protolytic reactions"; Physical Chemistry Laboratory, University of Oxford, vol. 197, Jun. 7, 1949); pp. 141-159.

Carey, et al., part of "Chapter 5 Nucleophilic Substitute, Table 5.6. Hardness and Softness of Some Common Ions and Molecules"; Advanced Organic Chemistry, 3rd Edition, Plenum Press New York, NY, 1990; p. 288.

Edwards, John O., et al., "The Factors Determining Nucleophilic Reactivities"; Journal of The American Society, vol. 84(1); Jan. 5, 1962; pp. 16-24.

Fuji, Masayo, et al., "(Butylthio)carbonyl Group: A New Protecting Group for the Guanine Residue in Oligoribonucleotide Synthesis"; Tetrahedron Letters, vol. 28, No. 46, 1987; pp. 5713-5716.

Greene, Theodora W., et al., "Protective Groups In Organic Synthesis", Third Edition, A Wiley-Interscience Publication, John Wiley & Sons, Inc., 1999, ISBN 0-471-22057-04 and ISBN 0-471-16019-9 (68 pages).

Hildbrand, Stefan, et al., "5-Substituted 2-Aminopyridine C-Nucleosides as Protonated Cytidine Equivalents: Increasing Efficiency and Selectivity in DNA Triple-Helix Formation"; Journal of The American Chemical Society, 1997, 119; pp. 5499-5511.

Jencks, William P., et al., "Reactivity of Nucleophilic Reagents towards Esters"; Contribution No. 47 from the Graduate Department of Biochemistry, Brandeis University; vol. 82, Jul. 27, 1959; pp. 1778-1786.

Kice, John L., et al., "Relative Nucleophilicity of Common Nucleophiles toward Sulfonyl Sulfur. II. Comparison of the Relative Reactivity of Twenty Different Nucleophiles toward Sulfonyl Sulfur vs. Carbonyl Carbon"; Journal of The American Chemical Society, 95:12, Jun. 13, 1973; pp. 3912-3917.

Kirby, Anthony J., et al., "Reactions of alpha-nucleophiles with a model phosphate diester"; Issue in Honor of Prof. Harri Lonnberg; ARKIVOC 2009 (iii), Arkat USA, Inc.; ISSN: 1551-7012; pp. 28-38.

Losse, Gunter, et al., "Synthese von 2'-(tert-Butyloxycarbonyl)ribonucleosiden (Synthesis of 2'-(tert-butyloxycarbonyl) ribonucleosides)"; Snythesis, Nov. 1990; pp. 1035-1036.

McIsaac Jr., J.E., et al., "The Nucleophilic Reactivity of Peroxy Anions"; The Journal of Organic Chemistry, vol. 37, No. 7, 1972; pp. 1037-1041.

International Search Report and Written Opinion dated Aug. 22, 2008, issued by the International Searching Authority (PCT) in related International Application No. PCT/US07/64636 (11 pages).

Pitsch, Stefan, et al., Unit 2.9 Basic Protocol, Protection of Nucleosides for Oligonucleotide Synthesis, Supplement 7—"Preparation of 2'-O-[Triisopropylsilyl)oxy]methyl-protected Ribonucleosides"; Current Protocols in Nucleic Acid Chemistry, John Wiley & Sons, Inc., (2001); pp. 2.9.1-2.9.14.

Scaringe, Stephen A., et al., Unit 2.10 Protection of Nucleosides for Oligonucleotide Synthesis—"Preparation of 5'-Silyl-2'Orthoester Ribonucleosides for Use in Oligoribonucleotide Synthesis"; Current Protocols in Nucleic Acid Chemistry, 2004 John Wiley & Sons, Inc.; pp. 2.10.1-2.10.16.

Schneiderwind, Ruth G. K., et al., "Die 2,2,2-Trichlor-t-Butyloxycarbonyl-Gruppe, Eine Neue N-Schutzgruppe Fur Oligonucleotidsynthesen"; Tetrahedron Letters vol. 39, No. 13, 1983; pp. 2207-2210.

Watkins, Bruce E., et al., "Synthesis of Benzyl and Benzyloxycarbonyl Base-Blocked 2'-Deoxyribonucleosides"; Journal of Organic Chemistry, vol. 47, 1982 American Chemical Society; pp. 4471-4477.

Chinese Patent Appl. No. 200880024107.2, Fourth Examination Report, Aug. 23, 2013.

EP 12 163 999.1-1452, Communication Pursuant to Article 94(3)EPC, Jul. 19, 2013.

EP 08 755 268.3-1452, Communication Pursuant to Article 94(3)EPC, Jul. 19, 2013.

JP 2010-507715, Decision of Rejection, Oct. 8, 2013.

Liu, etal, "Synthesis and Biological Evaluation of 2',3'-Didehydro-2', 3'-Dideoxy-9-Deazaguanosine, A Monophosphate Prodrug and Two Analogues, 2',3'-Dideoxy-9-Deazaguanosine and 2',3'-Didehydro-2',3'-Dideoxy-9-Deazainosine", Nucleosides, Nucleotides, and Nucleic Acids (2005) vol. 24 No. 2, 135-145.

Nowak, Ireneusz, etal, "Addition of Difluorocarbene to 3',4'-Unsaturated Nucleosides: Synthesis of 21-Deoxy Analogues with a 2-Oxabicyclo[3.I.O]hexane", J. Org. Chem. (2007), 72, 532-537.

Oba, Makoto, etal, "Radical-based transformation of vicinal dials to olefins via thioxocarbamate derivatives: a simple approach to 2',3'-didehydro-2', 3'-dideoxynucleosides", Tetrahedron Letters (2003) 4027-4029.

PCT/US07/84636, Int'l Search Report Dated Aug. 22, 2008.

Hildbrand, etal, "5-Substituted 2-Aminopyridine C-Nucleosides as Protonated Cytidine Equivalents: Increasing Efficiency and Selectivity in DNA Triple-Helix Formation", J. Am. Chem. Soc. 1997, 119, 5499-5511.

* cited by examiner

THIOCARBON-PROTECTING GROUPS FOR RNA SYNTHESIS

CROSS REFERENCE TO RELATED APPLICATION

This application is a divisional and claims the benefit of application Ser. No. 12/118,655, filed on May 9, 2008, which claims the benefit under 35 U.S.C. §119(e) of prior U.S. provisional application Ser. No. 60/928,722 filed May 10, 2007. These prior applications are incorporated by reference in their entirety.

INTRODUCTION

Chemical synthesis of RNA is a much more difficult task than chemical synthesis of DNA, because the 2'-hydroxyl group in the ribose has to be protected during chemical synthesis. The close proximity of a protected 2'-hydroxyl to the internucleotide phosphate presents problems, both in terms of formation of the internucleotide linkage and in the removal of the 2'-protecting group once the oligoribonucleotide is synthesized. In addition, the internucleotide bond in RNA is far less stable than that in DNA.

Until recently, the typical approach to RNA synthesis utilized ribonucleoside monomers in which the 5'-hydroxyl group was protected by the acid-labile dimethoxytrityl (DMT) protecting group, which can be removed under acidic conditions after coupling of the monomer to the growing oligoribonucleotide. Various acid-stable protecting groups have been placed on the 2'-hydroxyl to prevent isomerization and cleavage of the internucleotide bond during the acid deprotection step. The most popular of these acid-stable protecting groups seems to be the tert-butyl-dimethylsilyl group, known as TBDMS (Ogilvie et al., 1979). The use of TBDMS as 2'-protecting group dominated the previously small market for RNA chemical synthesis for a very long time (Usman et al., 1987; Ogilvie et al., 1988).

However, oligoribonucleotide syntheses carried out using TBDMS are by no means satisfactory and typically produce RNA products of poor quality. As a result, the TBDMS protecting group migrates from the 2'-position to the 3'-position. Furthermore, during the synthesis of the monomer (e.g., 5'-O-DMT-2'-O-TBDMS-ribo-3-O-(beta-cyanoethyl, N-diisopropyl)phosphoramidite), introduction of the 2'-silyl group is non-regioselective, thus it can be added to either the 2' or 3' position. Combined with the added chemical requirements to prevent migration of the silyl group during phosphoramidite production, synthesis of the monomer is challenging and costly. It is also well known in the art that the coupling efficiency of these monomers is greatly decreased due to steric hindrance of the 2'-TBDMS protecting group, which not only affects the yield and purity of the full-length product, but also limits the length of the oligoribonucleotide that can be achieved by this method.

The demand for synthetic RNA has been increasing, largely due to the discovery of RNA interference. Therefore, it is desirable to develop improved RNA synthesis schemes, particularly 2'-protecting groups, to meet the growing needs.

SUMMARY

Aspects of the invention include 2' protected nucleoside monomers that are protected at the 2' site with thiocarbon-protecting groups. Thiocarbon protecting groups of interest include but are not limited to thiocarbonate, thionocarbonate and dithiocarbonate protecting groups, as well as thionocarbamate protecting groups. Aspects of the invention further include nucleic acids that include the protecting groups of the invention, as well as methods of synthesizing nucleic acids using the protecting groups of the invention.

DEFINITIONS

Prior to describing the invention in further detail, the terms used in this application are defined as follows unless otherwise indicated.

A "nucleotide" or "nucleotide moiety" refers to a sub-unit of a nucleic acid (whether DNA or RNA or analogue thereof) which includes a phosphate group, a sugar group and a heterocyclic base, as well as analogs of such sub-units. Other groups (e.g., protecting groups) can be attached to any component(s) of a nucleotide.

A "nucleoside" or "nucleoside moiety" references a nucleic acid subunit including a sugar group and a heterocyclic base, as well as analogs of such sub-units. Other groups (e.g., protecting groups) can be attached to any component(s) of a nucleoside.

A "nucleoside residue" refers to a molecule having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2% modified nucleosides, peptide nucleic acids, oligomeric nucleoside phosphonates, and any polynucleotide that has added substituent groups, such as protecting groups or linking groups.

An "internucleotide bond" or "nucleotide bond" refers to a chemical linkage between two nucleoside moieties, such as the phosphodiester linkage in nucleic acids found in nature, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group.

A "group" includes both substituted and unsubstituted forms. Substituents of interest include one or more lower alkyl, amino, imino, amido, alkylamino, arylamino, alkoxy, aryloxy, thio, alkylthio, arylthio, or aryl, or alkyl; aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl, or optionally substituted on one or more available carbon atoms with a nonhydrocarbyl substituent such as cyano, nitro, halogen, hydroxyl, sulfonic acid, sulfate, phosphonic acid, phosphate, phosphonate, or the like. Any substituents are chosen so as not to substantially adversely affect reaction yield (for example, not lower it by more than 20% (or 10%, or 5%, or 1%) of the yield otherwise obtained without a particular substituent or substituent combination). Further, substituents are chosen so as to be chemically compatible with the other groups present and to avoid side reactions known to those skilled in the art. For example, an alcohol would not be substituted with a lithium group, as the hydroxide of the alcohol and the lithium group are incompatible and would react with each other. For any group in this disclosure, each substituent may include up to 40, 35, 30, 25, 20, 18, 16, 14, 12, 11, 10, 9, 8, 7, 6, 5, 4 or 3 carbon atoms. Overall, the total number of carbon atoms in all the substituents for any group is, in certain embodiments, 80, 75, 70, 65, 60, 55, 50, 45, 40, 35, 30, 25, 20, 18, 16, 14, 12, 11, 10, 9, 8, 7, 6, 5, 4 or 3 or less.

The term "heterocycle", "heterocyclic", "heterocyclic group" or "heterocyclo" refers to fully saturated or partially or completely unsaturated cyclic groups having at least one heteroatom in at least one carbon atom-containing ring, including aromatic ("heteroaryl") or nonaromatic (for example, 3 to 13 member monocyclic, 7 to 17 member bicyclic, or 10 to 20 member tricyclic ring systems). Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions. Nitrogen-containing bases are examples of heterocycles. Other examples include piperidinyl, morpholinyl and pyrrolidinyl.

The terms "substituted heterocycle", "substituted heterocyclic", "substituted heterocyclic group" and "substituted heterocyclo" refer to heterocycle, heterocyclic, and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3 to 7 member ring.

The term "electron-withdrawing group" refers to a moiety that has a tendency to attract valence electrons from neighboring atoms (i.e., the substituent is electronegative with respect to neighboring atoms). A quantification of the level of electron-withdrawing capability is given by the Hammett sigma constant. This well known constant is described in many references, for instance, March, Advanced Organic Chemistry 251-59, McGraw Hill Book Company, New York, (1977). Electron-withdrawing groups include nitro, acyl, formyl, sulfonyl, trifluoromethyl, cyano, chloride, and the like.

The term "electron-donating group" refers to a moiety that has a tendency to repel valence electrons from neighboring atoms (i.e., the substituent is less electronegative with respect to neighboring atoms). Electron-donating groups include amino, methoxy, alkyl (including C1-6 alkyl that can have a linear or branched structure), C4-9 cycloalkyl, and the like.

The phrase "protecting group" as used herein refers to a species which prevents a portion of a molecule from undergoing a specific chemical reaction, but which is removable from the molecule following completion of that reaction. A "protecting group" is used in the conventional chemical sense as a group which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

A "hydroxyl protecting group" or "O-protecting group" refers to a protecting group where the protected group is a hydroxyl. A "reactive-site hydroxyl" is the terminal 5'-hydroxyl during 3'-5' polynucleotide synthesis, or the 3'-hydroxyl during 5'-3' polynucleotide synthesis. A "free reactive-site hydroxyl" is a reactive-site hydroxyl that is available to react to form an internucleotide bond (e.g. with a phosphoramidite functional group) during polynucleotide synthesis.

A "thiocarbon protecting group" refers to a protecting group linked through a carbonyl or thionocarbonyl moiety which additionally has an oxygen, sulfur or nitrogen linked to one or more radicals independently selected from hydrogen, hydrocarbyls, and substituted hydrocarbyls with the proviso that when the thiocarbon protecting group is linked to the radical through a nitrogen, the radical can be additionally selected from aryls, substituted aryls, heterocycles or substituted heterocycles.

"The term "deprotecting simultaneously" refers to a process which aims at removing different protecting groups in the same process and performed substantially concurrently or concurrently. However, as used herein, this term does not imply that the deprotection of the different protecting groups occur at exactly the same time or with the same rate or same kinetics.

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

The term "phosphoramidite group" refers to a group comprising the structure —P—(OR$^{13}$)(NR$^{14}$R$^{15}$), wherein each of R$^{13}$, R$^{14}$, and R$^{15}$ is independently a hydrocarbyl, substituted hydrocarbyl, heterocycle, substituted heterocycle, aryl or substituted aryl. In some embodiments, R$^{13}$, R$^{14}$, and R$^{15}$ may be selected from lower alkyls, lower aryls, and substituted lower alkyls and lower aryls (preferably substituted with structures containing up to 18, 16, 14, 12, 11, 10, 9, 8, 7, 6, 5, 4, 3 or 2 carbons). In some embodiments, R$^{13}$ is 2-cyanoethyl or methyl, and either or both of R$^{14}$ and R$^{15}$ is isopropyl. R$^{14}$ and R$^{15}$ can optionally be cyclically connected.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

Moreover, the term "alkyl" includes "modified alkyl", which references an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. Similarly, the term "lower alkyl" includes "modified lower alkyl", which references a group having from one to eight carbon atoms and further having additional groups, such as one or more linkages selected from ether-, thio-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "hydrocarbyl" refers to alkyl, alkenyl or alkynyl. The term "substituted hydrocarbyl" refers to hydrocarbyl moieties having substituents replacing a hydrogen on one or more carbons of the hydrocarbon backbone. Such substituents may include, for example, a hydroxyl, a halogen, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

The term "alkoxy" means an alkyl group linked to oxygen and may be represented by the formula: R—O—, wherein R represents the alkyl group. An example is the methoxy group $CH_3O$—.

The term "aryl" refers to 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocycles). A "lower aryl" contains up to 18 carbons, such as up to 14, 12, 10, 8 or 6 carbons.

The aromatic rings may be substituted at one or more ring positions with such substituents as described above for substituted hydrocarbyls, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —CF$_3$, —CN, or the like.

The terms "halogen" and "halo" refer to fluorine, chlorine, bromine, or iodine.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, boronyl, and modified lower alkyl.

Hyphens, or dashes are used at various points throughout this specification to indicate attachment, e.g. where two named groups are immediately adjacent to a dash in the text, this indicates that the two named groups area attached to each other. Similarly, a series of named groups with dashes between each of the named groups in the text indicated the named groups are attached to each other in the order shown. Also, a single named group adjacent a dash in the text indicates that the named group is typically attached to some other, unnamed group. In some embodiments, the attachment indicated by a dash may be, e.g., a covalent bond between the adjacent named groups. At various points throughout the specification, a group may be set forth in the text with or without an adjacent dash, (e.g. amido or amido-, further e.g. alkyl or alkyl-, yet further Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g., where a linkage is intended, such as linking groups).

Dashed lines (e.g., - - - - - - ) are used throughout the specification adjacent to named groups to indicate attachment to some other, unnamed group.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present and/or determining whether it is present or absent.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 1%, at least about 5%, at least about 10%, at least about 20%, at least about 30%, at least about 50%, preferably at least about 80%, or more preferably at least about 90% of the sample (excluding solvents). For example, a sample of isolated RNA will typically comprise at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophresis, ion-exchange chromatography, affinity chromatography, flow sorting, and sedimentation according to density. In typical embodiments, one or more of the nucleotide composition(s) is in isolated form; more typically, all three are obtained in isolated form prior to use in the present methods.

The term "pre-determined" refers to an element whose identity is known prior to its use. For example, a "pre-determined sequence" is a sequence whose identity is known prior to the use or synthesis of the polynucleotide having the sequence. An element may be known by name, sequence, molecular weight, its function, or any other attribute or identifier.

"Upstream" as used herein refers to the 5' direction along a polynucleotide, e.g. an RNA molecule. "Downstream" refers to the 3' direction along the polynucleotide. "3'-" and "5'-" have their conventional meaning as known in the art.

DETAILED DESCRIPTION

Aspects of the invention include 2' protected nucleoside monomers that are protected at the 2' site with a thiocarbon protecting group. Thiocarbonate protecting groups of interest include thiocarbonate and dithiocarbonate groups, as well as thionocarbamate protecting groups. Aspects of the invention further include nucleic acids that include the protecting groups of the invention, as well as methods of synthesizing nucleic acids using the protecting groups of the invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be noted that, as is conventional in drawing some chemical structures, some of the hydrido groups are omitted from the drawn structures for clarity purposes, but should be understood to be present, e.g. where necessary to completely fill out the valence bonding of a carbon in a drawn structure.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Monomers Protected with Thiocarbon Protecting Groups

As summarized above, aspects of the invention include 2'-thiocarbon protecting groups and monomers that include the thiocarbon protecting groups protecting the 2' oxygen of the monomer. By thiocarbon protecting group is meant a protecting group which includes a sulfur atom bonded to a carbon atom, where the sulfur atom may be bonded to the carbon atom by either a single or double bond. The protecting group may or may not include further heteroatoms, e.g., oxygen, nitrogen, etc. In certain embodiments, the protecting group is a thiocarbonate or dithiocarbonate protecting group. In yet other embodiments, a nitrogen atom is present, such as is present in the thionocarbamate protecting groups of the invention, reviewed in greater detail below. These protecting groups, except for the thionocarbamate do not contain a phenyl group as a radical. As such, thiocarbon protecting groups of the invention do not include phenylthionocarbonate, phenylthiocarbonate and phenyldithiocarbonates are excluded from this invention.

Embodiments of the invention include nucleoside monomers having 2' thiocarbonate protecting groups (where "thiocarbonate" includes dithiocarbonate), e.g., as described by Formula (I):

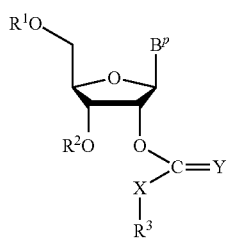

I wherein:

$B^P$ is a protected or unprotected heterocycle;

each of $R^1$ or $R^2$ is independently selected from hydrogen, a protecting group, and a phosphoramidite group;

X and Y are independently sulfur or oxygen, wherein at least one of X and Y is sulfur; and $R_3$ is independently selected from hydrocarbyls and substituted hydrocarbyls. In certain embodiments where $R_3$ is a secondary (—CH—R'R") hydrocarbyl group or a substituted secondary (—CH—R'R") hydrocarbyl group, R' and R" are selected independently from hydrogen, hydrocarbyls, substituted hydrocarbyls, aryls and substituted aryls, where in certain embodiments when Y is oxygen, $R_3$ is not a tertiary hydrocarbyl, i.e., $R_3$ is not

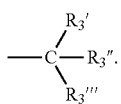

Compounds described by Formula I include, but are not limited to, thiocarbonates, dithiocarbonates, and thionocarbonates. Embodiments of these compounds include those represented by the following formulas Ic and Id and Ie:

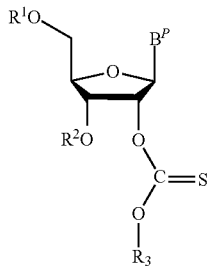

Ic

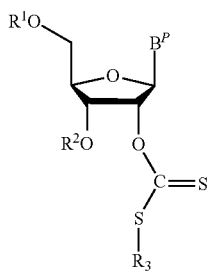

Id

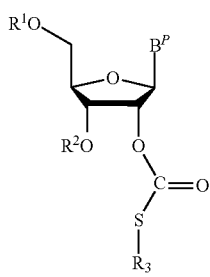

Ie wherein:

$R_3$ is independently selected from hydrocarbyls, and substituted hydrocarbyls provided that when $R_3$ is a secondary (—CH—R'R") hydrocarbyl group or a substituted secondary (—CH—R'R") hydrocarbyl group, R' and R" each are selected independently from hydrogen, hydrocarbyls, substituted hydrocarbyls, aryls and substituted aryls with the additional proviso with respect to only the compound shown in structure Ie that $R_3$ is not a tertiary hydrocarbyl as described by the structure

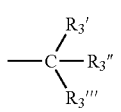

meaning that at least one of $R_3'$, $R_3''$, $R_3'''$ is H.

Additional examples of suitable $R_3$ groups may be found in pending U.S. application Ser. No. 11/388,112 titled "Monomer Compositions for the Synthesis of RNA, Methods of Synthesis, and Methods of Deprotection," and filed on Mar. 23, 2006, the disclosure of which is herein incorporated by reference.

In yet another embodiment of the present invention, $R^3$ in Formula I is a methyl, ethyl, isopropyl group, or benzyl group. Examples of such embodiments include compounds of the following structures:

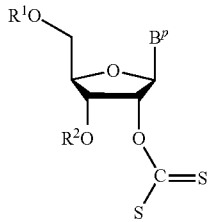

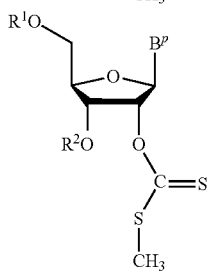

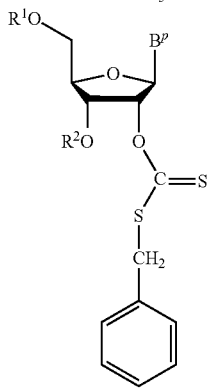

In certain embodiments, monomers of the invention include 2' thionocarbamate protecting groups, e.g., as found in compounds by the structure shown in Formula II:

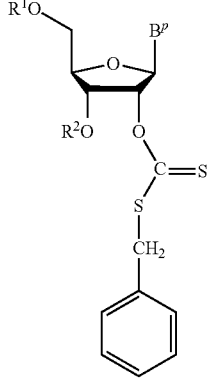

(II)

wherein:

$B^P$ is a protected or unprotected heterocycle;

each of $R^1$ or $R^2$ is independently selected from hydrogen, a protecting group, and a phosphoramidite group;

N is $NH_2$ or a secondary amine (—NH—Z), a secondary hydroxylamine (—NH—O—Z) a tertiary amine (—N—ZZ"), wherein Z and Z" are independently selected from hydrocarbyls, substituted hydrocarbyls, aryls, substituted aryls, and wherein Z or Z" can be cyclically linked to N, or a tertiary hydroxylamine (—N—Z—OZ"), wherein Z and Z"

are independently selected from hydrocarbyls, substituted hydrocarbyls, aryls, substituted aryls, and wherein Z or Z" can be cyclically linked to N; and Carbamate protecting groups of the invention include primary, secondary, and tertiary thionocarbamates. Embodiments of these compounds include those represented by the following formulas IIc and IId and IIe and IIf and IIg and IIh:

IIc
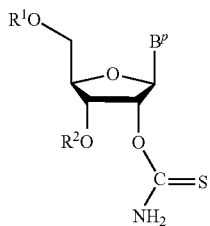

IId
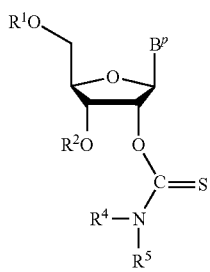

IIe
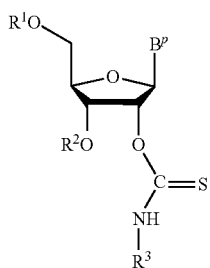

IIf
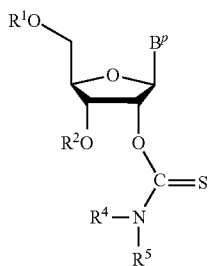

IIg
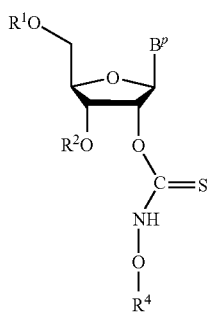

IIh
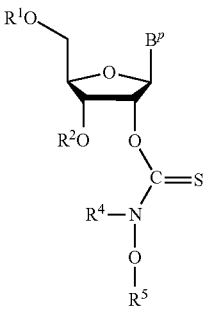

wherein:
$R_3$ is selected from hydrocarbyls, substituted hydrocarbyls, aryls, substituted aryls with the provisio only for IIc, that $R_3$ is not a 2-(N-amido) substituted phenyl;

$R_4$ and $R_5$ are independently selected from hydrocarbyls, substituted hydrocarbyls, aryls, substituted aryls, provided that $R_4$ and $R_5$ can be cyclically linked to N.

Specific compounds of interest include those described by the following structures:

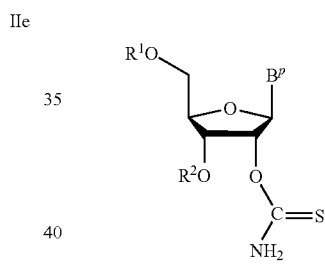

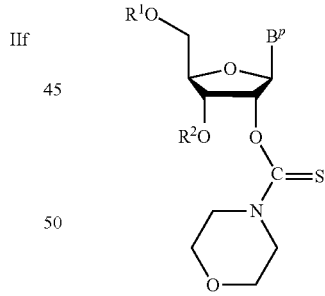

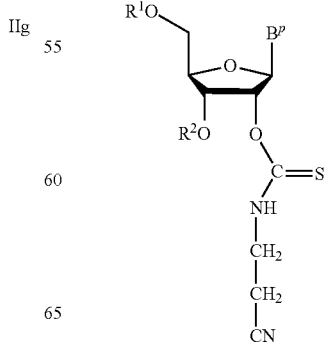

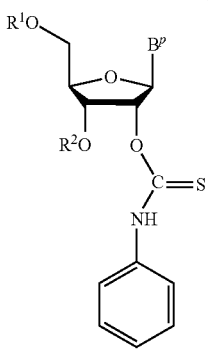

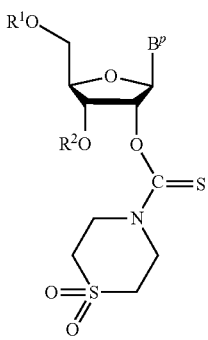

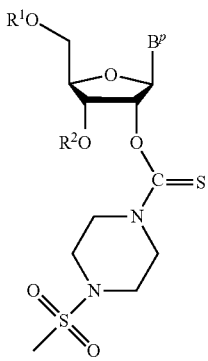

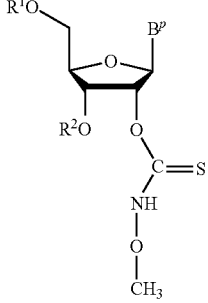

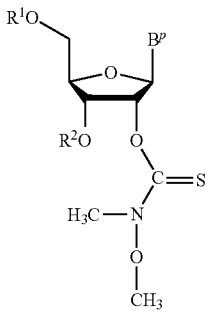

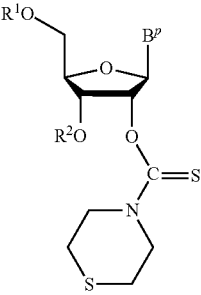

With respect to the above formulas, the $B^P$ group is a protected or non-protected heterocycle. The heterocycle may be selected from the naturally occurring purine and pyrimidine bases, e.g., adenine (A), thymine (T), cytosine (C), guanine (O), or uracil (U), or modified purine and pyrimidine bases, and common analogs, e.g., such as are recited herein. Certain purine or pyrimidine analogs that are contemplated in this context include those described in U.S. patent application Ser. No. 10/324,409 entitled "Method of Producing Nucleic Acid Molecules with Reduced Secondary Structure", filed on Dec. 18, 2002; and also those described in U.S. patent application Ser. No. 09/358,141, now abandoned, entitled "Method of Producing Nucleic Acid Molecules with Reduced Secondary Structure", filed on Jul. 20, 1999.

In some embodiments, the heterocycle is selected from 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In some embodiments, the heterocycle may have a protecting group, as is commonly known in the art of polynucleotide synthesis. In certain embodiments, a heterocycle protecting group selected from acetyl, difluoroacetyl, trifluoroacetyl, isobutyryl, benzoyl, 9-fluorenylmethoxycarbonyl, phenoxyacetyl, dimethylformamidine, dibutylforamidine, or N,N-diphenyl carbamate is attached to the heterocycle.

Synthesis of 2' Thiocarbon Protecting Group Protected Monomers

The thiocarbon protecting group containing nucleoside monomers of the invention can be produced using any convenient protocol. In certain embodiments, protected nucleoside monomers of the invention are produced using a protocol in which a nucleoside monomer having the structure shown in Formula (III)

III

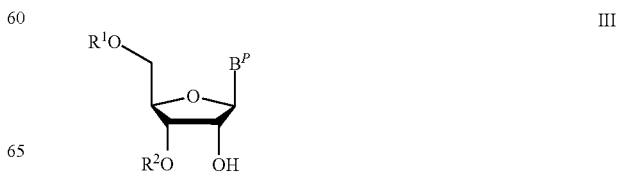

wherein:

B^P is a protected or unprotected nitrogen-containing base; and $R^1$ and $R^2$ are each independently H, a phosphoroamidate group, a hydroxyl protecting group, or $R^1$ and $R^2$ are linked to form a bidentate protecting group, such as a 1,3-tetraisopropyldisiloxane (TIPS) group;

is contacted with a compound having the structure: Q-LG, wherein:

Q is a thiocarbon protecting group, e.g., as described above; and

LG is a leaving group, such as a halo group;

under conditions sufficient to produce a 2' protected nucleoside monomer of the structure of Formula (IV).

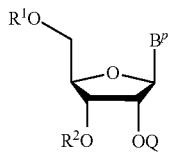

IV

LG may be any convenient leaving group. Leaving or activating groups include, but are not limited to: imidazole, chloro, p-nitrophenoxy, pentafluoro phenoxy, O-succinimidyl, trichloromethyl, bromo, and iodo.

In certain embodiments, as illustrated below, synthesis of monomers of the invention employs a reagent, such as a Markewicz TIPS reagent, to localize protecting groups to the 2'-OH site of the composition under synthesis, i.e., to provide regioselectivity. In the following scheme, $R^i$ is a thiocarbon protecting group. The specific introduction on the 2'-hydroxyl protecting group is performed through the transient protection of the 5' and 3'-hydroxyl groups, e.g., through the use if the Markewicz disilyloxane protecting group. The 1,3-tetraisopropyl disiloxane (TIPS) shown in the below scheme is a transient bidentate protecting group that is used to block the 5' and 3' hydroxyls simultaneously, allowing the 2'-hydroxyl to be regioselectively protected. Other transient bidentate protecting groups may also be employed. The 1,3-tetraisopropyl disiloxane group is subsequently removed using a solution of fluoride ions.

Scheme 1.

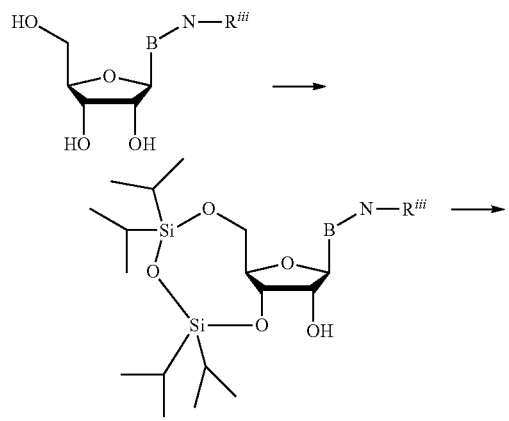

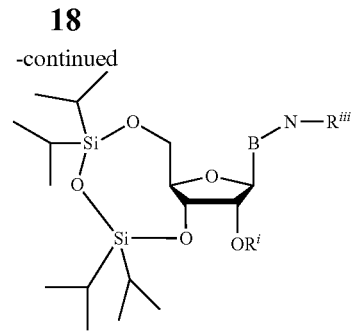

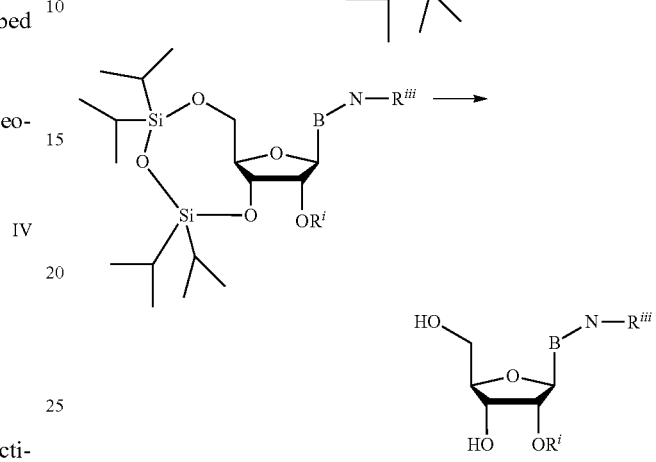

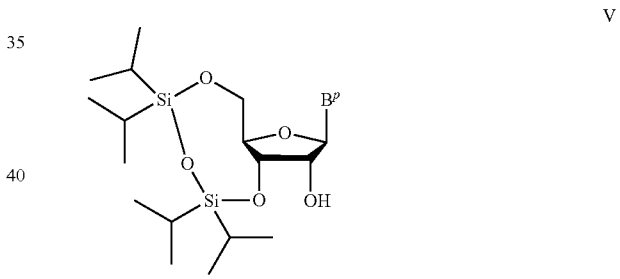

Accordingly, aspects of the invention include methods of making compounds of the invention by reacting a compound of formula V:

V wherein B^P is a protected or unprotected nitrogen-containing base;

with a chlorothioformate of formula Cl-C(S)—$R_3$ wherein $R_3$ is independently selected from hydrocarbyls, substituted hydrocarbyls, provided that $R_3$ is not a tertiary hydrocarbyl and when $R_3$ is a secondary (—CH—R'R") hydrocarbyl group or a secondary substituted (—CH—R'R") hydrocarbyl group, R' and R" is selected independently from hydrogen, hydrocarbyls, substituted hydrocarbyls, aryls and substituted aryls to produce a 5',3'-TIPS-2'-O—($R_3$-thio)carbonyl intermediate;

b) removing the 5',3'-tetraisopropyldisiloxane protecting group with 15 eq to 40 eq of HF/pyridine to produce the 2'-O—($R_3$-thio)carbonyl ribonucleoside intermediate;

c) reacting the intermediate of step b) with DMTrCl and with 5eq to 10 eq of collidine or lutidine and optionally adding DMAP or NMI to produce a 5'-O-DMT-2'-O-thiocarbonyl-ribonucleoside derivative;

d) reacting the intermediate from step c) with a phosphytilating reagent selected from: CNEO-P(Cl)—N(iPr)$_2$ or (diisopropyl)aminomethoxychlorophosphine to produce a 5'-O-DMT-2'-O—$R_3$-thiocarbonyl-3'-O-methyl(-or cyanoethyl)

phosphoramidite. The above reaction conditions are illustrative, with analogous conditions and protocols also included within the scope of the invention.

It has been shown that with the protected 2'-hydroxyl compounds described herein, and the conditions developed to deprotect the TIPS group, this regiospecific transient protection can be performed with unprecedented efficiency. Specific compositions and methods have been developed to deprotect selectively the TIPS protection while preserving the 2'-protecting group. For example, the use of HF/pyridine allows selective deprotection of the TIPS while the thiocarbon protecting group is preserved.

After or during the selective removal of the TIPS protecting group, it is important to consider the possible further reaction of the free 3'-hydroxyl to form a cyclic carbonate. Thiocarbonates on the 2' position do not undergo cyclization during TIPS removal with HF/pyridine/CH$_3$CN. On the other hand, thiocarbonates or carbonates cyclize to some extent when HF/TEA is used instead of HF/Pyridine/CH$_3$CN (see Scheme 2, below).

Scheme 2.

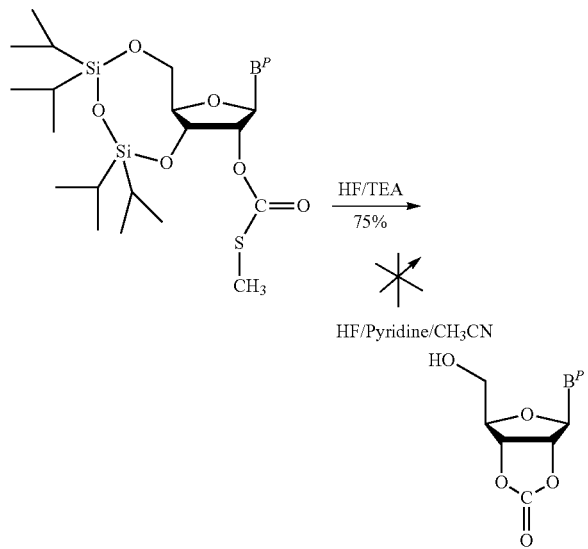

This cyclization, while undesirable, produces a dead-end cyclic carbonate product that can be readily separated from the desired product. The formation of this cyclic species is therefore a preferred side reaction and a benefit to ensuring the integrity of the final monomer product and eventual RNA oligonucleotide. This finding is in contrast to the use of silanes or other protective groups for the 2'-hydroxyl that can isomerize from the 2'-hydroxyl to the 3'-hydroxyl and resulting in RNA products of questionable 5' to 3' linkage integrity. In these deprotection reactions employing HF, complexes of HF, such as HF-TEMED or HF-TMA, can also be used. Other solvents, e.g., dioxane, THF, or methylene chloride, can also be used, although under certain conditions such solvents may result in partial loss of the thiocarbonate group owing to the formation of a cyclic carbonate. Again, the cyclic carbonate is readily separable from the desired product.

The nucleobases for these novel RNA monomers are may be protected using any convenient approach. One approach of interest is known in the art as the Jones Procedure; originally described by Ti et. al. J. Am. Chem. Soc.: 104, 1316-1319 (1982). The Jones Procedure uses the transient silylation of unprotected nucleosides by trimethylsilyl chloride to allow carbonyl halides, activated carbonyl groups or carbonyl anhydrides to react regiospecifically with the exocyclic amine of the nucleobase. In this reaction a large excess of trimethylsilyl chloride is added to a solution of the nucleoside in pyridine and dichloromethane. This results in trimethylsilylation of all of the hydroxyl groups of the sugar residue along with the exocyclic amine groups and potentially of the imino on the hetero bases. When silylated, the exocyclic amine groups retain their reactivity toward carbonyl halides, activated carbonyl groups or carbonyl anhydrides, while the hydroxyl groups of the sugar residue are protected from reaction with the same reagents. This results in regiospecific protection of the exocyclic amines. In the typical procedure trimethylsilyl groups are removed from the hydroxyl moieties by an aqueous workup in the presence of sodium bicarbonate. This procedure can be modified to support a non-aqueous workup by the addition of toluene sulfonic acid in a polar solvent. For RNA monomers synthesized using the Markewicz protecting group TIPS, it is advantageous in certain embodiments to first react the unprotected nucleoside with the TIPS group prior to performing the Jones reaction. Under these conditions the TIPS protected nucleoside is significantly more soluble in organic solvents and as a result of the 5' and 3' hydroxyls being pre-protected, it is possible to use a smaller excess of trimethylsilyl chloride. After workup, the product from these reactions is the N-protected-3',5'-tetraisopropyldisiloxane nucleoside. This compound can then be reacted directly to the 2'-protective group.

The protection of the nitrogen-containing base with the R$_3$-thiocarbonate, R$_3$-dithiocarbonate, or R$_3$-thionocarbonate protecting group also allows for one-step final deprotection of the RNA, with the bases and the 2'-hydroxyl groups being deprotected concurrently, as reviewed in greater detail below.

In some other embodiments of the present invention, the nitrogen-containing bases are protected by blocking groups other than the corresponding 2'-O-thiocarbonates. Here again, a one-step final deprotection of the RNA, with the bases and the 2'-hydroxyl groups being deprotected concurrently can be performed. These kinds of nucleoside monomers can be synthesized by starting from a nucleoside in which the nitrogen-containing base is already protected, for example by an acetyl (Ac), difluoroacetyl, trifluoroacetyl, isobutyryl (iBu), benzoyl (Bz), 9-fluorenylmethoxycarbonyl (Fmoc), phenoxyacetyl (Pac), 4-tert-butylphenoxyacetyl (Tac), isopropylphenoxyacetyl (iPrPac), phenyloxycarbonyl, trifluoromethyloxycarbonyl, difluoromethyloxycarbonyl, fluoromethyloxycarbonyl, trifluoroethyloxycarbonyl, 4-methylphenyloxycarbonyl, 4-ethylphenyloxycarbonyl, 4-isopropylphenyloxycarbonyl, 4-tert-butylphenyloxycarbonyl, 2-methylphenyloxycarbonyl, 2-ethylphenyloxycarbonyl, 2-isopropylphenyloxycarbonyl, 2-tert-butylphenyloxycarbonyl 4-methoxyphenyloxycarbonyl, 4-ethoxyphenyloxycarbonyl, 4-isopropyloxyphenyloxycarbonyl, 4-butyloxyphenyloxycarbonyl, 2-methoxyphenyloxycarbonyl, 2-ethoxyphenyloxycarbonyl, 2-isopropyloxyphenyloxycarbonyl, 2-butyloxyphenyloxycarbonyl, benzylthiocarbonyl, 2-chlorobenzylthiocarbonyl, 4-clorobenzylthiocarbonyl, 2,4-dichlorobenzylthiocarbonyl, 2-fluorobenzylthiocarbonyl, 3-fluorobenzylthiocarbonyl, 4-fluorobenzylthiocarbonyl, 2-trifluoromethylbenzylthiocarbonyl, 3-trifluoromethylbenzylthiocarbonyl, 4-trifluoromethylbenzylthiocarbonyl, 4-nitrobenzylthiocarbonyl, methylthiocarbonyl, ethylthiocarbonyl, isopropylthiocarbonyl, dimethylformamidine, dibutylformamidine N,N-diphenyl carbamate, or the like.

In certain embodiments, the exocyclic amine group on the nucleobase is protected simultaneously with the 2'-hydroxyl using the same reagent, such as carbonyl halides, activated carbonyl groups or carbonyl anhydrides. In this reaction scheme, the unprotected nucleoside may be dissolved in anhydrous pyridine and first reacted with one mole equivalent of 1,3-dichloro-1,1,3,3-tetraisopropyldisiloxane. The reagent specifically reacts to form the 3'-5' cyclically protected nucleoside leaving the exocyclic amine and 2'-hydroxyl moiety available for reaction in the next step with carbonyl halides, activated carbonyl groups or carbonyl anhydrides. See Scheme 3, below.

Scheme 3.

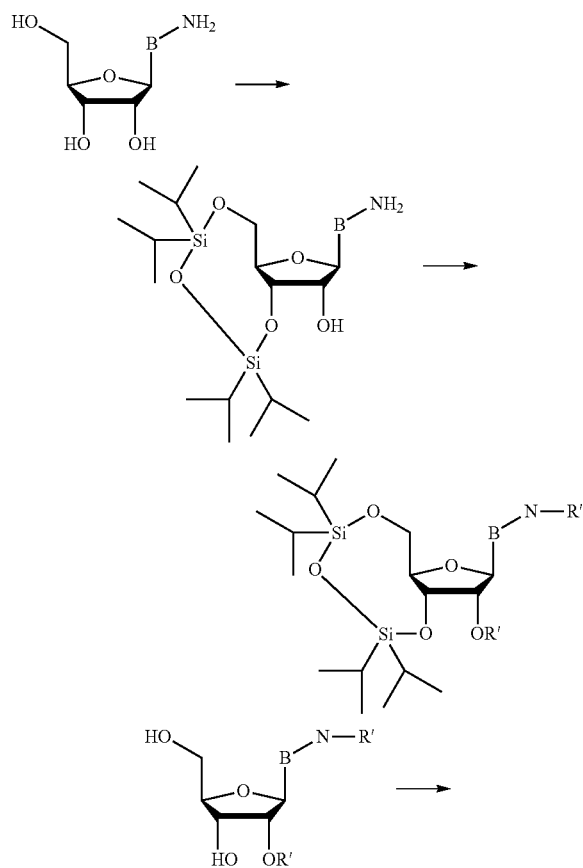

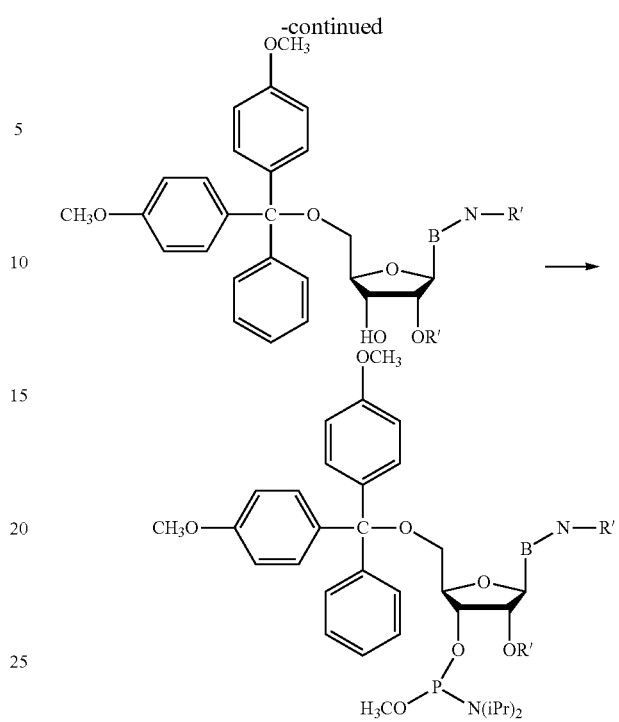

In some other embodiments of the present invention, the nitrogen-containing bases are protected by blocking groups other than thiocarbonates. These kinds of nucleoside monomers can be synthesized by starting from a nucleoside in which the nitrogen-containing base is already protected, for example by an acetyl, difluoroacetyl, trifluoroacetyl, isobutyryl, benzoyl, 9-fluorenylmethoxycarbonyl, phenoxyacetyl, dimethylformamidine, or N,N-diphenyl carbamate. The nucleoside can then be reacted with $TIPSCl_2$ and dithiochloroformate or thiocarbonyl chloroformate, and proceeding as described in Scheme 1 above.

Monomers bearing the $R_3$-thiocarbonate, $R_3$-dithiocarbonate, or $R_3$-thionocarbonate protecting groups can be synthesized using an activated $R_3$-thiocarbonate, $R_3$-dithiocarbonate, or $R_3$-thionocarbonate. Embodiments of suitable schemes are shown in Schemes 4-6 below:

Scheme 4. Synthesis of 5'-O-DMT-2'-O-hydrocarbylthiocarbonyl-3'-O-[methyl-(N,N-diisopropyl)]-phosphoramidite Uridine

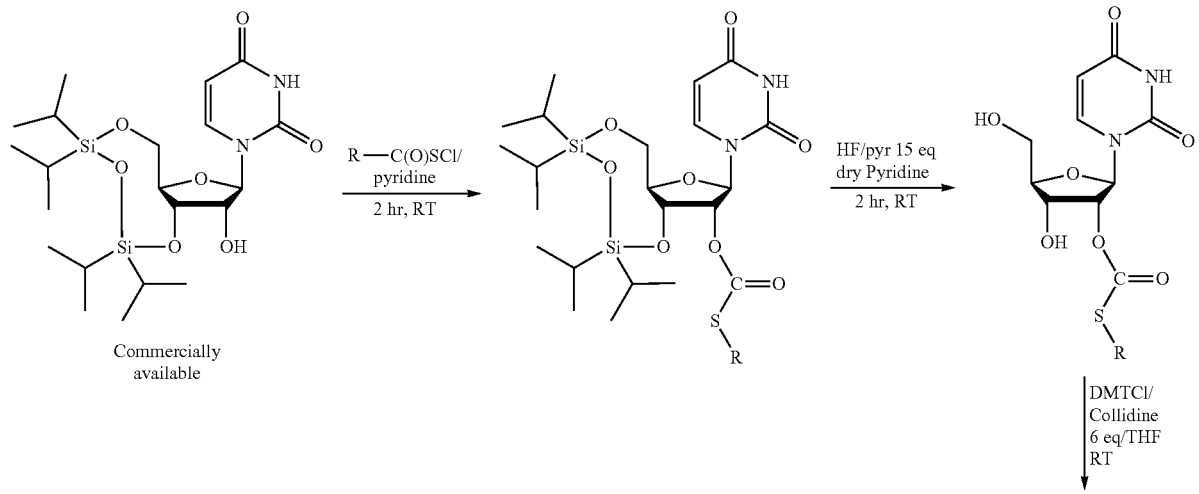

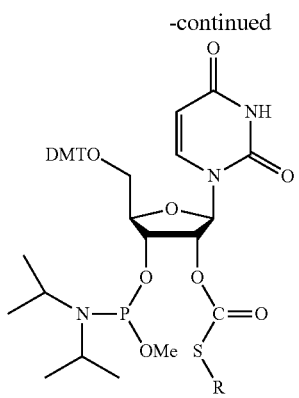
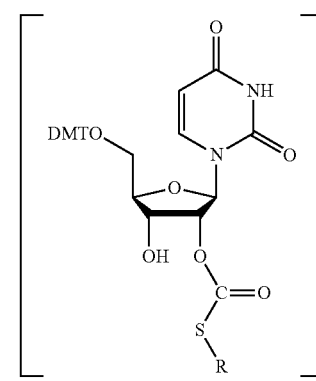

No isolation of DMT compound

R = —CH₃, —CH₂CH₃, —CH(CH₃)₂, -tert-Butyl

NMI (N-Methyl Imidazole)
HF/Pyridine is a complex made of HF/Pyridine:70/30: w/w
Depending on R, the tritylation reaction can be slow and NMI or DMAP can be added in a small amount (0.1 eq) to accelerate the reaction.

Scheme 5.
5′-O-DMT-2′-O-hydrocarbylthiocarbonyl-3′-O-[methyl-(N,N-diisopropyl)]-phosphoramidite-N⁴-phenylcoxycarbonyl Cytidine Monomer

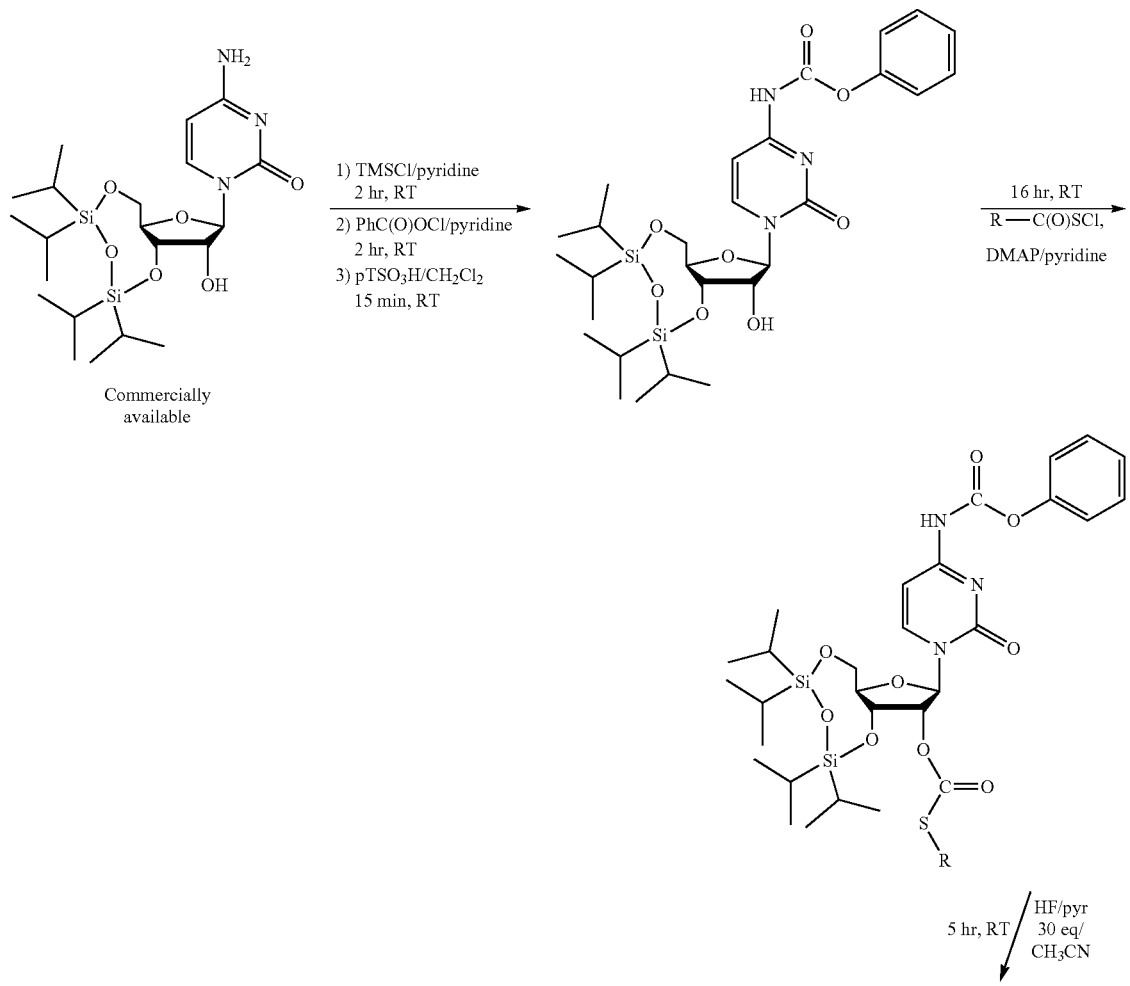

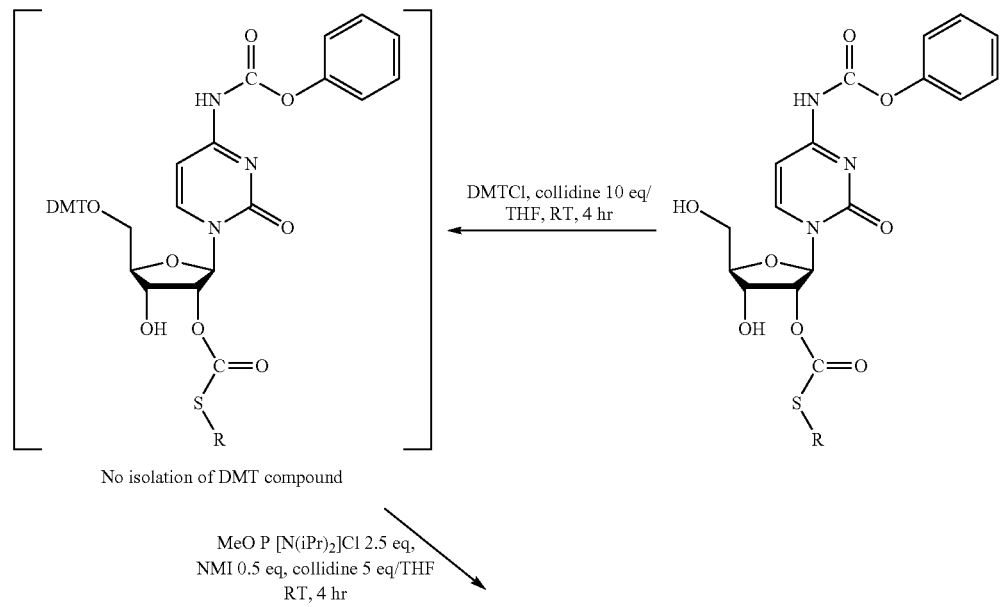

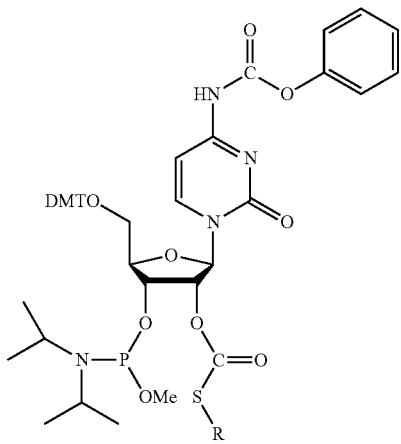

R = —CH₃, —CH₂CH₃, —CH₂(CH₃)₂, -tert-Butyl

TMSCl=Trimethylsilyl chloride
PhC(O)OCl=Phenyl chloroformate
pTSO₃H=para-toluene sulfonic acid
R—C(O)SCl=ThioChloroformate (ethylthiochloroformate)
DMAP—4,4'-Dimethylamino pyridine
HF/Pyridine is a complex made of HF/Pyridine:70/30: w/w
Collidine is 2,4,6-collidine NMI—N-methylimidazole Scheme 6. Synthesis of 5'-O-DMT-2'-O-hydrocarbylthiocarbonyl-3'-O-[methyl-(N,N-diisopropyl)]-phosphoramidite-N⁶-phenyloxycarbonyl Adenosine and 5'-O-DMT-2'-O-hydrocarbylthiocarbonate-3'-O-[methyl-(N,N-diisopropyl)]-phosphoramidite-N⁴-phenyloxycarbonyl Guanidine

27
A) Protection of the Exocyclic Amine
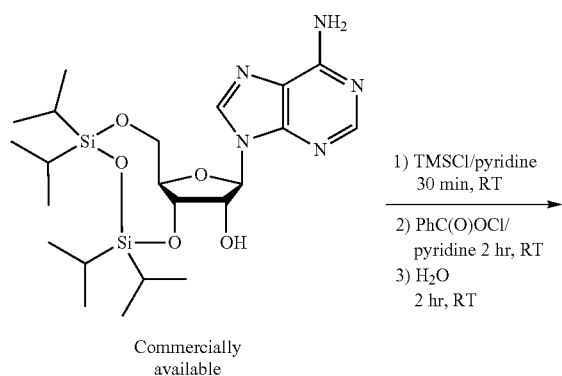
28
-continued
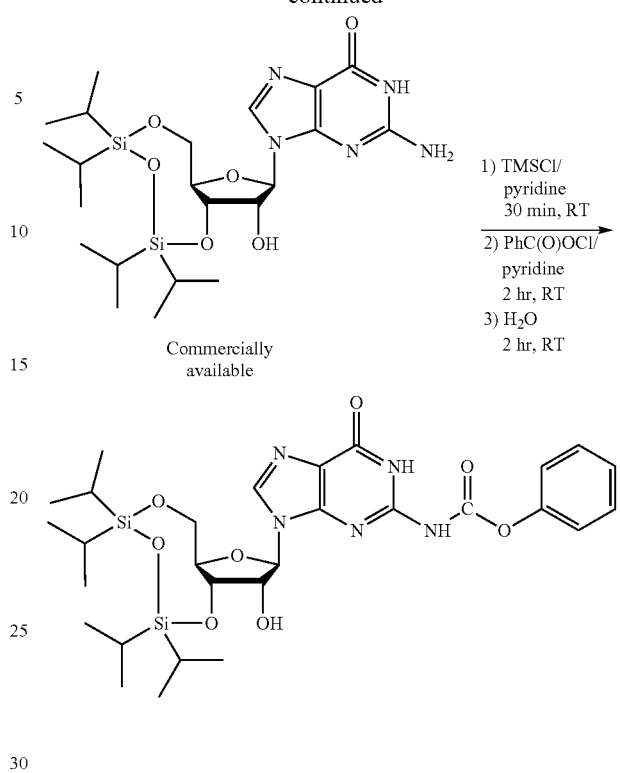
B) Selective Protection of the 2'-hydroxyl and 3' phosphitylation
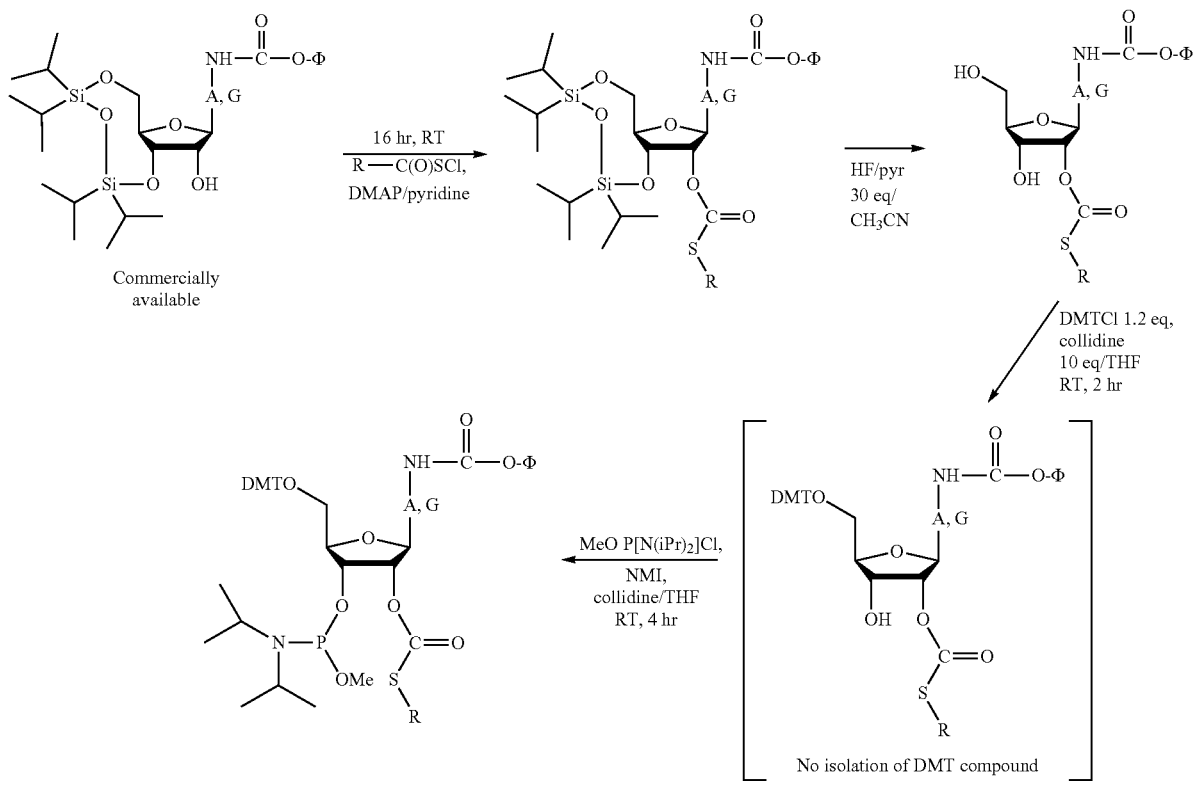
R = —CH₃, —CH₂CH₃, —CH(CH₃)₂, -tert-Butyl In order to synthesize 2'-O-t-butylthiocarbonate (BSC) uridine, one may use 5',3'-O-(Tetraisopropyldisiloxane-1,3-diyl) 2'-O-(p-nitrophenyl) carbonate protected uridine as a precursor, e.g., if other reagents such as tertbutyl chlorothioformate are not available. Sodium 2-methyl-2-propanethiolate is then used to displace the p-nitrophenyl carbonate as depicted below in Scheme 7:

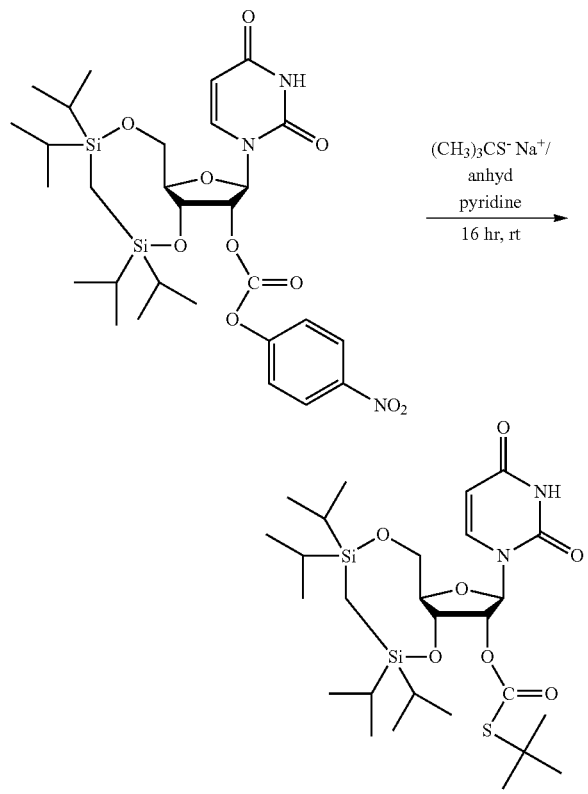

Thus, as a general approach to synthesize 2'-thiocarbonate where the corresponding chlorothioformate is not available, it is possible to use the corresponding mercaptan derivative and react it with phosgene to obtain the corresponding chlorothioformate or it is also possible to react the mercaptan with the 2' O-(p-nitrophenyl) carbonate protected nucleoside.

Thus, as a general approach to the synthesis of 2'-thionocarbamates the disiloxane protected nucleosides of formula (V) can be reacted with 1,1'-thiocarbonyldiimidazole in acetonitrile in the presence of a catalytic amount of 4-(dimethyl)aminopyridine. These reactions result in quantitative conversion of the protected nucleosides to the imidazole thionocarbamate of formula VI and crystalline products.

VI

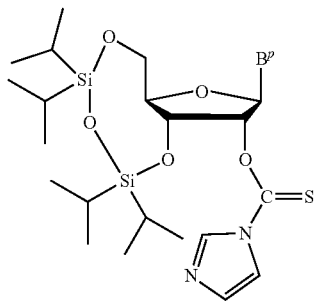

The reaction of the compound of formula with 1.1 equivalent of ammonia, primary, or secondary amines in acetonitrile with a catalytic amount of 4-(dimethyeaminopyridine results in quantitative conversion to the desired 2'-thionocarbamate. In the case of aniline or other weak nucleophiles, one equivalent of 4-(dimethyl)aminopyridine may be used to achieve complete conversion to the corresponding thionocarbamate. In the case of weak nucleophiles that are sterically constrained, such as dicyanoethylamine, the reaction may employ refluxing overnight in acetonitrile with one equivalent of 4-(dimethyl)aminopyridine and the resulting product may be isolated in 70% yield. These products may be converted to active RNA synthesis monomers by first removing the 5',3'-tetraisopropyldisiloxane protecting group with 15 eq to 40 eq of HF/pyridine to produce the 2'-O-thionocarbamate-ribonucleoside intermediate. This intermediate may then be reacted with DMTrCl with 5 eq to 10 eq of collidine NMI to produce a 5'-O-DMT-2'-O-thionocarbamate-ribonucleoside derivative; that product may then be reacted with a phosphytilating reagent selected from: CNEO-P(Cl)—N(iPr)$_2$ or (diisopropyl)aminomethoxychlorophosphine to produce a 5'-O-DMT-2'-O-thionocarbamate-ribonucleoside-3'-O-methyl(- or cyanoethyl) phosphoramidite Nucleic Acid Synthesis Using Thiocarbon Protecting Groups The nucleoside monomers of this invention can be used to synthesize nucleic acids, e.g., ribonucleic acids, efficiently. The synthesis can be performed in either direction: from 3' to 5' or from 5' to 3'. For example, in the 3' to 5' direction, a first nucleoside monomer with a 5'-OH and a 3'-protecting group is coupled with a second nucleoside monomer having a 3'-phosphoramidite and a 5'-protecting group. The first nucleoside monomer is optionally bound to a solid support. Alternatively, the synthesis can be performed in solution. After the coupling step, in which the 5'-OH and the 3'-phosphoramidite condense to form a phosphite triester linkage and result in a dinucleotide, the dinucleotide is capped/oxidized, and the 5'-protecting group is removed (deprotection). The dinucleotide is then ready for coupling with another nucleoside monomer having a 3'-phosphoramidite and a 5'-protecting group. These steps are repeated until the nucleic acid reaches the desired length and/or sequence, and the 2'-protecting group can be removed as described above. In some embodiments of this invention, the nucleoside monomers contain bases that are protected by the same protecting group as the 2'-OH, thus both of these protecting groups can be removed at the same time.

Thiocarbon protections on the 2'-hydroxyl and optionally on the base allow synthesis of long sequences of RNA which were not possible to synthesize chemically before, because of the ease and efficiency of removing these protecting groups. The nucleic acids synthesized by embodiments of the methods disclosed herein may be as long as 20, 25, 30, 35, 40, 45, 50, 55, 60, 65, 70, 75, 80, 85, 90, 95, 100, 105, 110, 115, 120, 125, 130, 135, 140, 145 or 150 nucleotides in length or longer. Furthermore, a nucleic acid synthesized according to this invention can be combined with another nucleic acid to form longer nucleic acids. For example, a nucleic acid of 70 bases can be coupled with another nucleic acid of 70 bases by chemical ligation. As another example, two nucleic acids can be ligated with an RNA ligase. In this case, the 2'-protecting groups should be removed before ligation.

The synthetic methods of the invention may be conducted on a solid support having a surface to which chemical entities may bind. In some embodiments, multiple oligonucleotides being synthesized are attached, directly or indirectly, to the same solid support and may form part of an array. An "array" is a collection of separate molecules of known monomeric sequence each arranged in a spatially defined and a physically addressable manner, such that the location of each sequence is known. The number of molecules, or "features," that can be contained on an array will largely be determined by the surface area of the substrate, the size of a feature and the spacing between features, wherein the array surface may or may not comprise a local background region represented by non-feature area. Arrays can have densities of up to several hundred thousand or more features per $cm^2$, such as 2,500 to 200,000 features/$cm^2$. The features may or may not be covalently bonded to the substrate. An "array," or "chemical array" used interchangeably includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

In some other embodiments, oligonucleotides being synthesized are attached to a bead directly or indirectly. Suitable solid supports may have a variety of forms and compositions and derive from naturally occurring materials, naturally occurring materials that have been synthetically modified, or synthetic materials. Examples of suitable support materials include, but are not limited to, silicas, teflons, glasses, polysaccharides such as agarose (e.g., Sepharose® from Pharmacia) and dextran (e.g., Sephadex® and Sephacyl®, also from Pharmacia), polyacrylamides, polystyrenes, polyvinyl alcohols, copolymers of hydroxyethyl methacrylate and methyl methacrylate, and the like. The initial monomer of the oligonucleotide to be synthesized on the substrate surface is typically bound to a linking moiety which is in turn bound to a surface hydrophilic group, e.g., a surface hydroxyl moiety present on a silica substrate. In some embodiments, a universal linker is used. In some other embodiments, the initial monomer is reacted directly with, e.g., a surface hydroxyl moiety. Alternatively, oligonucleotides can be synthesized first according to the present invention, and attached to a solid substrate post-synthesis by any method known in the art. Thus, the present invention can be used to prepare arrays of oligonucleotides wherein the oligonucleotides are either synthesized on the array, or attached to the array substrate post-synthesis.

With the efficiency and ease of the present method, oligonucleotide synthesis can be performed in small or large scales. The quantity of oligonucleotide made in one complete run of the present method (in one container) can thus be less than a microgram, or in micrograms, tens of micrograms, hundreds of micrograms, grams, tens of grams, hundreds of grams, or even kilograms.

In certain embodiments of the present invention, the doubly protected monomers of the invention are used in the synthesis of ribonucleic acids, for example, in solid-phase or solution-phase synthesis of ribonucleic acids. Synthesis in accordance with the invention can be performed in either direction: e.g., from 3' to 5' or from 5' to 3'. For example, in the 3' to 5' direction, a first nucleoside monomer with a 5'-OH and a 3' protecting group is coupled with a second nucleoside monomer having a 3' phosphoramidite group and a 5' protecting group. The first nucleoside monomer is optionally bound to a solid support, e.g., where synthesis is carried out using solid phase synthesis protocols. Alternatively, this synthesis can be performed in solution.

After the coupling step, in which the 5'-OH and the 3'-phosphoramidite moieties condense to form a phosphite triester linkage and result in a dinucleotide, the dinucleotide is capped/oxidized, and the 5'-protecting group is removed (deprotection). The dinucleotide is then ready for coupling with another nucleoside monomer having a 3'-phosphoramidite group and a 5'-protecting group. These steps are repeated until the oligonucleotide reaches the desired length and/or sequence.

As such, aspects of the invention include methods of synthesizing nucleic acids that include the steps of providing a nucleoside residue having an unprotected hydroxyl group and a nucleoside monomer with a 2' thiocarbonate protecting group; and contacting the nucleoside residue and the 2' thiocarbonate protected nucleoside monomer under conditions sufficient to covalently bond the 2' thiocarbonate protected nucleoside monomer to the nucleoside residue to produce a nucleic acid. The above sections describe a single monomer addition step of the synthesis protocol, where the above process is reiterated with additional monomers as desired to produce a polymer of desired length and sequence. As reviewed above, between each monomer addition step, the process may include exposing the nucleic acid to an oxidizing and deprotecting agent.

In addition to the use in nucleoside monomers and oligonucleotide synthesis, the thiocarbon protecting groups can be used advantageously in other molecules in which it is desired to protect a 1, 2 or 1,3-diol moiety while minimizing cyclic carbonate formation. For example, thiocarbon protecting groups can also be used for the regioselective deprotection of an alcohol that has a siloxane protecting group other than TIPS, such as TBDMS, trimethylsilyl, triethylsilyl, and tri-isopropylsilyl, while not removing the protecting group. The alcohol being protected can be a molecule other than a nucleoside monomer or oligonucleotide.

RNA Deprotection

A variety of different deprotection protocols may be employed. The deprotection/oxidation reaction essentially may be conducted under the reported conditions used for the synthesis of polynucleotides as described in, e.g. U.S. Pat. No. 6,222,030 to Dellinger et al.; U.S. Pat. No. 7,135,565 to Dellinger et al.; Seio et al. (2001) Tetrahedron Lett. 42 (49): 8657-8660. As will be appreciated by those of ordinary skill in the art, given the disclosure herein, the conditions for the deprotection/oxidation step may vary depending on the nature of the protecting groups used. In order to be compatible with the protecting group on the 2'-O as described herein, the conditions for the simultaneous deprotection and oxidation step (i.e. required conditions for release of the 3'- or 5'-hydroxyl protecting group) should be selected such that the protecting group on each of the 2'-O site(s) of the nascent polynucleotide remains stably attached to the nascent polynucleotide under conditions which provide for the deprotection of the 3'- or 5'-hydroxyl protecting group. In some embodiments, conditions for the deprotection/oxidation reaction include a pH in the neutral to moderately basic range. In further embodiments, the pH of the deprotection/oxidation reaction is at least about 6.0, including a pH of at least about 6.5, further including a pH of at least about 7.0, still further including a pH of at least about 7.5. In additional embodiments, the pH is less than about 12, including a pH of less than about 11, further including a pH of less than about 10.5, still further including a pH of less than about 10.

Certain embodiments utilize a combined deprotection/oxidation reagent which may be selected to provide particularly advantageous synthesis conditions and characteristics, as are described herein. In some embodiments, the combined deprotection/oxidation step provides for contacting the elongating polynucleotide chain with an alpha effect nucleophile under neutral or mildly basic aqueous conditions to remove the reactive site hydroxyl protecting group (e.g., the 5' terminus for synthesis in the 3' to 5' direction, or the 3' terminus for synthesis in the 5' to 3' direction) where that protecting group is labile under nucleophilic attack. The alpha effect nucleophile also oxidizes the newly formed phosphite triester linkage to give the phosphotriester linkage.

The deprotection/oxidation reagent may be any compound or mixture of compounds that is compatible with the synthesis of polynucleotides and has the properties discussed herein. In some embodiments, the deprotection/oxidation reagent includes a concentration of an oxidant that is high enough to rapidly oxidize the newly formed phosphite internucleotide linkage. In certain embodiments, this concentration is at least 0.1% vol/vol, including at least 0.5% vol/vol, further including at least about 1.0% vol/vol, still further including at least about 3.0% vol/vol. In these embodiments, the concentration of the oxidant should be low enough to avoid appreciable (e.g. less than 1% per iteration of the synthesis cycle) amounts of oxidative destruction of the nucleobases or protected nucleobases. In certain embodiments, this concentration is less than 10% vol/vol, including less than 9% vol/vol, further including less than 7% vol/vol.

In some embodiments, the deprotection/oxidation reagent provides a source of a peroxyanion at neutral to mildly basic pH in the reaction mixture during the deprotection/oxidation reaction. The concentration of the peroxyanion will be related to the acid dissociation constant of the hydroperoxide species at equilibrium. The concentration of peroxyanion is in the range 0.01% to 99% of the total hydroperoxide concentration (i.e., sum of all hydroperoxide species, e.g., protonated and unprotonated forms), including the range 0.05% to 90% of the total hydroperoxide concentration, further including the range 0.1% to 50% of the total hydroperoxide concentration, still further including the range of 1.0% to 30% of the total hydroperoxide concentration.

In certain embodiments, the nucleophilic deprotection reagent that exhibits an alpha effect is a peroxide or a mixture of peroxides. In some embodiments, the pH at which the deprotection/oxidation reaction is conducted is generally in the range of about three pH units below the pKa of the nucleophilic deprotection reagent (that is, the pKa for formation of the corresponding peroxy anion) up to about three pH units above the pKa of the nucleophilic deprotection reagent. In further embodiments, the pH of the deprotection/oxidation reaction is in the range of about one pH unit below the pKa of the nucleophilic deprotection reagent up to about pH 11. In other embodiments, the pH will be the range that allows a high enough concentration of the peroxy anion to form, e.g., from about the pKa of the peroxide up to a pH of about 11. The peroxide may be either inorganic or organic. Suitable inorganic peroxides include those of the formula M+OOH—, where M+ is any counter ion, including for example H+, Li+, Na+, K+, Rb+, Cs+, or the like. In some embodiments, lithium peroxide or hydrogen peroxide and alkaline stabilized forms thereof are used. Suitable organic peroxides include those of the formula ROOH, where R is selected from the group consisting of alkyl, aryl, substituted alkyl, substituted aryl, and modified alkyl. More particularly, the organic peroxide will have the structure of Formula (VI), Formula (VII), or Formula (VIII):

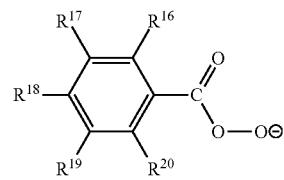
VI

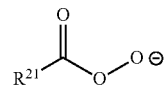
VII

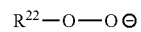
VIII in which $R^{13}$ through $R^{19}$ are independently selected from the group consisting of hydrido, hydrocarbyl, substituted hydrocarbyl, aryl, and substituted aryl. In some embodiments, the alpha-effect nucleophile is t-butyl-hydroperoxide or metachloroperoxybenzoic acid. For example, the m-chloroperoxybenzoic acid (mCPBA) peroxy anion has been found to be useful for removal of protecting groups on the reactive site hydroxyl.

As indicated in the above, the steps of the synthesis cycle can include a coupling step and a simultaneous deprotection/oxidation step. In an embodiment of a method of synthesizing a polynucleotide in accordance with the present invention, these steps of the synthesis cycle may be repeated multiple times to produce a polynucleotide having the desired sequence.

In some embodiments, after the series of coupling and deprotection/oxidation steps results in an oligonucleotide having a desired sequence and length, the resulting oligonucleotide undergoes a post-synthesis deprotection step, in which protected sites on the heterocycles and/or the 2'-oxygens are deprotected. For example, protecting groups bound to the heterocycles and/or the 2'-sites of the nucleotide subunits of the resulting nucleotide may be removed to provide a deprotected oligonucleotide.

Some embodiments in accordance with the present invention provide methods and compositions for post-synthesis RNA deprotection, particularly compositions used to remove the 2'-benzodithiolane (BDT) groups such as HBF$_4$/TEMED at pH 3.8 as depicted in Scheme 8 below, wherein Ac represents a thiocarbon protecting group.

SCHEME 8

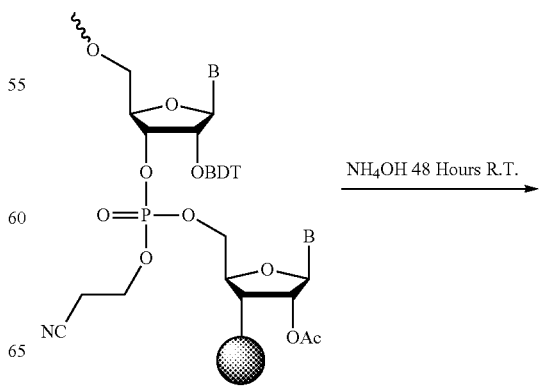

NH$_4$OH 48 Hours R.T.

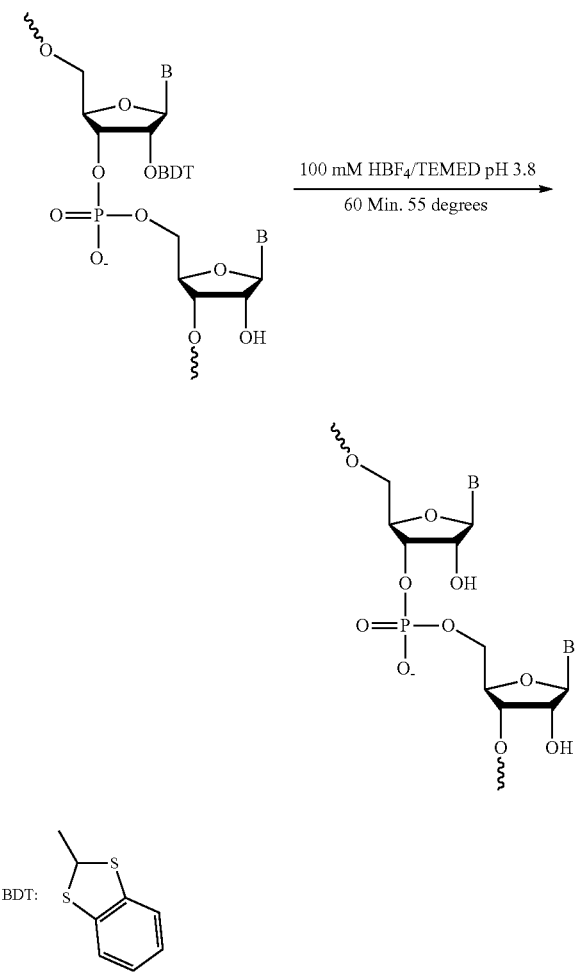

As summarized above, a variety of protocols may be employed to remove the thiocarbon protecting groups from the synthesized polymer. In certain embodiments, fluoride ion containing solutions such as tetraalkylammonium fluoride salts like tetramethylammonium, tetraethylammonium or tetrabutylammonium are used to directly remove the protecting group. These salts may be dissolved in an aprotic polar solvent such as tehrahydrofuran, dioxane, or acetonitrile at a suitable concentration, e.g., a concentration of 1 molar. Solutions containing no acidic protons such as TBAF (tetrabutylamonium fluoride) work significantly better than hydrofluoric acid salts such as HF/TEMED or HF/TEA (triethylamine) at the deprotection of thiocarbonate, dithiocarbonate or thionocarbonate protecting groups from the 2'-hydroxyl. Deprotection of carbamates with TBAF has been reported recently (Jacquemard et al., Tetrahedron 60: 10039-47 (2004)). The efficiency of non-hydrofluoric acid containing fluoride ion salts such as TBAF in desilylation reactions has been previously demonstrated to be greatly improved by keeping the water content below 5% (Hogrefe et al, Nucleic Acids Research 21: 479-41 (1993)). The deprotection efficiencies of thiocarbonate, dithiocarbonate or thionocarbonate were also shown to be greatly enhanced by lowering the water content of the solution. These solutions can contain from 2% to 10% water (v:v), such as from 2% to 6% of water and including from 2% to 4% of water. However, lowering the water content in TBAF solutions by adding molecular sieves to these solutions can also result in the decomposition of the TBAF through a chemical reaction called a Hoffmann elimination at room temperature (Cox et. al. J. Org. Chem.: 49 3216-19 (1984)). The resulting degradation products produce the acidic salt tetrabutylammonium-hydrobifluoride ($HF_2TBA$ or bifluoride). Solutions of TBAF that are absent of bifluoride were shown to deprotect thiocarbonate, dithiocarbonate or thionocarbonate protecting groups much more rapidly and efficiently than solutions containing bifluoride. It is possible to determine the bifluoride content using $^{19}F$ fluorine NMR (Sun and DiMagno, J. AM. Chem. Soc.:127, 2050-51 (2005)) and eliminate it by storage of the TBAF solution over a strong base such as for example but not limited to sodium hydroxide or potassium carbonate, or by addition of tertiary amines such as for example, but not limited to, triethylamine or diisopropylethylamine, or tetraalkylammoinum hydroxides, such as tertrabutylammonium hydroxide (TBAOH) and the like. Solutions of TBAF used for the deprotection of thiocarbonate, dithiocarbonate, thionocarbamate, or thionocarbonate protecting groups on the 2'-hydroxyl contain, in certain embodiments, less than 30%, such as less than 5% and in certain embodiments less than 2% of biflouirde In certain embodiments, TBAOH itself acts as a reagent capable of deprotecting 2'-thiocarbonate, dithiocarbonate or thionocarbonate protecting groups. Indeed, it had been found that TBAF solutions treated in excess with tetraalkylammoinum hydroxides can be highly active in the deprotection of these new 2'-protecting groups even in the presence of greater than 10% water content in the solution. However, if TBAOH is added to a solution of TBAF containing bifluoride in a molar equivalent to the bifluoride, then in order to be highly active at the deprotection of thiocarbonate, dithiocarbonate or thionocarbonate protecting groups, the resulting water content of the deprotection solution should be low. These TBAF/TBAOH solutions can contain from 2% to 10% water, such as from 2% to 6% water and including from 2% to 4% water. If TBAOH is added to a TBAF solution in excess of the bifluoride content, then the resulting solution can be highly active at the deprotection of thiocarbonate, dithiocarbonate or thionocarbonate, or thionocarbamate protecting groups regardless of the water content. Thus to summarize:

If $[TBAOH] \sim [HHF_2TBA]$, then $[H_2O]$ in TBAF/TBAOH<5%

If $[TBAOH] > [HF_2TBA]$, then $[H_2O]$ in TBAF/TBAOH<30%

However there is a limit on both the excess of tetraalkylammonium hydroxides and water that can be used in the deprotection of 2'-hydroxyl groups on RNA. If the water content of the polar aprotic solvent deprotection solution gets too high in the presence of excess tetraalkylammonium hydroxides, then the resulting RNA products can be degraded by a general base mechanism that is well known in the art. In certain embodiments, the water content of these solutions is 30% or less, such as 10% or less and including 5% or less. Similarly, if the concentration of tetraalkylammonium hydroxides becomes too high in the polar aprotic solvent solution the RNA products can also be degraded. The tetraalkylammonium hydroxides should be dissolved at a concentration of 30% or less, such as 25% or less and including 20% or less. TBAOH alone, i.e., without TBAF, can also be diluted in polar aprotic solvents to deprotect thiocarbonate, dithiocarbonate, thionocarbonate, or thionocarbamate protecting groups from the 2'-hydroxyl. However, the deprotection rates are slow in comparison to TBAF solutions containing the same dilute concentration of TBAOH. Exposure of the RNA to a dilute TBAOH solution resulted in partial RNA degradation after several days and upon complete deprotection of the 2'-thiocarbonate protecting groups. A 1 molar TBAF solution containing an excess of TBAOH ie: [TBAOH]>[$HF_2TBA$] at the same dilute TBAOH concentration gave complete deprotection of the RNA in a few hours. Moreover, several days exposure of the RNA to this TBAOH/TBAF solution did not yield to any observable degradation of the desired RNA products. Thus, the TBAF solution appears to have a role in both accelerating the deprotection reaction and protecting the RNA backbone from degradation. We further identified that other tetraalkylammonium salts such as tetrabutylammonium bromide, and tetrabutylammonium acetate instead of TBAF dissolved at 1 molar in polar aprotic solvents such as, by way of illustration but not limited to, dioxane, THF and acetonitrile and with the addition of TBAOH can both accelerate the deprotection of thiocarbonate, dithiocarbonate, thionocarbonate, or thionocarbamate protecting groups while protecting the RNA backbone from degradation. These tetraalkylammonium salts should be dissolved in the polar aprotic solvent solution at a concentration of 0.1 molar or greater, such as a concentration 0.25 molar or greater and including a concentration of 0.5 molar or greater.

Embodiments of the present invention comprise compositions for solutions used to deprotect a RNA comprising 2'-O-thiocarbonyl, -dithiocarbonyl, -thionocarbonyl, or 2'-O-thionocarbamate protecting groups. Such compositions include: TBAF with controlled amount of a strong base such as but not limited to TBAOH, NaOH, potassium carbonate, tetraalkylammonium hydroxides and inorganic hydroxides such as but not limited to LiOH, CsOH and a controlled amount of water provided that when [TBAOH]~[$HF_2TBA$], then TBAF/TBAOH solutions can tolerate from 2% to 10% water, such as from 2% to 6% water and including from 2% to 4% of water; and when [TBAOH]>[$HF_2TBA$], then TBAF/TBAOH solutions can contain from 30% or less of water, such as 10% or less of water and including 5% or less of water.

Other compositions comprise tetraalkylammonium salts such as tetrabutylammonium bromide (TBAB), and tetrabutylammonium acetate(TBAA) dissolved at 1 molar concentration in polar aprotic solvents such as, by way of illustration but not limited to, dioxane, THF and acetonitrile. Addition of a strong base soluble in polar aprotic solvent such as, but not limited to, TBAOH, tetraalkylammonium hydroxides and inorganic hydroxides such as but not limited to LiOH, CsOH to these solutions, accelerate the deprotection of thiocarbonate, dithiocarbonate, thionocarbonate, or thionocarbamate protecting groups while preserving the RNA backbone from degradation.

A further embodiment of this invention comprises a composition as recited herein: a RNA deprotection solution comprising 10% to 30% (v/v) of a 1M solution of a strong base selected from tetraalkylammonium hydroxide and inorganic hydroxides dissolved in MeOH or $H_2O$ added to 1M solution of a tetrabutylammonium salt selected from TBAF, TBAB and TBAA dissolved in a polar aprotic solvent selected from THF, dioxane, and acetonitrile with a final content of water in said RNA deprotection solution less than 20% (v/v), more preferably less than 10%, most preferably less than 5%.

In a further embodiment thionocarbonate and thionocarbamates can be deprotected using amines under conditions that do not result in the destruction of the RNA chain.

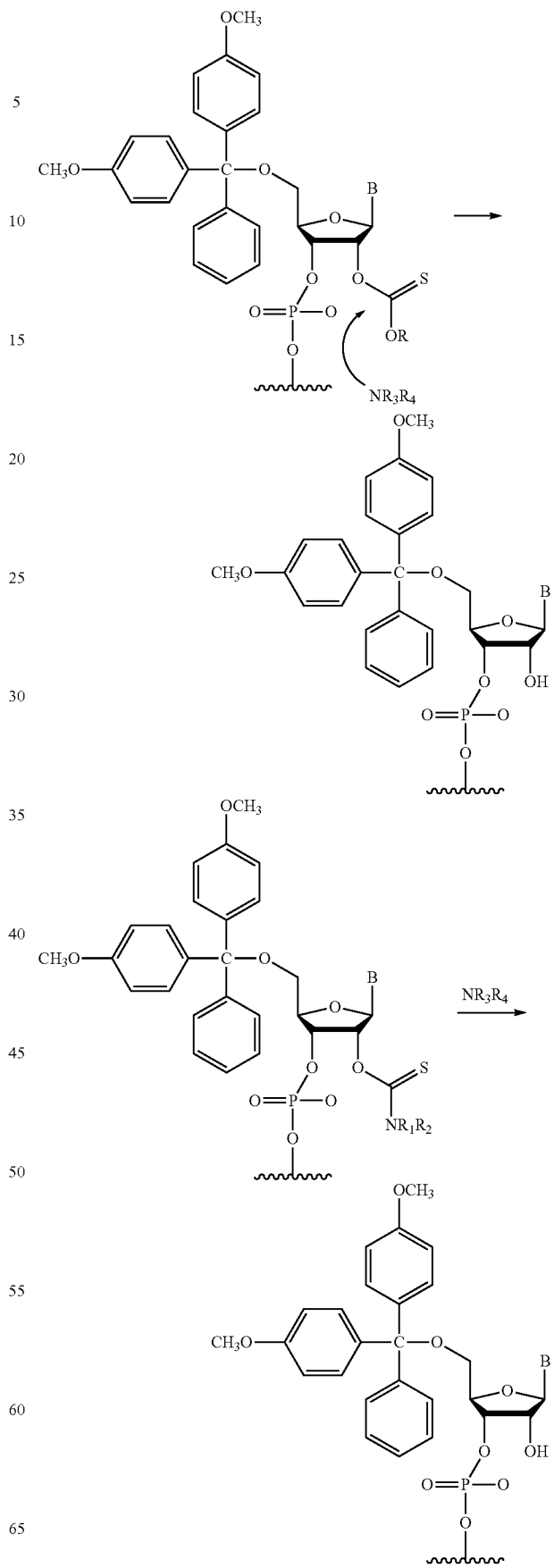

As is well known, RNA undergoes cleavage and degradation under basic conditions, via a transesterification reaction involving the 2-hydroxyl group. [Journal of Organic Chemistry, 1991. 56 (18): p. 5396-5401; Journal of the American Chemical Society, 1999. 121 (23): p. 5364-5372; Chemical Reviews, 1998. 98 (3): p. 961-990.]. "The pKa of a 2'-hydroxyl of RNA in aqueous solution can vary depending on salt concentration and base sequence, but is typically around 13[Journal of the American Chemical Society, 2001. 123 (12): p. 2893-2894.; J Org Chem, 2003. 68 (5): p. 1906-10]. The pKa of (protonated) ammonia is about 9.2, which means that a concentrated aqueous ammonium hydroxide solution typically used for removing protecting groups from synthetically prepared oligonucleotides has a pH of greater than 12. At these high pHs, a significant amount of the 2'-hydroxyl is deprotonated, and the well known base catalyzed transesterification reaction results in backbone cleavage.

ties of organic molecules in dipolar aprotic solvents, particularly in dimethylsulfoxide, have been widely studied. Acetic acid, which has a pKa of 4.7 in water, is a much weaker acid in DMSO, with a pKa of 12.3. Methanol, which has a pKa in water of about 15, has a pKa of ~28 in DMSO. In general, for a neutral compound ionizing to a charged anionic species (such as a hydroxyl group ionizing to an alkoxy anion), decreasing the dielectric of a solvent in general results in a decrease in the acid equilibrium constant (increase in pKa) for the following equilibrium:

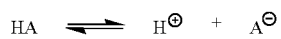

Thus the pKa of phenol is about 10 in water (dielectric constant=78), while in DMSO (dielectric constant=47) the

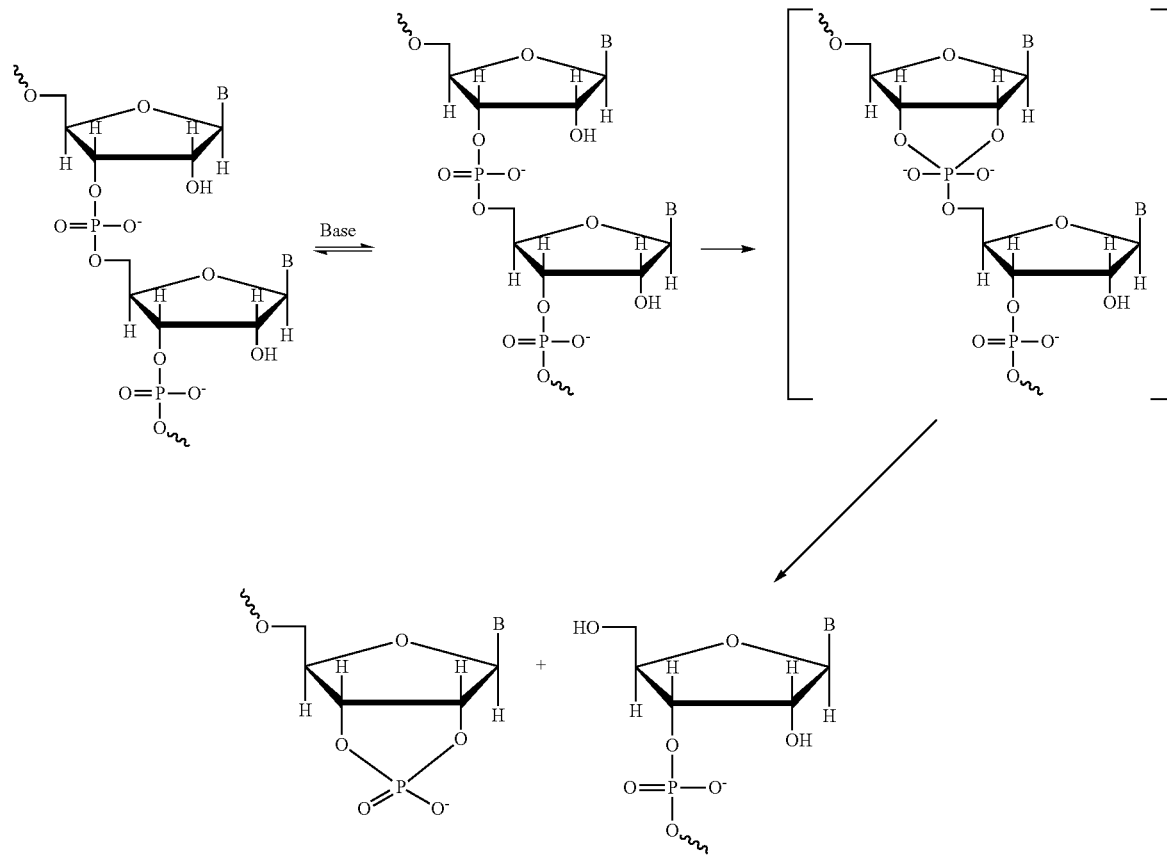

Stronger bases such as methylamine (pKa 10.6) or triethylamine (pKa 10.6) will, under typical aqueous conditions, promote RNA backbone cleavage even more readily than ammonia. Oligonucleotide synthesis typically uses protecting groups on the bases that are removed with aqueous solutions of amine bases such as ammonia or methylamine. In the case of RNA, it is desirable that the 2'-hydroxyl protection be intact during this procedure to avoid the base catalyzed backbone cleavage.

However, the pKas previously described for amine bases and the 2'-hydroxyls are for aqueous conditions. It is known that the ionization constants of weak acids and bases can be substantially altered in the presence of organic solvents [J Biochem Biophys Methods, 1999. 38 (2): p. 123-37]. AcidipKa is about 16, and in acetonitrile (dielectric constant=36) the pka is approximately 27[J. Phys. Chem., 1965. 69 (9): p. 3193-3196; J. Am. Chem. Soc., 1968. 90 (1): p. 23-28; Journal of Organic Chemistry, 2006. 71 (7): p. 2829-2838], a change of 16 orders of magnitude. Hence in acetonitrile phenol is a very weak acid (the corresponding anion is a very strong base). It should be recognized that the dielectric strength of a solvent is not the only variable that can affect the pKa of a compound. Solvent basicity, polarity, hydrogen bonding, and other specific and non-specific interactions can affect the salvation capability of a solvent and can have a significant effect on the pKa of dissolved solutes.

For a charged compound dissociating to a neutral compound, such as the dissociation of a protonated amine, decreasing the dielectric of a solvent in general results in only relatively small changes in pKa.

Thus the pKa of (protonated) triethylamine in water is about 11, while in DMSO the pKa is about 9, and in acetonitrile the pKa is about 18. In acetonitrile, triethylamine is a somewhat stronger base than in water (delta pKa going from water to acetonitrile is ~7) while in DMSO it is actually a weaker base.

As a result RNA may be 2'-deprotected using amines in organic solvent. The base catalyzed mechanism for the degradation of RNA depends on the ability of the base to deprotonate the hydroxyl to a sufficient extent such that the cyclization and cleavage reaction can occur at a significant rate. In the case of aqueous solutions of amine bases deprotonating the 2'-hydroxyl, there is a difference of about 4 pKa units, which is close enough so that concentrated solutions of amine bases can significantly deprotonate the hydroxyl. However, when organic solvents are used, the pKa of the 2'-hydroxyl is increased significantly more than that of the amine base. In solvents such as acetonitrile, ordinary amines such as ammonia or methylamine are not strong enough bases to deprotonate the 2'-hydroxyl. In fact, amine bases in acetonitrile are not strong enough to even deprotonate phenol. Even though ammonia becomes a stronger base in acetonitrile (pKa of conjugate acid increases from 9.2 to 16.5 when going from water to acetonitrile, a delta pKa of ~7)[J. Am. Chem. Soc., 1968. 90 (1): p. 23-28.], phenol becomes a relatively much weaker acid, with the pKa increasing from about 10 to 27 (delta pKa ~17). The acid base pair of phenol and ammonia, which in water have a pka difference of less than one pKa unit, in acetonitrile have a pKa difference of about 10 pKa units. The actual pKa in acetonitrile of an aliphatic hydroxyl such as the 2'-hydroxyl of RNA is increased to a point where it is difficult to measure (calculation gives a pKa of about 35). In acetonitrile and many other organic solvents, the solvent mediated equilibrium between amine bases and aliphatic alcohols are in favor of the two neutral species by over 10 orders of magnitude, and degradation of RNA will not occur at an appreciable rate.

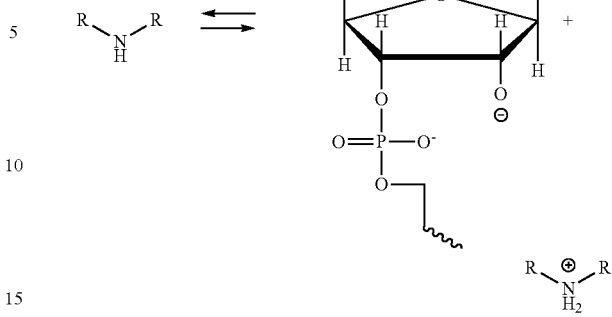

Exposing RNA to solutions of amine bases in organic solvents is thus a practical method of performing deprotection of RNA of both the exocyclic amine protecting groups as well as the 2-hydroxyl protecting group. The nucleophilicity of the amine bases, and hence the deprotection rate may even be enhanced in some organic solvents. The deprotection of the exocyclic amines and the 2'-hydroxyl can be performed simultaneously or sequentially. So long as the solutions do not contain enough water to significantly change the favorable pKa differential of the amines and hydroxyls, with the appropriate choice of protecting groups the degradation of the RNA will be very slow relative to the rate of deprotection.

In other embodiments it is desirable avoid the delivery of liquid solutions of reagents Amine bases such as ammonia or methylamine are gases at room temperature and pressure, and many other amine bases have significant vapor pressures under these conditions. They can be delivered either as a gas or as a component of a gas mixture in which the other components are an inert gas such as nitrogen or argon.

In the gas phase, basicities of amines and acidities of alcohols are also favorable for the stability of RNA. (The proton affinity of methylamine is about 214 kcal/mole, while the gas phase acidity of an alcohol (e.g. ethanol) is about 370 kcal/mole.) It should be realized however, that in the case of gas phase deliveries, any actual chemical reactions and equilibria are likely to be affected by the solid phase surface as well as adventitious and residual amounts of adsorbed solvents, including water. We have shown gas phase deliveries of amines to be an effective and sometimes preferred alternative to liquid phase deliveries. Alternatively, the amine bases can be delivered as a gas phase head space component from a solution of the amine dissolved in an organic solvent such as acetonitrile or dioxane. In this case the organic solvent vapors will be delivered as well, and under certain conditions may condense on the solid support. Another alternative is to add the amine neat, but to keep the liquid from directly contacting the bulk of the resin. This can be done for example, by adding the liquid to a vessel in which the resin is isolated from contact with the liquid by being in a separate container, or by adding a small amount of neat amine to a relatively larger amount of resin, thus only partially wetting the resin. Amines such as ammonia and methylamine are liquids only under pressure, and will spontaneously vaporize into the gas phase until (in a closed system) equilibrium is reached. Amines such as propylamine and butylamine are liquids with significant vapor pressures at room temperature, and will vaporize to a lesser degree. Another alternative delivery method is to add the amine in an organic solvent, but to keep the liquid solution from directly contacting the bulk of the resin. This will behave similarly to the neat amine delivery, but the resulting gas phase will also contain organic solvent vapor as determined by the vapor pressure of the solvent. As in the case of the neat amine delivery, this can be done in a closed system, and the amine and solvent will reach equilibrium with the gas phase, or a flow of inert gas or solvent vapor can be used to set up dynamic equilibrium in an open system.

In another embodiment there is a significant advantage to delivering solutions of amine bases in appropriate organic solvents or in the gas phase is that although the linker that covalently attaches the RNA to the surface of the solid support may be cleaved by bases such as ammonia, the RNA itself will not migrate off of the resin. In many organic solvents, for example isopropanol and acetonitrile, RNA is not appreciably soluble and/or will remain adsorbed or associated with the solid support. This is in contrast to treatment of a solid support with solutions of amines in water or DMSO, which cause cleavage of the linker and subsequent dissolution of the RNA into the water or DMSO solution.

In an embodiment thionocarbonates and thionocarbamates can be cleaved from the 2'-hydroxyl of synthetic RNA with amines not resulting in the destruction of the desired RNA.

In one embodiment the deprotection of the thionocarbamate protected 2'-hydroxyl is dependent on both the cleavage conditions and the structure of the thionocarbamate. In general, there are a number of possible mechanisms for the cleavage of thionocarbamates, shown below with ammonia used as example of a suitable amine base. The first mechanism shown, is for thionocarbamates that contain a secondary nitrogen, this shows the base catalyzed reaction which proceeds through the formation of an isothiocyanate [Canadian Journal of Chemistry-Revue Canadienne De Chimie, 2005. 83 (9): p. 1483-1491].

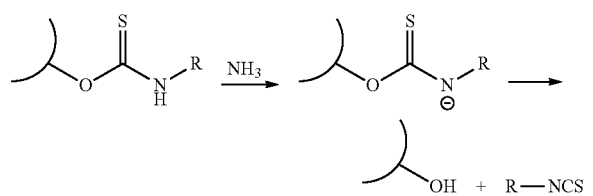

The second mechanism shows the reaction which involves attack of the ammonia on the carbonyl, with subsequent formation of the thionourea and alcohol [Bulletin of the Korean Chemical Society, 2006. 27 (1): p. 143-146].

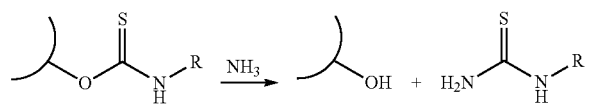

The pKa of the acidic hydrogen is estimated to be approximately 13.6, for R=ethyl [Canadian Journal of Chemistry-Revue Canadienne De Chimie, 2005. 83 (9): p. 1483-1491]. With relatively weak bases such as ammonia, the reaction to the anionic intermediate should be favored by R groups that can reduce the pKa of the nitrogen, stabilizing the negative charge on the nitrogen by either resonance or electron withdrawing inductive effects. However, R groups that stabilize the negative charge on the nitrogen will also slow down the decomposition of the anionic intermediate to the isothiocyanate. The competing mechanism with subsequent formation of the thionourea and alcohol should be favored by R groups that are electronegative enough to activate the carbonyl to nucleophilic attack, as well as low steric hinderance for the attacking nucleophile. In the case of tertiary nitrogen compound, there is no possibility for the competing isothiocyanate mechanism, and the compound can only under aminolysis by nucleophilic attack.

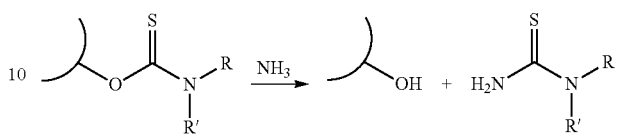

One possible initial product of the above mechanism [Bulletin of the Korean Chemical Society, 2006. 27 (1): p. 143-146] is the tetrahedral intermediate shown below.

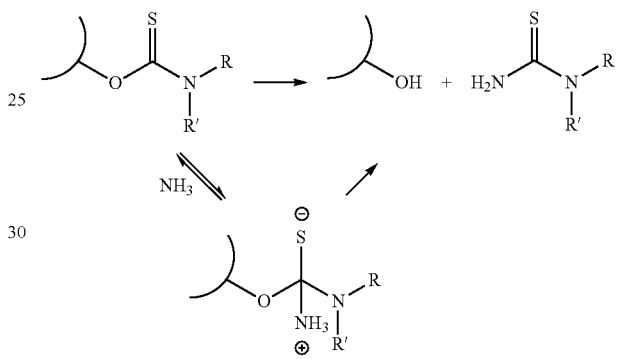

Such an intermediate suggests that one or more proton transfer steps occur before the expulsion of the 2'-hydroxyl and product formation occurs. The presence and reactivity of suitable proton donating species or the mediation of solvent may be important for the reaction to occur.

An alternative concerted 4-center transition state shown in below may also be possible, and has been shown to be operating with the aminolysis in acetonitrile of Aryl N-ethyl thionocarbamates [Journal of Organic Chemistry, 2005. 70 (14): p. 5624-5629].

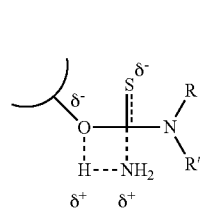

With the concerted mechanism, structural modifications of the protecting group and attacking nucleophile that stabilize the transition state are of primary importance.

In a further embodiment thiocarbonates can be converted to carbamates using amines. 2'-O-thiocarbonates can be converted to a stabile modified 2'-nucleotide or oligonucleotide by the displacement of the thiol using primary or secondary amines.

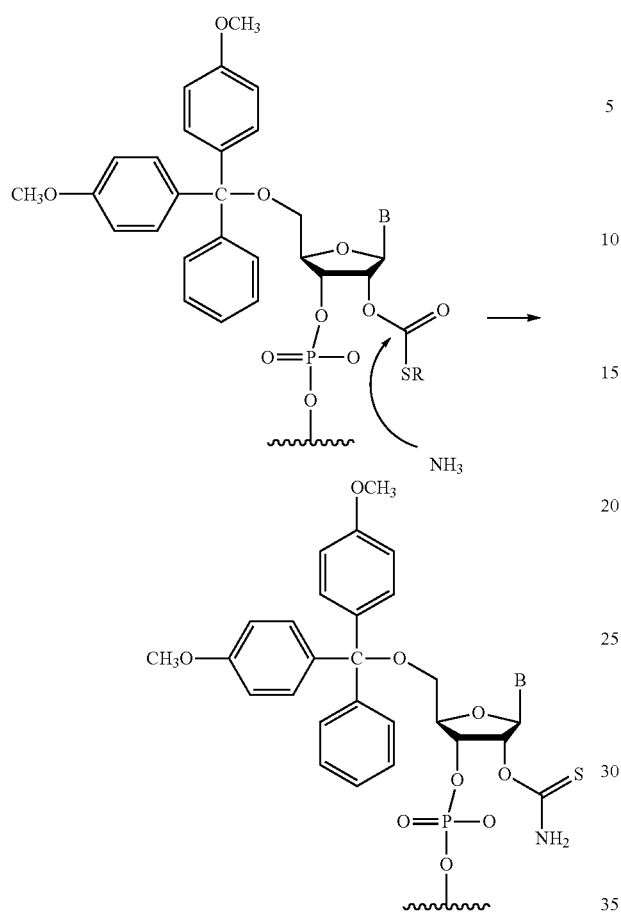

Nucleic Acid Products

Aspects of the invention further include the nucleic acid products of the methods of the invention. The nucleic acid products, e.g., RNA, of the methods of the invention may vary in size, ranging in certain embodiments from 2 to 200 or more monomeric units in length, such as 2 to 100 or more monomeric units in length, including 2 to 50 or more monomeric units in length. In certain embodiments, the size of the product nucleic acids ranges from 2 to 25 monomeric units in length, e.g., 15 to 25 monomeric units in length, such as 17 to 23 monomeric units in length, including 19, 20, 21, or 22 monomeric units in length.

In certain embodiments, nucleic acid products of the invention have the structure of Formula (VI):

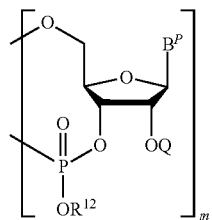

IX wherein:
B$^P$ is a protected or unprotected nitrogen-containing base, as defined above;
Q is a thiocarbon protecting group, e.g., as described above;
R$^{12}$ is selected from the group consisting of hydrogen, hydrocarbyls, substituted hydrocarbyls, aryls, and substituted aryls; and
m is an integer greater than 1.

In additional embodiments, the nucleic acid has a structure of Formulas IXa to IXc below:

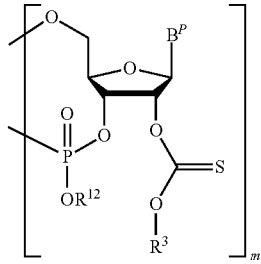

IXa

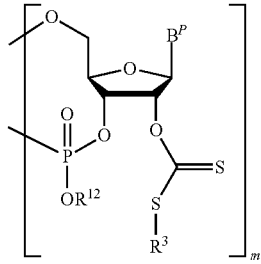

IXb

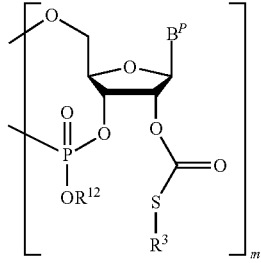

IXc

In additional embodiments, the nucleic acid has a structure of Formulas X below:

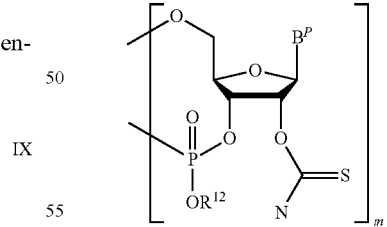

X

Wherein the variables in the above structure are as defined above.

Applications

The product nucleic acids produced in accordance with methods of the invention find use in a variety of applications, including research, diagnostic and therapeutic applications. For example, the product nucleic acids find use in research applications, e.g., as probes, primers, etc. With respect to diagnostic applications, the product nucleic acids may also find use as probes, primers, or other agents employed in diagnostic protocols. With respect to therapeutic applications, the product nucleic acids find use as any DNA, RNA or other nucleic acid therapeutic, such as antisense nucleic acids, in gene therapy applications, interfering RNA (i.e., iRNA or RNAi) applications, etc.

Depending on the application for which the nucleic acids are synthesized, the nucleic acids may or may not be modified in some manner following their synthesis. As such, in certain embodiments the product nucleic acids are not further modified following synthesis. In yet other embodiments, the nucleic acids are modified in some manner following their synthesis.

A variety of different modifications may be made to the product nucleic acids as desired. For example, where the product nucleic acids are interfering ribonucleic acids (iRNA), a variety of post-synthesis modifications may be desirable. The iRNA agent can be further modified so as to be attached to a ligand that is selected to improve stability, distribution or cellular uptake of the agent, e.g., cholesterol. The following post-synthesis modifications are described for convenience primarily in terms of iRNA embodiments. However, such modifications are readily adapted to DNA embodiments and the following description encompasses such embodiments as well.

The following modifications may be made before or after cleavage of the nucleic acid from the support, as desired.

Unmodified RNA refers to a molecule in which the components of the nucleic acid, namely sugars, bases, and phosphate moieties, are the same or essentially the same as that which occur in nature, e.g., as occur naturally in the human body. The art has referred to rare or unusual, but naturally occurring, RNAs as modified RNAs, see, e.g., Limbach et al, (1994) Nucleic Acids Res. 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, e.g., different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an mRNA agent. It may be desirable to modify one or both of the antisense and sense strands of an mRNA agent. As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. For example, a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into mRNA agents is their stabilization towards degradation in biological environments and the improvement of pharmacological properties, e.g., pharmacodynamic properties, which are further discussed below. Other suitable modifications to a sugar, base, or backbone of an iRNA agent are described in PCT Application No. PCT/US2004/01193, filed Jan. 16, 2004. An iRNA agent can include a non-naturally occurring base, such as the bases described in PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in PCT Application No. PCT/US2004/07070 filed on Mar. 8, 2004.

An iRNA agent can include ligand-conjugated monomer subunits and monomers for oligonucleotide synthesis. Exemplary monomers are described in U.S. application Ser. No. 10/916,185, filed on Aug. 10, 2004. An iRNA agent can have a ZXY structure, such as is described in PCT Application No. PCT/US2004/07070 filed on Mar. 8, 2004. An iRNA agent can be complexed with an amphipathic moiety. Exemplary amphipathic moieties for use with iRNA agents are described in PCT Application No. PCT/US2004/07070 filed on Mar. 8, 2004.

In another embodiment, the iRNA agent can be complexed to a delivery agent that features a modular complex. The complex can include a carrier agent linked to one or more of (such as two or more, including all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in PCT Application No. PCT/US2004/07070 filed on Mar. 8, 2004.

An iRNA agent can have enhanced resistance to nucleases. For increased nuclease resistance and/or binding affinity to the target, an iRNA agent, e.g., the sense and/or antisense strands of the iRNA agent, can include, for example, 2'-modified ribose units and/or phosphorothioate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEGs), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-AMINE and aminoalkoxy, O(CH$_2$)$_n$AMINE, (e.g., AMINE=NH$_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

One way to increase resistance is to identify cleavage sites and modify such sites to inhibit cleavage, as described in U.S. Application No. 60/559,917, filed on May 4, 2004. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3'C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of the oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of the oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In some embodiments, the nucleotide overhang includes 1 to 4 unpaired nucleotides, in other embodiments 2 to 3 unpaired nucleotides. In one embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In certain embodiments, the nucleotide overhang is on the 3'-end of the antisense strand. In one embodiment, the iRNA agent includes the motif 5'-CGC-3' on the 3'-end of the antisense strand, such that a 2-nucleotide overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization may be used only in terminal regions, and not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In certain embodiments, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nucleotide antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

The properties of an iRNA agent, including its pharmacological properties, can be influenced and tailored, for example, by the introduction of ligands, e.g. tethered ligands. A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Of interest are ligands, which are coupled, e.g., covalently, either directly or indirectly via an intervening tether, to the carrier. In certain embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In certain embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Ligands of interest can improve transport, hybridization, and specificity properties and may also improve nuclease resistance of the resultant natural or modified oligoribonucleotide, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., USA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. Also of interest are the lipid modifications described in WO/2005/023994; the disclosure of which is herein incorporated by reference.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, a helical cell-permeation agent. In some embodiments, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent may be an alpha-helical agent, which may have a lipophilic and a lipophobic phase.

In certain embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P (HO)(O)—O-5'); 5'-triphosphate ((HO)2(O)P—O—(HO) (O)P—O—P(HO)(O)—O-5'); 5'-guanosine cap (7-methylated or non-methylated) (7m-G-O-5'-(HO)(O)P—O—(HO) (O)P—O—P(HO)(O)—O-5'); 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Where desired, the nucleic acid, e.g., iRNA, DNA, etc, agents described herein can be formulated for administration to a subject, such as parenterally, e.g. via injection, orally, topically, to the eye, etc. As such, the nucleic acid can be combined with a pharmaceutically acceptable vehicle to provide a pharmaceutical composition. For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation. The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as Mg24), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same gene but different target sequences.

The nucleic acids can be formulated into pharmaceutical compositions by combination with appropriate, pharmaceutically acceptable vehicles, i.e., carriers or diluents, and may be formulated into preparations in solid, semi solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Nucleic acids may also be introduced into tissues or host cells by other routes, including microinjection, or fusion of vesicles. Jet injection may also be used for intra-muscular administration, as described by Furth et al. (1992), Anal Biochem 205:365-368. The nucleic acids may be coated onto gold microparticles, and delivered intradermally by a particle bombardment device, or "gene gun" as described in the literature (see, for example, Tang et al. (1992), Nature 356:152 154), where gold microprojectiles are coated with the DNA, then bombarded into skin cells. Additional nucleic acid delivery protocols of interest include, but are not limited to: those described in U.S. patents of interest include U.S. Pat. No. 5,985,847 and U.S. Pat. No. 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc. See e.g., the viral and non-viral mediated delivery protocols described above. Accordingly, of interest are pharmaceutical vehicles for use in such delivery methods.

The ribonucleic acids produced by embodiments of the methods find use in a variety of different applications, including but not limited to differential gene expression analysis, gene-silencing applications, nucleic acid library generation applications and therapeutic applications (e.g., in the production of antisense RNA, siRNA, etc.) Additional details regarding these types of utilities for RNA produced according to embodiments of the invention are provided in pending U.S. patent application Ser. No. 10/961,991 titled "Array-Based Methods for Producing Ribonucleic Acids," filed on Oct. 8, 2004 and published as US-2006-0078889-A1 on Apr. 13, 2006; the disclosure of which is herein incorporated by reference.

Kits

Also of interest are kits for use in practicing certain embodiments of the invention. In certain embodiments, kits include at least 2 different protected monomers, e.g., 2' thiocarbon protected nucleoside monomers in accordance with the invention, where the kits may include the monomers that have the same nucleobase or monomers that include different nucleobases, e.g., A, G, C and U. The kits may further include additional reagents employed in methods of the invention, e.g., buffers, oxidizing agents, capping agents, cleavage agents, etc.

A specific embodiment comprises four such nucleoside monomers, comprising adenine, uracil, guanine, and cytosine, respectively. Each of the adenine, guanine, and cytosine is optionally protected, such as by the same thiocarbon protecting group protecting the 2'-OH of the nucleoside. The nucleoside monomers optionally comprise a 5'-protecting group, such as DMT, a 3'-protecting group, and/or a phosphoramidite group. The kit may further comprise reagents for post-synthesis RNA deprotection, such as TBAF, tBuOOH, $H_2O_2$, HF, HF-pyridine, HF-TEMED HF-TEA, pyridine, TEMED, neet alkyl amines, amines in organic solvents, mixtures of amines neet or in solvent systems, and/or TEA or TBAH.

Some other kit embodiments comprise components useful for the preparation of nucleoside monomer precursors. The kit may comprise $TIPSCl_2$ and a dithiochloroformate or thiocarbonyl chloroformate. The kit may further comprise reagents such as HF, pyridine, $CH_3CN$, a DMT-containing blocking agent (such as DMT chloride), and/or $CH_3OP$ $(NiPr_2)_2$. The kits may include deprotecting reagents/compositions, e.g., as described above. The kit may also comprise unprotected ribonucleoside monomers, such as adenosine, guanosine, uridine, and/or cytidine.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples illustrate the synthesis of compounds of the present invention, and are not intended to limit the scope of the invention set forth in the claims appended hereto.

EXPERIMENTAL

I. Synthesis of Various 2'-thiocarbonate Monomers

A. Synthesis of 5'-O-DMT-2'-O-thiocarbonyl-3'-O-[methyl-(N,N-diisopropyl)]-phosphoramidite Uridine

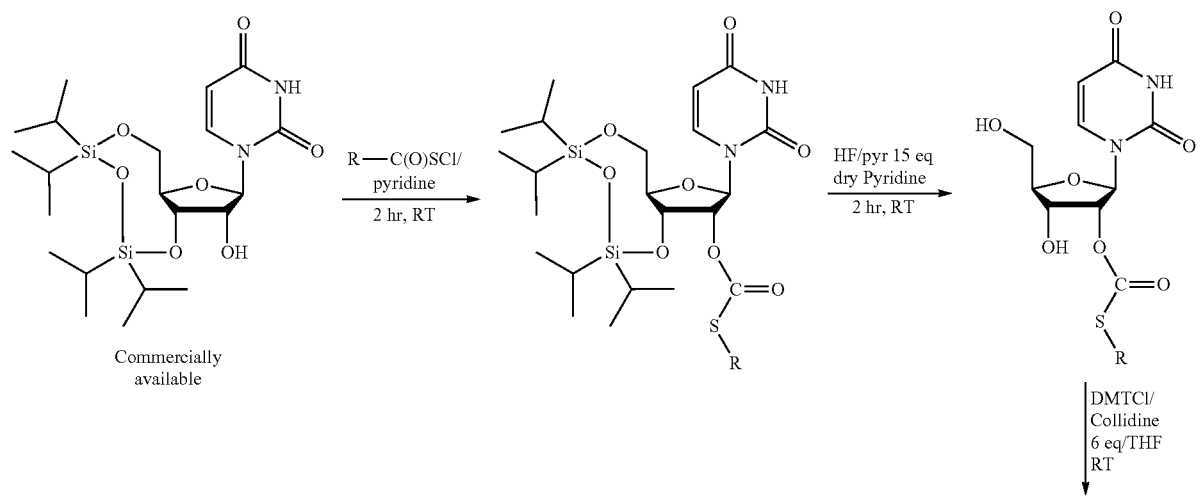

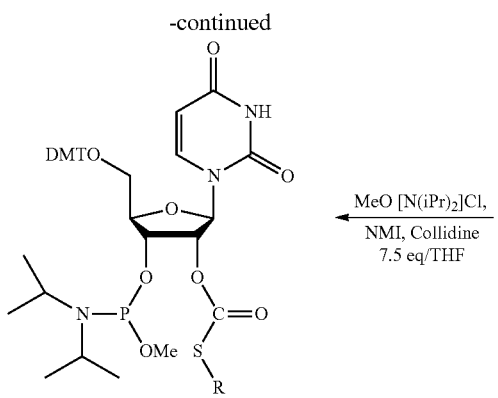
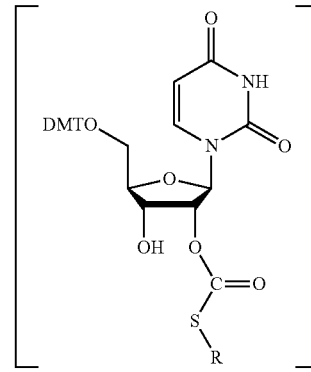

No isolation of DMT compound

R= —CH₃, —CH₂CH₃, —CH(CH₃)₂, -tert-Butyl

NMI
(N-Methyl Imidazole)

HF/Pyridine is a complex made of HF/Pyridine:70/30: w/w

Depending on R, the tritylation reaction can be slow and NMI or DMAP can be added in a small amount (0.1 eq) to accelerate the reaction. In order to synthesize 2'-O-t-butylthiocarbonate (BSC) uridine, one may use 5',3'-O-(Tetraisopropyldisiloxane-1,3-diyl) 2'-O-(p-nitrophenyl) carbonate protected uridine as a precursor. The sodium 2-methyl-2-propanethiolate may be used to displace the p-nitrophenyl carbonate as depicted below.

As a general approach to synthesize 2'-thiocarbonate where the corresponding chlorothioformate is not available, it is possible to use the corresponding mercaptan derivative and react it with phosgene to obtain the corresponding chlorothioformate or it is also possible to react the mercaptan with the 2' O-(p-nitrophenyl)oxycarbonyl protected nucleoside.

B. Synthesis of 5',3'-O-(Tetraisopropyldisiloxane-1,3-diyl) 2'-O-t-butylthiocarbonyl (BSC) uridine 5',3'-O-(Tetraisopropyldisiloxane-1,3-diyl) 2'-O-(p-nitrophenyl) carbonate protected uridine (15 mmole) was coevaporated 3 times with pyridine, and then dried on vacuum pump for 4 hours Anhydrous pyridine (150 mL) and sodium 2-methyl-2-propanethiolate (24 mmole) were added, and the mixture was stirred at room temperature for 16 hours. The product was purified by column chromatography using hexanes with a gradient of EtOAc (0-30%). Yield 76.4% ESI MS: 609 (M+Li), 637 (M+Cl)

C. Synthesis of 5',3'-O-(Tetraisopropyldisiloxane-1,3-diyl) 2'-O-Ethylthiocarbonyl (ESC) uridine 5',3'-O-(Tetraisopropyldisiloxane-1,3-diyl) uridine (15 mmole) was coevaporated 3 times with pyridine, and then dried on vacuum pump for 12 hours. Anhydrous pyridine (150 mL), and ethyl chlorothioformate (18 mmole) were added, and the mixture was stirred at room temperature for 16 hours. The product was purified by column chromatography using hexanes with a gradient of chloroform (50-100%).

Yield 74.3%

ESI MS: 581 (M+Li), 609 (M+Cl)

D. Removal of the TIPS 2'-O-thiocarbonyl Protected Uridines

Hydrogen fluoride-pyridine complex (HF:Py 7:3, 7 mL) was carefully to ice-cold solution of pyridine (8 mL) in acetonitrile (46.5 mL). The pyridine-HF reagent so formed (32 mL) was then transferred to the flask with 5',3'-O-(tetraisopropyldisiloxane-1,3-diyl) 2'-O-carbonate protected uridine (10 mmole), and the mixture was stirred at room temperature for 2 hours. The reaction was quenched with 5% solution of calcium chloride in water (300 mL). Crude product was extracted with EtOAc (3-5 times), and dried with anhydrous Na₂SO₄. After filtration organic layer was concentrated to dryness and left on vacuum pump for 16 hours.

Yield 85-100%

ESI MS:

BSC analog: 361 (M+1), 383 (M+Na), 399 (M+K)

ESC analog: 333 (M+1), 355 (M+Na), 371 (M+K)

E. Synthesis of 5'-O-DMT 2'-O-thiocarbonyl protected uridine 3'-O-[methyl-(N,N-diisopropyl)]-phosphoramidites 2'-O-thiocarbonate protected uridine (3 mmole) was dried on a vacuum pump for 6 hours. Anhydrous THF (30 mL), 2,4,6-collidine (22.5 mmole) and dimethoxytrityl chloride (3.3 mmole) were added, and the mixture was stirred at room temperature until TLC (CHCl₃/MeOH 9:1) showed full disappearance of nucleoside substrate (16-24 hours). 2,4,6-Collidine (3 mmole) and 1-methylimidazole (1.5 mmole) were added in one portion and N,N-diisopropylmethylphosphonamidic chloride was added slowly to the reaction mixture over 10-15 minutes. The reaction mixture was then stirred for another 2 hours. The solvent was removed in vacuo, and the crude product was purified by column chromatography using hexanes with a gradient of EtOAc (0-50%).

Yield 60-65%

ESI MS:

ESC monomer: 802 (M+Li), 830 (M+Cl)

BSC monomer: 830 (M+Li), 858 (M+Cl)

$^{31}$P NMR (CDCl₃):

ESC monomer: 152.33, 151.72

F. Synthesis of 5',3'-O-(Tetraisopropyldisiloxane-1,3-diyl) 2'-O-Ethylthiocarbonyl (ESC) N⁴-phenyloxycarbonyl Cytidine 5',3'-O-(tetraisopropyldisiloxane-1,3-diyl)ribocytidine (10 mMole, 4.85 g) was dried by coevaporation with dry pyridine. This compound was dissolved in 100 ml of dry pyridine and trimethylchlorosilane (5 eq, 50 mMole, 6.34 ml) was added. The mixture was stirred at round temperature during 2 hours and the phenylchloroformate was added (1.2 eq, 12 mMole, 1.51 ml). The reaction was stirred at room temperature during 2 hours. The excess of chloroformate was quenched by adding 2 ml of methanol, the reaction was diluted by a saturated solution of sodium bicarbonate in water. This solution was extracted with dichloromethane. The organic layer was then dried over sodium sulfate and evaporated to dryness.

The crude product of this reaction was diluted in 160 ml of dichloromethane and 5.7 g of p-toluenesulfonic acid in 30 ml of THF. The reaction was stirred at room temperature for 15 min. The reaction was quenched by adding 200 ml of a saturated aqueous solution of sodium bicarbonate. This solution was extracted with dichloromethane, the organic layer was dried over sodium sulfate and evaporated to dryness.

The crude product was dried by coevaporation with dry pyridine, dissolved in 100 ml of dry pyridine, and the ethylchlorothioformate (1.7 eq, 1.76 ml) and the DMAP (0.1 eq, 0.122 g) were added. The reaction was stirred at room temperature overnight, then diluted by a saturated aqueous solution of sodium bicarbonate. This mixture was extracted with dichloromethane, the organic layer was dried over sodium sulfate and evaporated to dryness. The crude was purified by column chromatography (cyclohexane/ethylacetate 75/25). The product was obtained as a foam (4 g, 60% over 4 steps).

$^1$H NMR 400 MHz (CDCl$_3$): 8.2 (s, 1H); 7.45-7.2 (m, 5H); 5.95 (s, 1H); 5.55 (d, 1H); 4.35 (m, 1H); 4.3 (d, 1H); 4.2-3.95 (m, 2H); 2.95-2.8 (m, 2H); 1.3 (t, 3H); 1.15-0.95 (m, 27H) G

Mass spectrum ESI: 700.2274 [M+Li]$^+$

G. Synthesis of 2'-O-ethylthiocarbonyl N⁴-phenyloxycarbonyl Cytidine

5',3'-O-(Tetraisopropyldisiloxane-1,3-diyl) 2'-O-ethylthiocarbonate N⁴-phenylcarbamate Cytidine (2.57 g, 5.7 mmole) was dried by coevaporation with dry acetonitrile, then diluted in 40 ml of dry acetonitrile and the HF/pyridine (30 eq of HF, 4.33 ml) was added and the reaction was stirred at room temperature during 5 h. The fluoride was quenched by adding a solution of CaCl$_2$ and the product was extracted with dichloromethane. The organic layer was dried over sodium sulfate and evaporated to dryness.

The crude was coevaporated with dry acetonitrile, then dissolved in 40 ml of dry THF and 10 eq (7.55 ml) of 2,4,6-collidine was added to the reaction. The DMTCl (1.2 eq, 2.31 g) was added and the reaction was stirred at room temperature during 3 h 30. 5 more equivalent of 2,4,6-collidine (3.3 ml), 0.5 eq (0.22 ml) of N-methylimidazole and 2.5 eq (2.75 ml) of N,N-diisopropylmethyl-phosphonamidic chloride were added. The reaction was stirred at room temperature for 4 h. The mixture was diluted with a saturated aqueous solution of sodium bicarbonate and extracted with dichloromethane. The organic layer was dried over sodium sulfate and evaporated to dryness. The crude was purified by column chromatography (hexane/ethylacetate/pyridine 75/20/5 to 20/75/5). The product desired was obtained as a slightly yellow foam (1.64 g, 31% over 3 steps).

$^{31}$P NMR 400 MHz (CD$_3$CN): 151.709-151.325

Mass spectrum ESI: 921.332 [M+Li]$^+$

H. Protection of the Exocyclic Adenosyl Amino Group

5',3'-O-(tetraisopropyldisiloxane-1,3-diyl) adenosine (3.9 mMole, 2 g) was coevaporated twice with dry pyridine. This compound was dissolved in 20 ml of dry pyridine and trimethylchlorosilane (5 eq, 19.6 mMole, 2.48 ml) was added. The mixture was stirred at room temperature during 30 min and the phenylchloroformate was added (2 eq, 7.84 mMole, 0.98 ml). The reaction was stirred at room temperature during 2 hours. Then, 5 ml of water was added to the reaction and the mixture was stirred at room temperature for another 2 h. The reaction was then diluted with a saturated aqueous solution of sodium bicarbonate. This solution was extracted with dichloromethane. The organic layer was dried over sodium sulfate and evaporated to dryness. The crude was purified by column chromatography (CH$_2$Cl$_2$ to CH$_2$Cl$_2$/MeOH 90/10). The product was obtained as white foam (0.62 g, 25%)

$^1$H NMR 400 MHz (CDCl$_3$): 9.85 (s, 1H); 8.75 (s, 1H); 8.2 (s, 1H); 7.4-7.2 (m, 5H); 6.05 (s, 1H); 5.05 (m, 1H); 4.65 (d, 1H); 4.15-4 (m, 4H); 3.75 (s, 1H); 1.15-0.95 (m, 27H)

I. Synthesis of 5'-O-DMT-2'-O-ethylthiocarbonyl-3'-O-[methyl-(N,N-diisopropyl)]-phosphoramidite-N⁶-phenyloxycarbonyl Adenosine 5',3'-O-(tetraisopropyldisiloxane-1,3-diyl) N⁶-phenyloxycarbonyl adenosine (0.62 g, 1 mMole) was dried by coevaporation with anhydrous pyridine, and dissolved in 5 ml of dry pyridine. Ethychlorothioformate (1.7 eq, 2 mMole, 0.208 ml) and DMAP (0.1 eq, 0.012 g) were added. The reaction was stirred at room temperature overnight, then diluted by a saturated aqueous solution of sodium bicarbonate. The crude reaction mixture was extracted with dichloromethane. The organic layer was dried over sodium sulfate and evaporated to dryness.

The crude product was dried by coevaporation with dry acetonitrile, and then diluted in 5 ml of dry acetonitrile. HF/pyridine (30 eq of HF, 0.375 ml) was added and the reaction was stirred at room temperature during 5 h. The fluoride was quenched by adding a solution of CaCl$_2$ and the product was extracted with dichloromethane. The organic layer was dried over sodium sulfate and evaporated to dryness.

The crude product was dried by coevaporation with dry acetonitrile, then 5 ml of dry THF were added and 10 eq (1.35 ml) of 2,4,6-collidine. DMTCl (1.2 eq, 0.4 g) was added and the reaction was stirred at room temperature during 2 h. 5 more equivalent of 2,4,6-collidine (0.7 ml), 0.5 eq (0.039 ml) of N-methylimidazole and 2.5 eq (1.45 ml) of N,N-diisopropylmethyl-phosphonamidic chloride were added. The reaction was stirred at room temperature for 2 h. The mixture was diluted with a saturated aqueous solution of sodium bicarbonate and extracted with dichloromethane. The organic layer was dried over sodium sulfate and evaporated to dryness. The crude was purified by column chromatography (hexane/ethylacetate/pyridine 75/20/5 to 20/75/5). The product desired was obtained as a white foam.

$^{31}$P NMR 400 MHz (CDCl$_3$): 152.925-152.040

J. Synthesis of 5'-O-DMT-2'-O-thiocarbonyl-3'-O-[methyl-(N,N-diisopropyl)]-phosphoramidite N⁴-thiocarbonyl cytidine, N⁴-thiocarbonyl Guanosine, and N⁶-thiocarbonyl adenosine

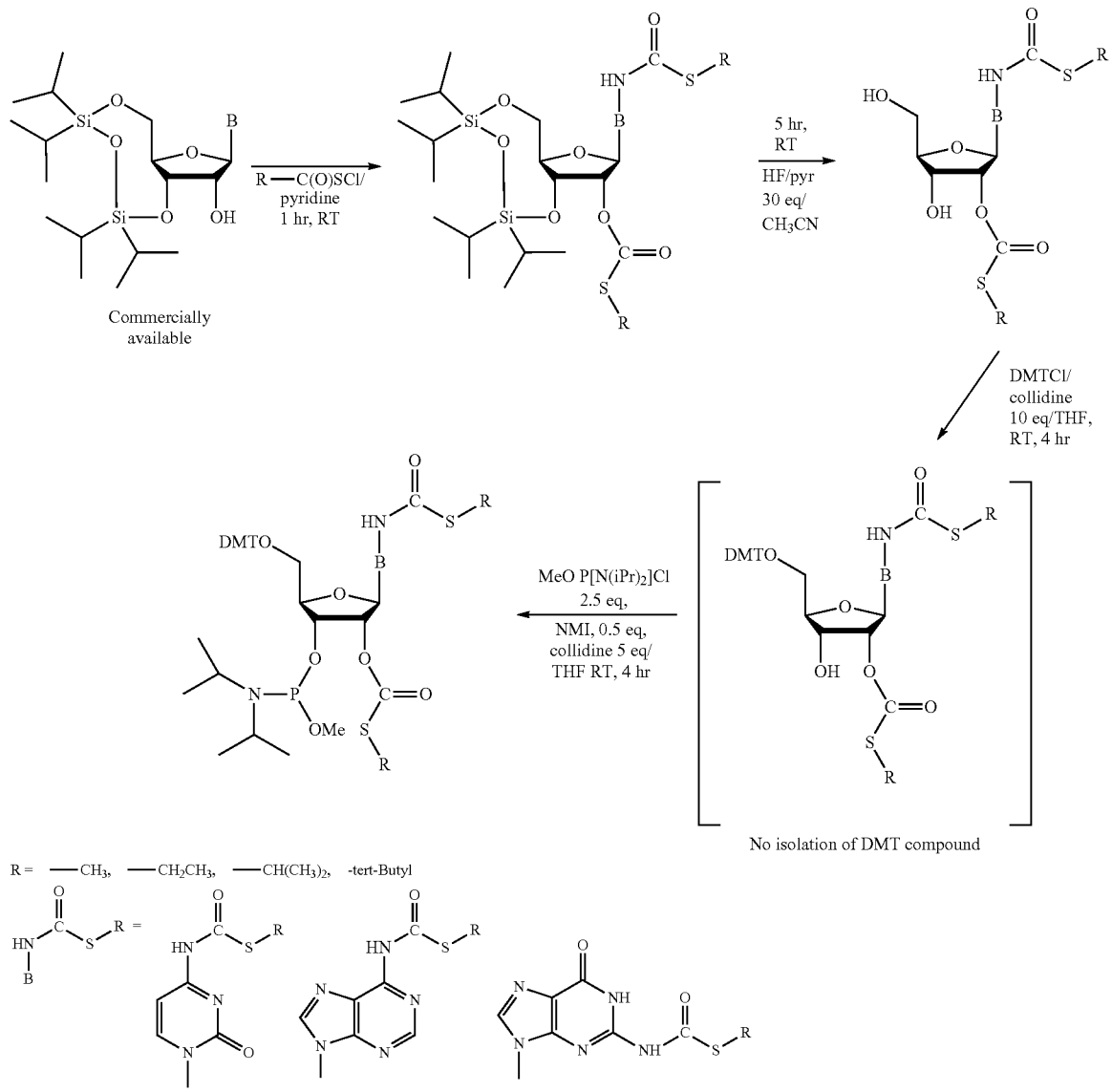

II. Cleavage/Deprotection Study of Different 2'-Thiocarbonate Groups on Monomers A solution of Tetrabutylammonium Fluoride (TBAF) 1M in THF was used to cleave the various 2'-thiocarbonyl protecting groups. It appears that all thiocarbonates are cleaved by this solution, and as expected with an increased half-life for thiocarbonates with greater alkyl groups.

| R | $T^{1/2}$ |
|---|---|
| Methyl (MSC) | 3 min |
| Ethyl (ESC) | 10 min |
| Isopropyl (ISC) | 70 min |
| T-Butyl (BSC) | 60 min |

III. Synthesis of Various 2'-Thiocarbonylcarbonate and Dithiocarbonate Monomers

A. Synthesis of 5',3'-TIPS-2' pentafluorophenyl oxythiocarbonyl-Uridine

5',3'TIPS-Uridine (5 mmol) was co-evaporated twice with pyridine and dissolved in a DCM/Py (9 ml/4 ml) solution. DMAP (122 mg, 1 mmol) was added and the solution immersed in a water bath (at 20 deg C.). Pentafluorophenyl chlorothionoformate (1.6 mL, 10 mmol) was added slowly (over 1 min) and the reaction stirred for 5 h whereupon water was added. The solution was extracted twice with DCM), washed twice with water, dried (Na2SO4), filtered, and concentrated. The crude was purified on silica-gel chromatography (EtOAC/hexanes) to yield the title compound (64% yield). Mass Calculated: 712.17, Observed: 719.18 [M+Li]+, 746.2 [M+Cl]−.

B. General Method for the Synthesis of Thiono- and Dithiocarbonates

3',5'-TIPS 2'-O-Pentafluorophenyl oxythiocarbonyl uridine was coevaporated twice with 1,4-dioxane, dissolved in THF (3 ml) and placed under argon. The relevant alkoxide/thioalkoxide (2.1 equivalents) was added, and the reaction mixture stirred for 1 h, whereupon $NaHCO_3$ std aq was added and the solution extracted twice with EtOAc, washed once with and once with brine, dried over Na2SO4, concentrated and purified by silica gel chromatography (EtOAc/hexanes).

IV. Synthesis of Various Thionocarbamate Protected Monomers

A. Synthesis of 5'-O-DMT-3'-O-[methyl-(N,N-diisopropyl)]-phosphoramidite-2'-O-morpholinothionocarbamate uridine. 3'-5'-tetraisopropyldisiloxane Uridine (ChemeGenes), 10 mmol, 4.8 grams was dissolved in 100 mls of anhydrous acetonitril in a 500 ml roundbottom flask fitted with a serum stopper. To the reaction 1.9 grams of 1,1'-thiocarbonyldiimidazole (Aldrich) was added with 0.2 grams of 4-(dimethyl)aminopyridine. The reaction was heated using a heat gun and stirred until the reagents had dissolved and the solution was clear. The reaction was allowed to stir overnight (12 hours). After 12 hours, the reaction mixture was a slurry of crystals. The crystals were isolated by filtration through a medium sintered glass funnel. The product was washed with cold acetonitrile and dried under vacuum. TLC analysis confirmed that the product was a single species giving 5.97 grams of product (100%) ESI-Q-TOF mass spectroscopy analysis confirmed the product as the 5',3'-O-(tetraisopropyldisiloxane-1,3-diyl)-2'-thioimidazole with a mass of M+1, 597.12 m/e. The product was redissolved in 100 ml of anhydrous acetonitrile by heating using a heat gun. To the reaction was added 11 mmol of morpholine. The reaction was stopped and stirred for 3 hours. TLC analysis demonstrated spot to spot conversion from the starting material to a higher running product. That product was isolated by evaporation of the acetonitrile to a glass. ESI-Q-TOF mass spectroscopy analysis confirmed the product as the 5',3'-O-(tetraisopropyldisiloxane-1,3-diyl)-2'-morpholino-thionocarbamate with a mass of M+1, 615.21 m/e. Hydrogen fluoride-pyridine complex (HF:Py 7:3, 7 mL) was carefully to ice-cold solution of pyridine (8 mL) in acetonitrile (46.5 mL). The pyridine-HF reagent so formed (32 mL) was then transferred to the flask with 5',3'-O-(tetraisopropyldisiloxane-1,3-diyl)-2'-morpholino-thionocarbamate protected uridine (10 mmole), and the mixture was stirred at room temperature for 2 hours. The reaction was quenched with 5% solution of calcium chloride in water (300 mL). Crude product was extracted with EtOAc (3-5 times), and dried with anhydrous $Na_2SO_4$. After filtration organic layer was concentrated to a viscous oil giving 3.5 grams (94% yield) of product shown as a single spot by TLC with a confirmed identity of the 2'-morpholino-thionocarbamate protected uridine by ESI-Q-TOF mass spectroscopy with a mass of M+1, 373.10 m/e. 2'-O-morpholinothionocarbamate protected uridine (9.4 mmole) was redissolved in anhydrous THF (95 mL), 2,4,6-collidine (70.5 mmole) and dimethoxytrityl chloride (11.75 mmole) were added, and the mixture was stirred at room temperature until TLC ($CHCl_3$/MeOH 9:1) showed full disappearance of nucleoside substrate (16-24 hours). 2,4,6-Collidine (9.4 mmole) and 1-methylimidazole (4.5 mmole) were added in one portion and N,N-diisopropylmethylphosphonamidic chloride (23 mmol) was added slowly to the reaction mixture over 10-15 minutes. The reaction mixture was then stirred for another 2 hours. The solvent was removed in vacuo, and the crude product was purified by column chromatography using hexanes with a gradient of EtOAc (0-50%).

B. Synthesis of 5'-O-DMT-3'-O-[methyl-(N,N-diisopropyl)]-phosphoramidite-2'-O-thiomorpholino-1,1-dioxidethionocarbamate uridine. 3'-5'-tetraisopropyldisiloxane Uridine (ChemeGenes), 10 mmol, 4.8 grams was dissolved in 100 mls of anhydrous acetonitril in a 500 ml roundbottom flask fitted with a serum stopper. To the reaction 1.9 grams of 1,1'-thiocarbonyldiimidazole (Aldrich) was added with 0.2 grams of 4-(dimethyl)aminopyridine. The reaction was heated using a heat gun and stirred until the reagents had dissolved and the solution was clear. The reaction was allowed to stir overnight (12 hours). After 12 hours, the reaction mixture was a slurry of crystals. The crystals were isolated by filtration through a medium sintered glass funnel. The product was washed with cold acetonitrile and dried under vacuum. TLC analysis confirmed that the product was a single species giving 5.97 grams of product (100%) ESI-Q-TOF mass spectroscopy analysis confirmed the product as the 5',3'-O-(tetraisopropyldisiloxane-1,3-diyl)-2'-thionoimidazole with a mass of M+1, 598.12 m/e. The product was redissolved in 100 ml of anhydrous acetonitrile by heating using a heat gun. To the reaction was added 11 mmol of thiomorpholine-1,1-dioxide (TCI America) and 1.1 mmol of 4-(dimethyl)aminopyridine. The reaction was stoppered and stirred for 12 hours. After 12 hours, the reaction mixture was a slurry of crystals. The crystals were isolated by filtration through a medium sintered glass funnel. The product was washed with cold acetonitrile and dried under vacuum. TLC analysis confirmed that the product was a single species giving 6.61 grams of product (99%). ESI-Q-TOF mass spectroscopy analysis confirmed the product as the 5',3'-β-(tetraisopropyldisiloxane-1,3-diyl)-2'-O-thiomorpholino-1,1-dioxidethionocarbamate with a mass of M+1, 664.21 m/e. Hydrogen fluoride-pyridine complex (HF:Py 7:3, 7 mL) was carefully to ice-cold solution of pyridine (8 mL) in acetonitrile (46.5 mL). The pyridine-HF reagent so formed (32 mL) was then transferred to the flask with 5',3'-O-(tetraisopropyldisiloxane-1,3-diyl)-2'-O-thiomorpholino-1,1-dioxidethionocarbamate protected uridine (10 mmole), and the mixture was stirred at room temperature for 2 hours. The reaction was quenched with 5% solution of calcium chloride in water (300 mL). Crude product was extracted with EtOAc (3-5 times), and dried with anhydrous $Na_2SO_4$. After filtration organic layer was concentrated to a viscous oil giving 3.4 grams (80% yield) of product shown as a single spot by TLC with a confirmed identity of the 2'-O-thiomorpholino-1,1-dioxidethionocarbamate protected uridine by ESI-Q-TOF mass spectroscopy with a mass of M+1, 422.10 m/e. 2'-O-thiomorpholino-1,1-dioxidethionocarbamate protected uridine (8.0 mmole) was redissolved in anhydrous THF (80 mL), 2,4,6-collidine (60 mmole) and dimethoxytrityl chloride (10.0 mmole) were added, and the mixture was stirred at room temperature until TLC ($CHCl_3$/MeOH 9:1) showed full disappearance of nucleoside substrate (16-24 hours). 2,4,6-Collidine (8.0 mmole) and 1-methylimidazole (4.0 mmole) were added in one portion and N,N-diisopropylmethylphosphonamidic chloride (20 mmol) was added slowly to the reaction mixture over 10-15 minutes. The reaction mixture was then stirred for another 2 hours. The solvent was removed in vacuo, and the crude product was purified by column chromatography using hexanes with a gradient of EtOAc (0-50%).

C. Synthesis of 5'-O-DMT-3'-O-[methyl-(N,N-diisopropyl)]-phosphoramidite-2'-O-dimethylhydroxylaminothionocarbamate uridine. 3'-5'-tetraisopropyldisiloxane Uridine (ChemeGenes), 10 mmol, 4.8 grams was dissolved in 100 mls of anhydrous acetonitrile in a 500 ml roundbottom flask fitted with a serum stopper. To the reaction 1.9 grams of 1,1'-thiocarbonyldiimidazole (Aldrich) was added with 0.2 grams of 4-(dimethyl)aminopyridine. The reaction was heated using a heat gun and stirred until the reagents had dissolved and the solution was clear. The reaction was allowed to stir overnight (12 hours). After 12 hours, the reaction mixture was a slurry of crystals. The crystals were isolated by filtration through a medium sintered glass funnel. The product was washed with cold acetonitrile and dried under vacuum. TLC analysis confirmed that the product was a single species giving 5.97 grams of product (100%) ESI-Q-TOF mass spectroscopy analysis confirmed the product as the 5',3'-β-(tetraisopropyldisiloxane-1,3-diyl)-2'-thionoimidazole with a mass of M+1, 598.12 m/e. The product was suspended in 100 ml of anhydrous acetonitrile. To the reaction mixture was added 11 mmol of N,O-dimethylhydroxylamine hydrochloride (Aldrich), 15 mmol of diisopropylethylamine and 1.1 mmol of 4-(dimethyl)aminopyridine. The reaction was heated using a heat gun to dissolve the reagents, producing a clear solution. The mixture was stoppered and stirred for 12 hours. After 12 hours, the reaction mixture was evaporated to an oil, and dried under vacuum. TLC analysis confirmed that the product was a single species giving 5.9 grams of product. ESI-Q-TOF mass spectroscopy analysis confirmed the product as the 5',3'-O-(tetraisopropyldisiloxane-1,3-diyl)-2'-O-dimethylhydroxylaminothionocarbamate with a mass of M+1, 590.24 m/e. Hydrogen fluoride-pyridine complex (HF:Py 7:3, 7 mL) was carefully to ice-cold solution of pyridine (8 mL) in acetonitrile (46.5 mL). The pyridine-HF reagent so formed (32 mL) was then transferred to the flask with 5',3'-O-(tetraisopropyldisiloxane-1,3-diyl)-2'-O-dimethylhydroxylaminothionocarbamate protected uridine (10 mmole), and the mixture was stirred at room temperature for 2 hours. The reaction was quenched with 5% solution of calcium chloride in water (300 mL). Crude product was extracted with EtOAc (3-5 times), and dried with anhydrous Na2SO4. After filtration organic layer was concentrated to a viscous oil giving 3.1 grams (86% yield) of product shown as a single spot by TLC with a confirmed identity of the 2'-O-dimethylhydroxylaminothionocarbamate protected uridine by ESI-Q-TOF mass spectroscopy with a mass of M+1, 348.09 m/e. 2'-O-dimethylhydroxylaminothionocarbamate protected uridine (8.7 mmole) was redissolved in anhydrous THF (90 mL), 2,4,6-collidine (61 mmole) and dimethoxytrityl chloride (10.0 mmole) were added, and the mixture was stirred at room temperature until TLC (CHCl$_3$/MeOH 9:1) showed full disappearance of nucleoside substrate (16-24 hours). 2,4,6-Collidine (9.0 mmole) and 1-methylimidazole (4.5 mmole) were added in one portion and N,N-diisopropylmethylphosphonamidic chloride (22 mmol) was added slowly to the reaction mixture over 10-15 minutes. The reaction mixture was then stirred for another 2 hours. The solvent was removed in vacuo, and the crude product was purified by column chromatography using hexanes with a gradient of EtOAc (0-50%).

D. Synthesis of 5'-O-DMT-3'-O-[methyl-(N,N-diisopropyl)]-phosphoramidite-2'-O-phenylaminothionocarbamate uridine. 3'-5'-tetraisopropyldisiloxane Uridine (ChemeGenes), 10 mmol, 4.8 grams was dissolved in 100 mls of anhydrous acetonitrile in a 500 ml roundbottom flask fitted with a serum stopper. To the reaction 1.9 grams of 1,1'-thiocarbonyldiimidazole (Aldrich) was added with 0.2 grams of 4-(dimethyl)aminopyridine. The reaction was heated using a heat gun and stirred until the reagents had dissolved and the solution was clear. The reaction was allowed to stir overnight (12 hours). After 12 hours, the reaction mixture was a slurry of crystals. The crystals were isolated by filtration through a medium sintered glass funnel. The product was washed with cold acetonitrile and dried under vacuum. TLC analysis confirmed that the product was a single species giving 5.97 grams of product (100%) ESI-Q-TOF mass spectroscopy analysis confirmed the product as the 5',3'-O-(tetraisopropyldisiloxane-1,3-diyl)-2'-thionoimidazole with a mass of M+1, 598.12 m/e. The product was suspended in 100 ml of anhydrous acetonitrile. To the reaction mixture was added 11 mmol of aniline (Aldrich), and 11 mmol of 4-(dimethyl)aminopyridine. The reaction was fitted with a reflux condenser and heated to reflux for 12 hours. After 12 hours, the reaction mixture was evaporated to an oil, and dried under vacuum. TLC analysis confirmed that the product was present in about 80% yield along with 2,2-anhydrouridine. The product was purified on silica gel using a methanol/methylene chloride gradient (0-5%). ESI-Q-TOF mass spectroscopy analysis confirmed the product as the 5',3'-O-(tetraisopropyldisiloxane-1,3-diyl)-2'-O-phenylaminothionocarbamate with a mass of M+1, 621.33 m/e. Hydrogen fluoride-pyridine complex (HF:Py 7:3, 7 mL) was carefully to ice-cold solution of pyridine (6.5 mL) in acetonitrile (37.2 mL). The pyridine-HE reagent so formed (25 mL) was then transferred to the flask with 5',3'-O-(tetraisopropyldisiloxane-1,3-diyl)-2'-O-dimethylhydroxylaminothionocarbamate protected uridine (8 mmole), and the mixture was stirred at room temperature for 2 hours. The reaction was quenched with 5% solution of calcium chloride in water (300 mL). Crude product was extracted with EtOAc (3-5 times), and dried with anhydrous Na2SO4. After filtration organic layer was concentrated to a viscous oil giving 2.4 grams (81% yield) of product shown as a single spot by TLC with a confirmed identity of the 2'-O-phenylaminothionocarbamate protected uridine by ESI-Q-TOF mass spectroscopy with a mass of M+1, 379.18 m/e. 2'-O-phenylaminothionocarbamate protected uridine (6.4 mmole) was redissolved in anhydrous THF (65 mL), 2,4,6-collidine (45 mmole) and dimethoxytrityl chloride (8.0 mmole) were added, and the mixture was stirred at room temperature until TLC (CHCl3/MeOH 9:1) showed full disappearance of nucleoside substrate (16-24 hours). 2,4,6-Collidine (6.4 mmole) and 1-methylimidazole (3.2 mmole) were added in one portion and N,N-diisopropylmethylphosphonamidic chloride (16 mmol) was added slowly to the reaction mixture over 10-15 minutes. The reaction mixture was then stirred for another 2 hours. The solvent was removed in vacuo, and the crude product was purified by column chromatography using hexanes with a gradient of EtOAc (0-50%).

V. General Procedure for Oligouridine Synthesis on Solid Support

All syntheses were performed on a 1 microM scale using dT-Q-CPG columns from Glen Research according to standard RNA cycle. For coupling step phosphoramidite and tetrazole were delivered to the synthesis column and left for 10 minutes.

After completion of all synthesis steps, and in order to remove the methyl protecting group on the phosphate moieties, the oligoribonucleotide (still joined to CPG) was treated with 1 M solution of disodium 2-carbamoyl-2-cyanoethylene-1,1-dithiolate in DMF (1 mL) for 30 minutes at room temperature, and then washed with water followed by acetonitrile and dried by argon.

For the thionocarbamate containing 2'-protected oligonucleosides the cyanoethyl phosphate protecting group could be cleaved using 20% diethyl amine in anhydrous acetonitrile for on hour at room temperature.

Oligomers were cleaved from solid support and 2'-deprotected by treatment with 1M TBAF solution in THF (1 mL) It is important to note that the TBAF solution must be dried with less than 5% water content. For U₄T pentamers deprotection was completed within 1 hour (ESC protection) and 6 hours (BSC protection).

Reactions were quenched with 0.1 M TEAA, desalted on Poly-pak cartridges using standard procedure, and evaporated to dryness. The resulting reaction products were dissolved in water and analyzed by HPLC [ODS-Hypersil (5 m), column 4.0×250, flow 1.5 mL/min, 0-20% MeCN in 50 mM TEAB (linear gradient) in 40 min].

In some cases oligomers were cleaved from solid support (without performing 2'-deprotection) by treatment with TEMED/HF/MeCN mixture (2:1:7, 1 mL) for 40 minutes at room temperature. Reactions were quenched, desalted analyzed as mentioned before.

For thionocarbonate and thionocarbamate protecting groups, oligonucleotides were cleaved from support and deprotected using anhydrous amines. Typical conditions were anhydrous gaseous ammonia at 80 psi at room temperature for 6 to 24 hours; anhydrous methyl amine at 30 psi at room temperature for 1 to 6 hours; ammonia dissolved in anhydrous acetonitrile for 6 to 24 hours; ethylenediamine dissolved in phenol for 6 to 12 hours; 1,3-propanediamine, neet for 4 to 16 hours. Morpholine, neet for 16 to 48 hours; hydroxymethyl amine in anhydrous acetonitrile for 4 to 12 hours.

The gaseous amines were vented and the solid supports washed with a flow of anhydrous argon gas. The solid supports were then placed under vacuum for 2 to 12 hours then the oligonucleotides rinsed from the support using a buffered aqueous solution analyzed by HPLC [ODS-Hypersil (5 m), column 4.0×250, flow 1.5 mL/min, 0-20% MeCN in 50 mM TEAB (linear gradient) in 40 min]. The anhydrous neet amines or amines dissolved in anhydrous solvent were rinsed from the support using 3 to 10 volumes of acetonitrile. The resulting support was washed with a flow of anhydrous argon gas. The solid supports were then placed under vacuum for 2 to 12 hours then the oligonucleotides rinsed from the support using a buffered aqueous solution analyzed by HPLC [ODS-Hypersil (5 m), column 4.0×250, flow 1.5 mL/min, 0-20% MeCN in 50 mM TEAB (linear gradient) in 40 min]

VI. Synthesis of a Mixed Sequence of 3'-TU$_{(2'ESC)}$C$^{POC}_{(2'ESC)}$A$^{POC}_{(2'ESC)}$-C$^{POC}_{(2'ESC)}$A$^{POC}_{(2'ESC)}$ on Solid Support The synthesis was performed on a 1 microM scale using dT-Q-CPG columns from Glen Research according to standard RNA cycle. For coupling step phosphoramidite and tetrazole were delivered to the synthesis column and left for 10 minutes.

The phosphoramidites used in this oligoribonulcleotide synthesis were U$_{2'ESC}$ 2'O-ethyl-thiocarbonyl 5'-O-DMT 3'-O-[methyl-(N,N-diisopropyl)]-phosphoramidite uridine; C$^{POC}_{2'ESC}$ (2'O-ethylthiocarbonyl 5'-O-DMT 3'-O-[methyl-(N,N-diisopropyl)]-phosphoramidite N⁴-phenyloxycarbonyl cytdine) and A$^{POC}_{2'ESC}$2'O-ethylthiocarbonyl 5'-O-DMT 3'-O-[methyl-(N,N-diisopropyl)]-phosphoramidite N⁴-phenyloxycarbonyl cytdine)

After completion of all synthesis steps, and in order to remove the methyl protecting group on the phosphate moieties, the oligoribonucleotide (still joined to CPG) was treated with 1 M solution of disodium 2-carbamoyl-2-cyanoethylene-1,1-dithiolate in DMF (1 mL) for 30 minutes at room temperature, and then washed with DMF then methanol followed by acetonitrile and dried by argon.

The Oligomer was cleaved from solid support and 2'-deprotected by overnight treatment with a solution of 1M TBAF solution in THF (1 mL) to which 10% (v/v) of 1M TBAOH in MeOH was added.

Reactions were quenched with 0.1 M TEAA, desalted on Poly-pak cartridges using standard procedure, and evaporated to dryness. The resulting reaction products were dissolved in water and analyzed by HPLC [ODS-Hypersil (5 m), column 4.0×250, flow 1.5 mL/min, 0-20% MeCN in 50 mM TEAB (linear gradient) in 40 min].

VII. Deprotection

A 1.0 Molar solution of tetrabutylammoniumfluoride in THF was analyzed for water content by Karl-Fischer titration and found to be 4.3%. ¹⁹F NMR of the solution at –60° C. was used to determine the bifluoride concentration at 10%. The solution was stored over anhydrous sodium hydroxide pellets for 9 days and the water content had dropped to 3.1% and the bifluoride content had dropped to 1%. This solution was shown to deprotect a RNA pentamer in 1 hour.

A 1.0 Molar solution of tetrabutylammoniumfluoride in THF was analyzed for water content by Karl-Fischer titration and found to be 4.3%. ¹⁹F NMR of the solution at –60° C. was used to determine the bifluoride concentration at 10%. The solution was stored over anhydrous potassium carbonate for 9 days and the water content had dropped to 3.7% and the bifluoride content had dropped to 0%. This solution was shown to deprotect a RNA pentamer in 1.5 hour.

A 1.0 Molar solution of tetrabutylammoniumfluoride in THF was analyzed for water content by Karl-Fischer titration and found to be 4.3%. ¹⁹F NMR of the solution at –60° C. was used to determine the bifluoride concentration at 10%. Tetrabutylammonium hydroxide 1.0 Molar in water 10% (vol/vol) was added to the solution. The final concentration of water was 12% by Karl-Fisher titration and bifluoride 0% using ¹⁹F NMR. This solution was shown to deprotect a RNA pentamer in 3 hour.

A 1.0 Molar solution of tetrabutylammoniumfluoride in THF was analyzed for water content by Karl-Fischer titration and found to be 4.3%. ¹⁹F NMR of the solution at –60° C. was used to determine the bifluoride concentration at 10%. Tetrabutylammonium hydroxide 1.0 Molar in methanol 10% (vol/vol) was added to the solution. The final concentration of water was 3.2% by Karl-Fisher titration and bifluoride 0% using ¹⁹F NMR. This solution was shown to deprotect a RNA pentamer in 45 min A 1.0 Molar solution of tetrabutylammoniumfluoride in THF was analyzed for water content by Karl-Fischer titration and found to be 4.3%. ¹⁹F NMR of the solution at –60° C. was used to determine the bifluoride concentration at 10%. Tetrabutylammonium hydroxide 1.0 Molar in methanol 20% (vol/vol) was added to the solution. The final concentration of water was 3.4% by Karl-Fisher titration and bifluoride 0% using ¹⁹F NMR. This solution was shown to deprotect a RNA pentamer in 30 min.

A 1.0 Molar solution of tetrabutylammoniumbromide in THF was analyzed for water content by Karl-Fischer titration and found to be 1.8%. Tetrabutylammonium hydroxide 1.0 Molar in water 10% (vol/vol) was added to the solution. This solution was shown to deprotect a RNA pentamer in 1.2 hr.

A 1.0 Molar solution of tetrabutylammoniumbromide in THF was analyzed for water content by Karl-Fischer titration and found to be 1.8%. Tetrabutylammonium hydroxide 1.0 Molar in water 20% (vol/vol) was added to the solution. This solution was shown to fully deprotect a RNA pentamer in 45 min however, with some product of degradation.

A 1.0 Molar solution of tetrabutylammoniumbromide in THF was analyzed for water content by Karl-Fischer titration and found to be 1.8%. Tetrabutylammonium hydroxide 1.0 Molar in methanol 20% (vol/vol) was added to the solution. The final concentration of water was 2.1% by Karl-Fisher titration. This solution was shown to deprotect a RNA pentamer in 30 min.

A 1.0 Molar solution of tetrabutylammoniumacetate in THF was analyzed for water content by Karl-Fischer titration and found to be 2.2%. Tetrabutylammonium hydroxide 1.0 Molar in methanol 20% (vol/vol) was added to the solution. The final concentration of water was 2.4% by Karl-Fisher titration. This solution was shown to deprotect a RNA pentamer in 30 min.

A 1.0 Molar solution of tetrabutylammoniumacetate in Dioxane was analyzed for water content by Karl-Fischer titration and found to be 1.8%. Tetrabutylammonium hydroxide 1.0 Molar in methanol 20% (vol/vol) was added to the solution. The final concentration of water was 2.1% by Karl-Fisher titration. This solution was shown to deprotect a RNA pentamer in 1.5 hours.

A 1.0 Molar solution of tetrabutylammoniumacetate in Acetonitrile was analyzed for water content by Karl-Fischer titration and found to be 1.6%. Tetrabutylammonium hydroxide 1.0 Molar in methanol 20% (vol/vol) was added to the solution. The final concentration of water was 1.8% by Karl-Fisher titration. This solution was shown to deprotect a RNA pentamer in 30 min.

ABBREVIATIONS

In this disclosure, the following abbreviations have the following meanings. Abbreviations not defined have their generally accepted meanings.
° C.=degree Celsius
hr=hour
min=minute
sec=second
μM=micromolar
mM=millimolar
M=molar
ml=milliliter
μl=microliter
mg=milligram
μg=microgram
DMAP=4,4'-dimithylaminopyridine
DMT=dimethoxytrityl
NMI=N-methyl Imidazole
TBAF=tetrabutylammonium fluoride
TBAOH=tetrabutylammonium hydroxide
TBAA=tetrabutylammonium acetate
TBAB=tetrabutylammonium bromide
TBDMS=tert-butyl-dimethylsilyl
TIPS=1,3-tetraisopropyl disiloxane
TEA=triethylamine
TEAA=triethylammonium acetate
TEAB=triethylammonium bicarbonate
TEMED=N,N,N',N'-tetramethylethylenediamine
RP-HPLC=Reverse Phase High Performance Liquid Chromatography

BIBLIOGRAPHY

Beigelman L, and Serebryany V, Nucleosides, Nucleotides, and Nucleic Acids 22: 1007-1009 (2003).
Capaldi et al., Nucleic Acids Research 22(12):2209-2216 (1994).
Greene, et al., "Protective Groups in Organic Synthesis," John Wiley and Sons, Second Edition (1991).
Hogrefe et al., Nucleic Acids Research 21(20): 4739-4741 (1993).
March, Advanced Organic Chemistry, McGraw Hill Book Company, New York (1977). Pages 251-259.
Markiewicz W T, J. Chem Research (S) 24-25 (1979).
Ogilvie et al., Can. J. Chem. 57: 2230-2238 (1979).
Ogilvie et al., Proc. Natl. Acad. Sci. USA 85: 5764 (1988).
Rao et al., J. Chem. Soc., Perkin Trans. 2:43-55 (1993).
Reese C B, Org. Biomol. Chem. 3(21): 3851-68 (2005).
Sakatsume et al., Tetrahedron 47: 8717-8728 (1991).
Scaringe et al., Nucleic Acids Research 18(18): 5433-5441 (1990).
Usman et al., J. Am. Chem. Soc. 109: 7845 (1987).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A compound having the structure of formula (II):

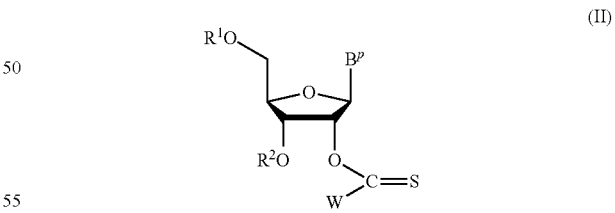

wherein:
B$^P$ is a protected or unprotected heterocyclic group having a 3 to 20 membered ring system;
one of R$^1$ and R$^2$ is a protecting group, and the other of R$^1$ and R$^2$ is a phosphoramidite group;
W is —NH$_2$, —NH—R$^4$ or —NR$^4$—R$^5$, —NH—O—R$^4$ or —NR$^4$—O—R$^5$, wherein R$^4$ and R$^5$ are independently selected from a hydrocarbyl, a substituted hydrocarbyl, an aryl or a substituted aryl, wherein R$^4$ and R$^5$ are optionally cyclically linked, provided that W is not imidazole.

2. The compound according to claim 1, wherein W is —NH—R⁴, and the compound has the structure of formula (IIe):

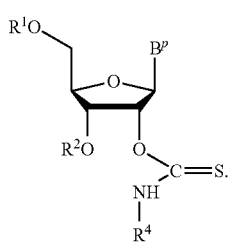
IIe

3. The compound according to claim 1, wherein W is —NR⁴—R⁵, and the compound has the structure of formula (IIf):

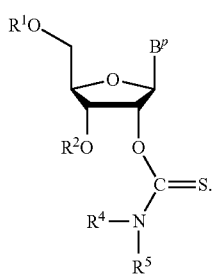
IIf

4. The compound according to claim 1, wherein W is —NH—O—R⁴, and the compound has the structure of formula (IIg):

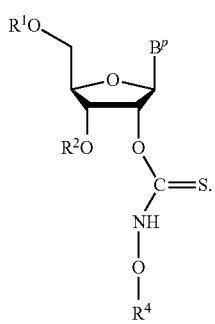
IIg

5. The compound according to claim 1, wherein W is —NR⁴—O—R⁵, and the compound has the structure of formula (IIh):

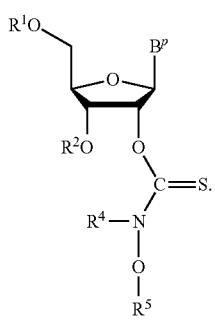
IIh

6. The compound according to claim 1, wherein the compound is one of:

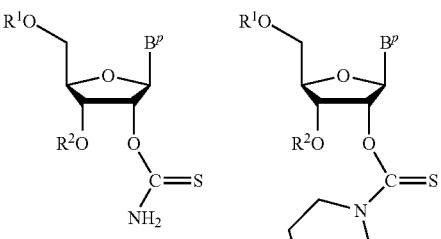

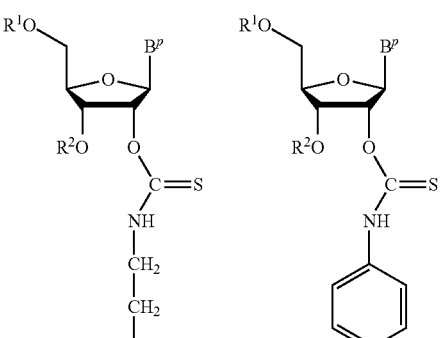

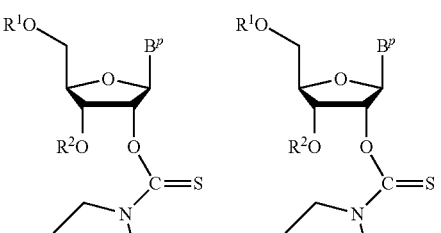

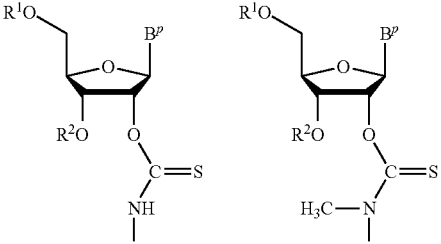

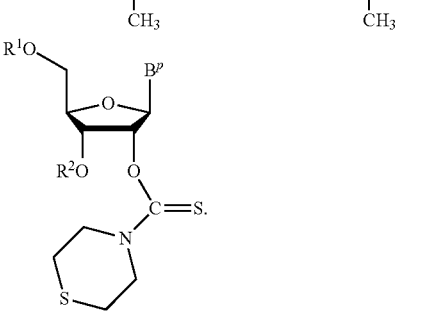

7. The compound according to claim 1, wherein the compound is:

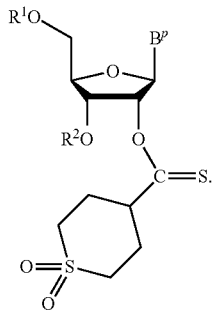

8. A method comprising:
(a) providing a nucleoside residue, wherein said nucleoside residue comprises an unprotected hydroxyl group and a 2'-protected nucleotide monomer, wherein said 2'-protected nucleotide monomer has the structure of formula (II):

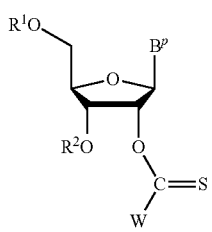

(II)

wherein:
  $B^p$ is a protected or unprotected heterocyclic group having a 3 to 20 membered ring system;
  one of $R^1$ and $R^2$ is a protecting group, and the other of $R^1$ and $R^2$ is a phosphoramidite group;
  W is $-NH_2$, $-NH-R^4$ or $-NR^4-R^5$, $-NH-O-R^4$ or $-NR^4-O-R^5$, wherein $R^4$ and $R^5$ are independently selected from a hydrocarbyl, a substituted hydrocarbyl, an aryl or a substituted aryl, wherein $R^4$ and $R^5$ are optionally cyclically linked; and
(b) contacting said nucleoside residue with said 2'-protected nucleotide monomer under conditions sufficient to covalently bond said phosphoramidite group of said 2'-protected nucleotide monomer to said unprotected hydroxyl group of said nucleoside residue and produce an internucleotide bond.

9. The method according to claim 8, wherein said method further comprises exposing said internucleotide bond to an oxidizing agent.

10. The method according to claim 9, wherein said method further comprises reiterating said contacting step at least once.

11. The method according to claim 8, wherein said method further comprises removing said 2'-hydroxyl protecting group.

12. The method according to claim 8, wherein said nucleoside residue is covalently bound to a solid support.

13. The method according to claim 12, wherein said method further comprises cleaving said nucleic acid from said solid support to produce a free nucleic acid.

14. The method according to claim 8, wherein said 2'-protected nucleotide monomer has the structure of formula (IIe) or formula (IIf):

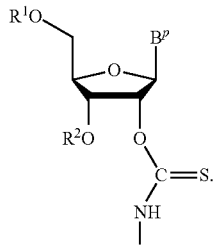

IIe

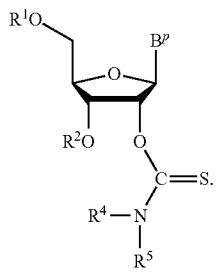

IIf

15. The method according to claim 8, wherein said 2'-protected nucleotide monomer has the structure of formula (IIg) or formula (IIh):

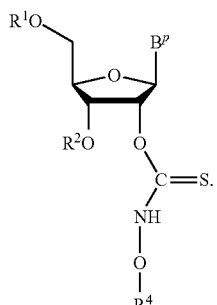

IIg

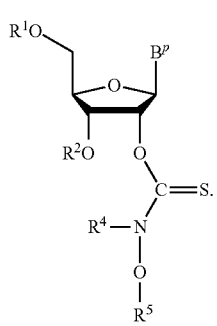

IIh

16. The method according to claim 8, wherein said 2'-protected nucleotide monomer is one of:

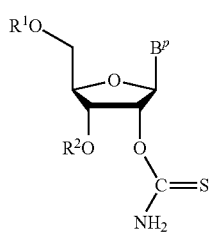 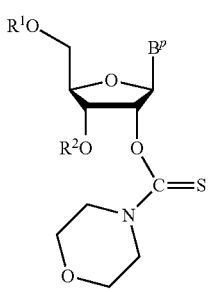

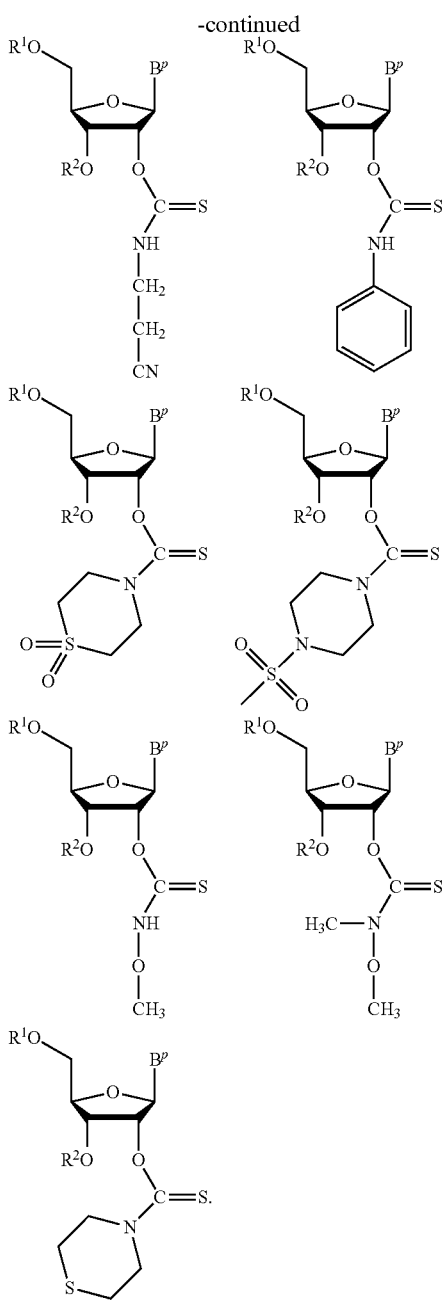

17. The method according to claim 8, wherein said 2'-protected nucleotide monomer is:

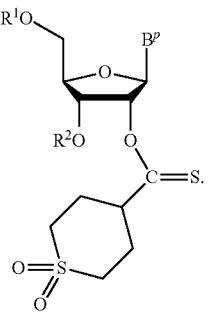

18. The method according to claim 8, further comprising:

(c) oxidizing said internucleotide bond to produce a nucleic acid;

(d) cleaving said nucleic acid from said solid support to produce a free nucleic acid; and (e) chemically modifying said free nucleic acid to produce a modified nucleic acid.

19. A 2'-O-protected nucleic acid comprising the structure:

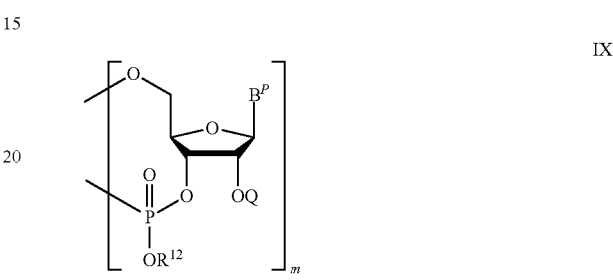

IX wherein:

$B^P$ is a protected or unprotected heterocyclic group having a 3 to 20 membered ring system;

Q is a thiocarbon protecting group having one of the following structures:

—C(=S)—W,

W is —$NH_2$, —NH—$R^4$ or —$NR^4$—$R^5$, —NH—O—$R^4$ or —$NR^4$—O—$R^5$, wherein $R^4$ and $R^5$ are independently selected from a hydrocarbyl, a substituted hydrocarbyl, an aryl or a substituted aryl, wherein $R^4$ and $R^5$ are optionally cyclically linked;

$R^{12}$ is selected from the group consisting of hydrogen, a hydrocarbyl, a substituted hydrocarbyl, an aryl and a substituted aryl; and m is an integer of at least 1.

20. The 2'-O-protected nucleic acid of claim 19, wherein Q is

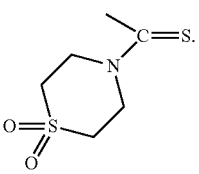

* * * * *

UNITED STATES PATENT AND TRADEMARK OFFICE
CERTIFICATE OF CORRECTION

PATENT NO. : 9,067,961 B2
APPLICATION NO. : 13/485592
DATED : June 30, 2015
INVENTOR(S) : Douglas J. Dellinger et al.

It is certified that error appears in the above-identified patent and that said Letters Patent is hereby corrected as shown below:

On Title page, in item (75), in column 1, line 1, delete "Boulder, CA (US);" and insert -- Boulder, CO (US); --, therefor.

Title page, item (56)

On page 2, in column 1, under "Other Publications", line 2, delete "Intramolecula" and insert -- Intramolecular --, therefor.

On page 2, in column 1, under "Other Publications", line 8, delete "P.," and insert -- P., et al., --, therefor.

On page 2, in column 1, under "Other Publications", line 9, delete "protolytic" and insert -- proteolytic --, therefor.

On page 2, in column 1, under "Other Publications", line 19, delete "Fuji," and insert -- Fujii, --, therefor.

On page 2, in column 1, under "Other Publications", line 31, delete "towards" and insert -- toward --, therefor.

On page 2, in column 2, under "Other Publications", line 5, delete "ribonucleosiden" and insert -- ribonucleoside --, therefor.

On page 2, in column 2, under "Other Publications", line 6, delete "Snythesis," and insert -- Synthesis, --, therefor.

On page 2, in column 2, under "Other Publications", line 24, delete "Trichlor" and insert -- Trichloro --, therefor.

Signed and Sealed this
Fifteenth Day of December, 2015

Michelle K. Lee
*Director of the United States Patent and Trademark Office*

On page 2, in column 2, under "Other Publications", line 45, delete "of21-Deoxy" and insert -- of 2,1-Deoxy --, therefor.

On page 2, in column 2, under "Other Publications", line 46, delete "[3.1.O]" and insert -- [3.1.0] --, therefor.

On page 2, in column 2, under "Other Publications", line 47, delete "dials" and insert -- diols --, therefor.

On page 2, in column 2, under "Other Publications", line 51, delete "84636," and insert -- 64636, --, therefor.

In the Specification

In column 1, line 44, delete "3-O" and insert -- 3'-O --, therefor.

In column 2, line 64-65, delete "queosine," and insert -- queuosine, --, therefor.

In column 3, line 13, delete "2% modified" and insert -- 2'-modified --, therefor.

In column 5, line 4, delete ""The" and insert -- The --, therefor.

In column 5, line 14, delete "0" and insert -- O --, therefor.

In column 5, line 54, after "thio-," insert -- amino-, --.

In column 8, line 51, delete "electrophresis," and insert -- electrophoresis, --, therefor.

In column 12, line 16-17, delete " " and insert -- --, therefor.

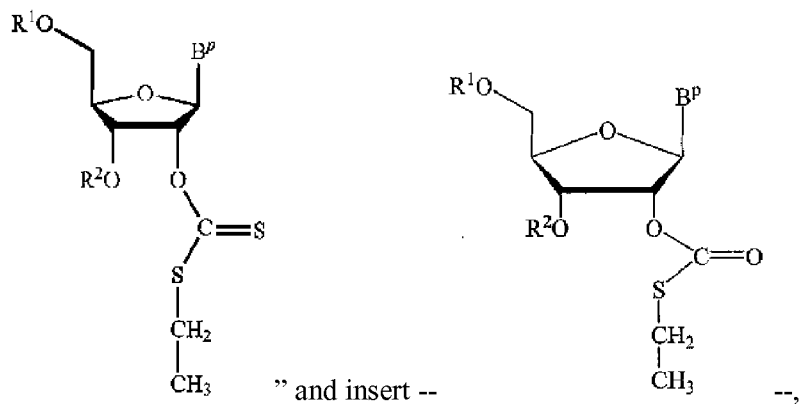

In column 12, line 18-27, delete " 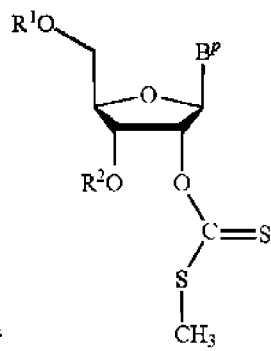 " and insert -- 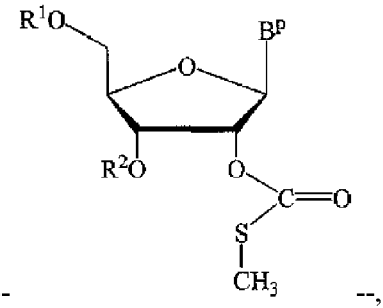 --, therefor.

In column 12, line 28-42, delete " 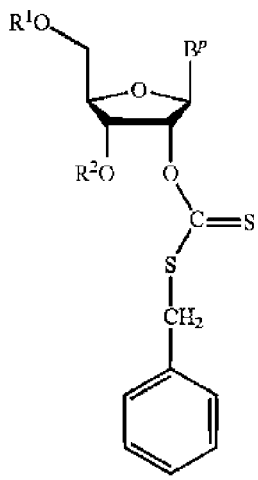 " and insert -- 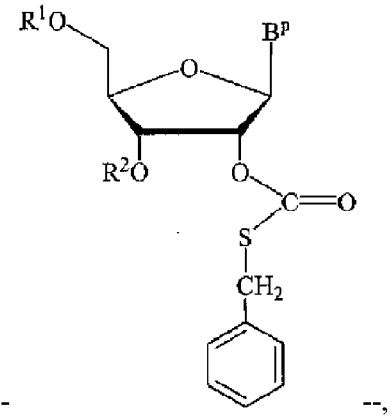 --, therefor.

In column 12, line 63, delete "hydroxylamine" and insert -- hydroxyl amine --, therefor.

In column 12, line 67, delete "hydroxylamine" and insert -- hydroxyl amine --, therefor.

In column 14, line 22, delete "provisio" and insert -- proviso --, therefor.

In column 16, line 18, delete "(O)," and insert -- (G), --, therefor.

In column 16, line 41-42, delete "queosine," and insert -- queuosine, --, therefor.

In column 16, line 50, delete "dibutylforamidine," and insert -- dibutylformamide, --, therefor.

In column 17, line 3-4, delete "phosphoroamidate" and insert -- phosphoramidate --, therefor.

In column 17, line 33, delete "Markewicz" and insert -- Markiewicz --, therefor.

In column 17, line 40, delete "Markewicz" and insert -- Markiewicz --, therefor.

In column 18, line 48, delete "C1-" and insert -- Cl- --, therefor.

CERTIFICATE OF CORRECTION (continued)
U.S. Pat. No. 9,067,961 B2

In column 18, line 61, delete "Seq" and insert -- 5 eq --, therefor.

In column 18, line 64-65, delete "phosphytilating" and insert -- phosphitylating --, therefor.

In column 19, line 16, delete "2' position" and insert -- 2'position --, therefor.

In column 19, line 64, delete "et. al." and insert -- et al., --, therefor.

In column 20, line 17, delete "Markewicz" and insert -- Markiewicz --, therefor.

In column 20, line 54, delete "4-clorobenzylthiocarbonyl," and insert
-- 4-chlorobenzylthiocarbonyl, --, therefor.

In column 20, line 61, delete "dibutylformamidine" and insert -- dibutylformamidine, --, therefor.

In column 23-24, line 2, delete "P[N(iPr)₂]Cl" and insert -- P[N(iPr)2]Cl, --, therefor.

In column 23-24, line 27, delete "phenylcoxycarbonyl" and insert -- phenyloxycarbonyl --, therefor.

In column 25, line 3, delete "—CH₂(CH₃)₂," and insert -- —CH(CH₃)₂, --, therefor.

In column 28, in structure, line 17-27, delete " 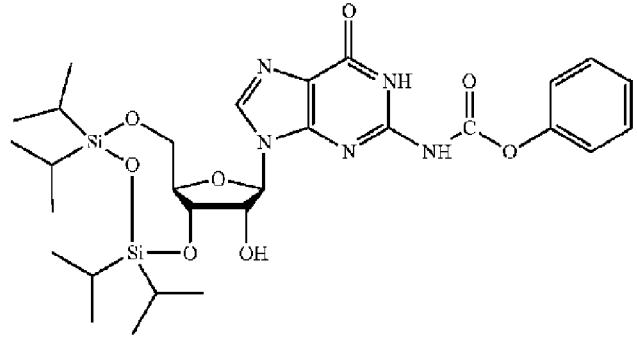 "

and insert -- 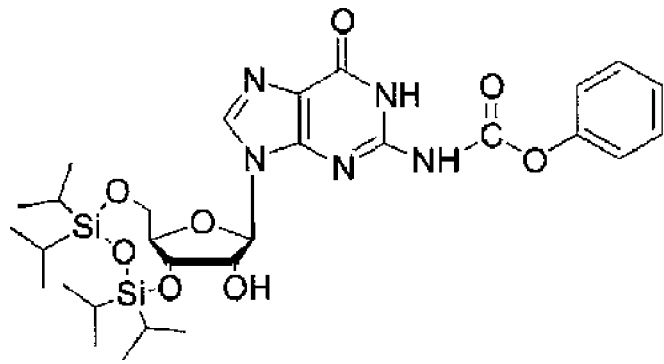 --, therefor.

In column 28, line 31-32, delete "3' phosphitylation" and insert -- 3'-phosphitylation --, therefor.

In column 29, in structure, line 8-23, delete " 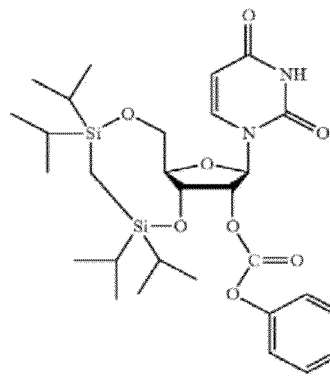 " and
insert -- 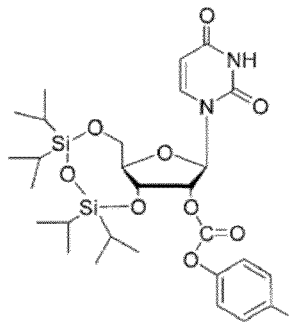 --, therefor.
In column 29, in structure, line 24-38, delete " 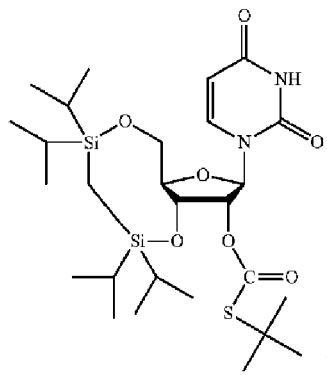 " and
insert -- 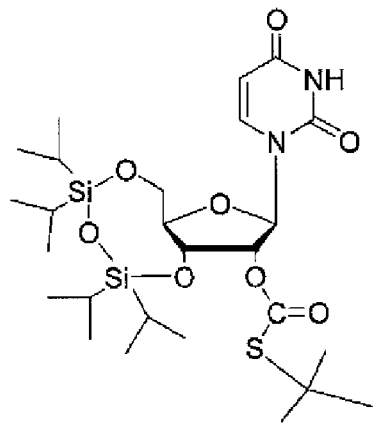 --, therefor.
In column 29, line 67, delete "4-(dimethyeaminopyridine" and insert -- 4-(dimethyl)aminopyridine --, therefor.
In column 30, line 16-17, delete "phosphytilating" and insert -- phosphitylating --, therefor.

In column 30, line 20, delete "phosphoramidite" and insert -- phosphoramidite. --, therefor.

In column 31, line 6, delete ""chemical array"" and insert -- "chemical array" --, therefor.

In column 31, line 37, delete "Sephacyl®," and insert -- Sephacryl®, --, therefor.

In column 32, line 34, delete "1, 2" and insert -- 1,2 --, therefor.

In column 35, line 46, delete "fluoroide" and insert -- fluoride --, therefor.

In column 35, line 51, delete "tehrahydrofuran," and insert -- tetrahydrofuran, --, therefor.

In column 35, line 53-54, delete "(tetrabutylamonium" and insert -- (tetrabutylammonium --, therefor.

In column 36, line 6, delete "et. al." and insert -- et al., --, therefor.

In column 36, line 19, delete "tetraalkylammoinum" and insert -- tetraalkylammonium --, therefor.

In column 36, line 20, delete "tertrabutylammonium" and insert -- tetrabutylammonium --, therefor.

In column 36, line 25, delete "biflouirde" and insert -- bifluoride. --, therefor.

In column 36, line 29-30, delete "tetraalkylammoinum" and insert -- tetraalkylammonium --, therefor.

In column 36, line 45, delete "[HHF₂TBA]," and insert -- [HF$_2$TBA], --, therefor.

In column 37, line 43, delete "acetate(TBAA)" and insert -- acetate (TBAA) --, therefor.

In column 39-40, in structure, line 18-30, delete " 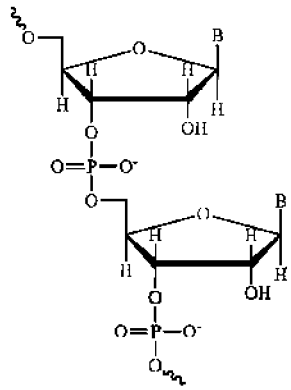 " and insert -- 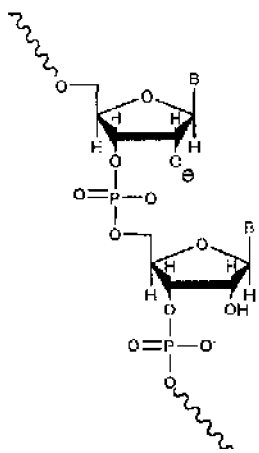 --, therefor.

In column 40, line 55, delete "pka" and insert -- pKa --, therefor.

In column 40, line 64, delete "salvation" and insert -- solvation --, therefor.

In column 41, line 42, delete "pka" and insert -- pKa --, therefor.

In column 42, line 31, delete "reagents" and insert -- reagents. --, therefor.

In column 44, line 1, delete "hinderance" and insert -- hindrance --, therefor.

In column 44, in structure, line 21-29, delete " 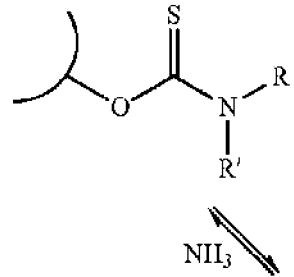 " and
insert -- 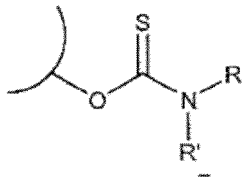 --, therefor.

In column 47, line 32, delete "al," and insert -- al., --, therefor.

In column 47, line 53, delete "mRNA" and insert -- iRNA --, therefor.

In column 47, line 54, delete "mRNA" and insert -- iRNA --, therefor.

In column 48, line 13, delete "mRNA" and insert -- iRNA --, therefor.

In column 51, line 56, delete "moleculeses," and insert -- molecules, --, therefor.

In column 51, line 57, delete "hecigenin," and insert -- hecogenin, --, therefor.

In column 51, line 66, delete "polylysine" and insert -- poly I'lysine --, therefor.

In column 52, line 1, delete "glycolied)" and insert -- glycolide) --, therefor.

In column 52, line 6-7, delete "polylysine" and insert -- poly I'lysine --, therefor.

In column 52, line 15, delete "polyaminoacid," and insert -- polyamino acid, --, therefor.

In column 52, line 34, delete "japlakinolide," and insert -- jasplakinolide, --, therefor.

In column 52, line 35-36, delete "myoservin." and insert -- myoseverin. --, therefor.

In column 52, line 43, delete "neproxin" and insert -- naproxen --, therefor.

In column 52, line 47, delete "USA." and insert -- HSA. --, therefor.

In column 54, line 9-10, delete "intracheal," and insert -- intratracheal, --, therefor.

In column 56, line 11, delete "neet" and insert -- neat --, therefor.

In column 56, line 12, delete "neet" and insert -- neat --, therefor.

In column 57-58, line 2, delete "MeO [N(iPr)$_2$]Cl," and insert -- MeO P [N(iPr)$_2$]Cl, --, therefor.

In column 57, line 48, delete "hours" and insert -- hours. --, therefor.

In column 57, line 53, delete "(M+Cl)" and insert -- (M+Cl). --, therefor.

In column 60, line 25, delete "25%)" and insert -- 25%). --, therefor.

In column 60, line 37, delete "Ethychlorothioformate" and insert -- Ethylchlorothioformate --, therefor.

In column 61-62, line 5, delete " 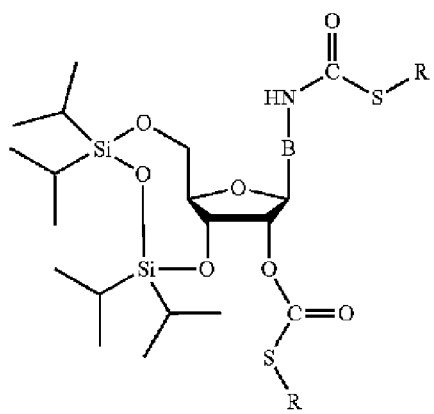 " and insert -- 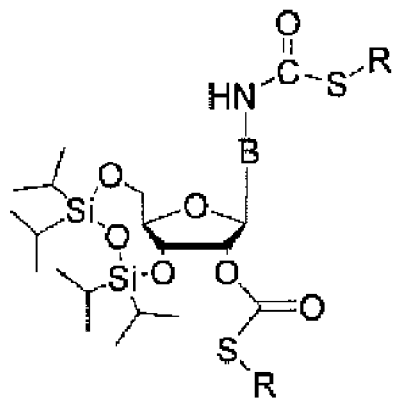 --, therefor.
In column 61-62, line 5, delete " 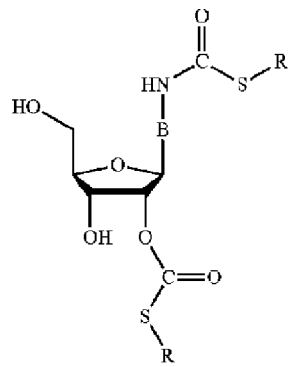 " and insert -- 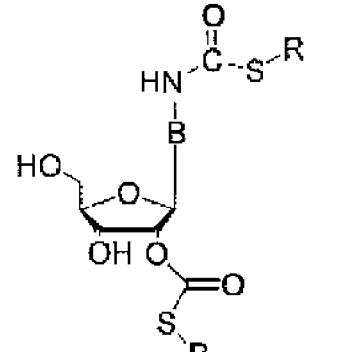 --, therefor.

CERTIFICATE OF CORRECTION (continued)
U.S. Pat. No. 9,067,961 B2

In column 61-62, line 6, delete " 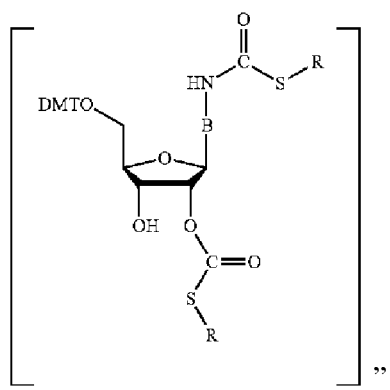 " and insert -- 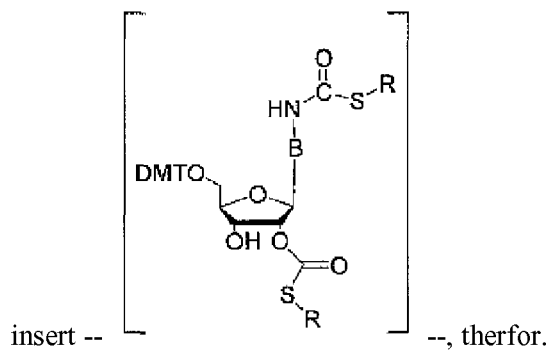 --, therfor.

In column 61-62, line 6, delete " 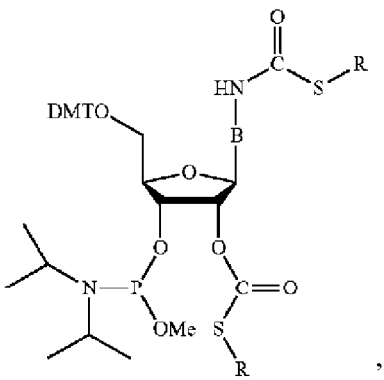 " and insert -- 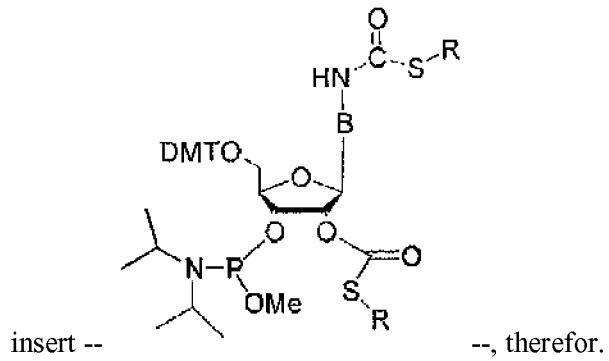 --, therefor.

In column 62, line 56, delete "5',3'TIPS" and insert -- 5',3'-TIPS --, therefor.

In column 63, line 19, delete "(ChemeGenes)," and insert -- (ChemGenes), --, therefor.

In column 63, line 20, delete "acetonitril" and insert -- acetonitrile --, therefor.

In column 64, line 7, delete "(ChemeGenes)," and insert -- (ChemGenes), --, therefor.

In column 64, line 8, delete "acetonitril" and insert -- acetonitrile --, therefor.

In column 64, line 33, delete "5',3'-β-" and insert -- 5',3'-O- --, therefor.

In column 65, line 13, delete "5',3'-β-" and insert -- 5',3'-O- --, therefor.

In column 66, line 22, delete "pyridine-HE" and insert -- pyridine-HF --, therefor.

In column 66, line 67, delete "on" and insert -- one --, therefor.

In column 67, line 2, delete "(1 mL)" and insert -- (1 mL). --, therefor.

In column 67, line 27, delete "neet" and insert -- neat --, therefor.

In column 67, line 27, delete "neet" and insert -- neat --, therefor.

In column 67, line 36, delete "neet" and insert -- neat --, therefor.

In column 67, line 44, delete "min]" and insert -- min]. --, therefor.

In column 67, line 55, delete "oligoribonulcleotide" and insert -- oligoribonucleotide --, therefor.

In column 67, line 60, delete "cytdine)" and insert -- cytidine) --, therefor.

In column 67, line 60, delete "$A^{POC}_{2'ESC}2'O$" and insert -- $A^{POC}_{2'ESC}2'O$ --, therefor.

In column 67, line 62, delete "cytdine)" and insert -- cytidine). --, therefor.

In column 68, line 49, delete "min" and insert -- min. --, therefor.

In column 69, line 47, delete "dimithylaminopyridine" and insert -- dimethylaminopyridine --, therefor.

In the Claims

In column 73, in structure, line 3-15, In Claim 7, delete " 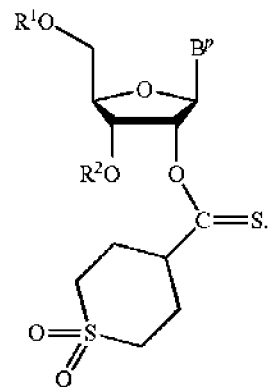 " and insert -- 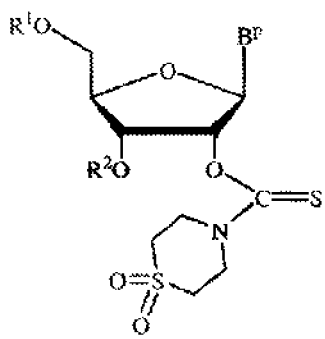 --, therefor.
In column 74, in structure, line 1-12, In Claim 14, delete " 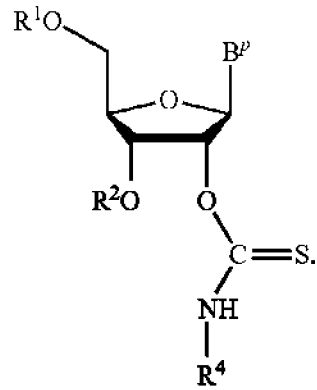 " and insert -- 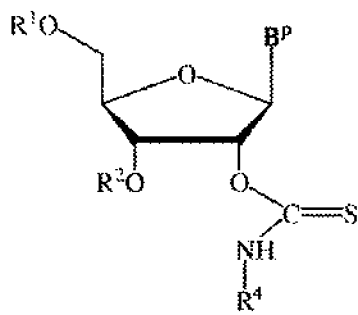 --, therefor.

In column 74, in structure, line 27-39, In Claim 15, delete " 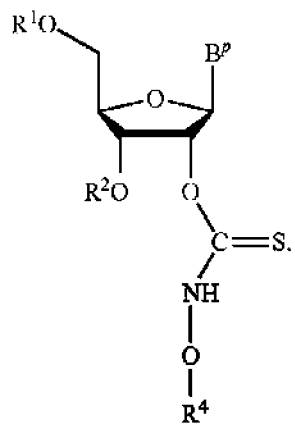 " and insert -- 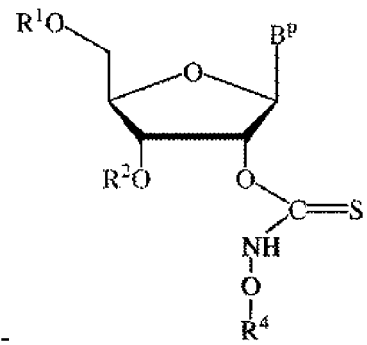 --, therefor.
In column 75, in structure, line 53-66, In Claim 17, delete " 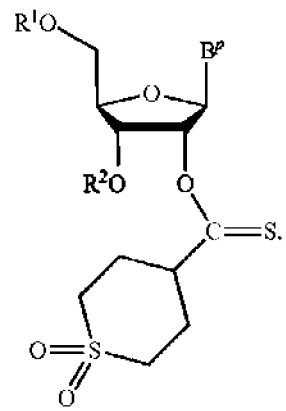 " and insert -- 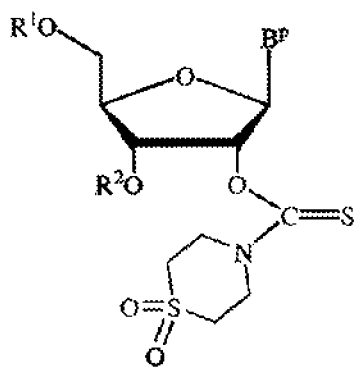 --, therefor.